United States Patent
Cao et al.

(10) Patent No.: US 12,116,603 B2
(45) Date of Patent: Oct. 15, 2024

(54) RNA SILENCING NANOZYMES

(71) Applicant: University of Florida Research Foundation, Inc., Gainesville, FL (US)

(72) Inventors: Yunwei Charles Cao, Gainesville, FL (US); Tian Jiang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 259 days.

(21) Appl. No.: 17/091,735

(22) Filed: Nov. 6, 2020

(65) Prior Publication Data

US 2021/0139873 A1    May 13, 2021

Related U.S. Application Data

(63) Continuation-in-part of application No. PCT/US2019/042326, filed on Jul. 18, 2019.

(60) Provisional application No. 62/699,913, filed on Jul. 18, 2018.

(51) Int. Cl.
| | | |
|---|---|---|
| *C12N 9/22* | (2006.01) | |
| *C12N 15/01* | (2006.01) | |
| *C12N 15/10* | (2006.01) | |

(52) U.S. Cl.
CPC ............... *C12N 9/22* (2013.01); *C12N 15/01* (2013.01); *C12N 15/102* (2013.01); *C12N 2310/52* (2013.01); *C12Y 301/27005* (2013.01)

(58) Field of Classification Search
CPC ........ C12N 9/22; C12N 15/01; C12N 15/102; C12N 2310/52; C12N 15/1131; C12N 2310/20; C12N 15/111; C12N 9/96; C12N 15/11; C12Y 301/27005; A61K 38/00
See application file for complete search history.

(56) References Cited

U.S. PATENT DOCUMENTS

| | | |
|---|---|---|
| 2005/0164292 A1 | 7/2005 | Farooqui et al. |
| 2008/0299565 A1 | 12/2008 | Schneider et al. |
| 2015/0315588 A1 | 11/2015 | Uhlmann et al. |
| 2016/0215279 A1 | 7/2016 | Cao et al. |
| 2017/0253911 A1* | 9/2017 | Schildkraut ........ C12N 15/1003 |

OTHER PUBLICATIONS

Rutkoski, Antitumor Activity of Ribonuclease Multimers Created by Site-Specific Covalent Tethering, Bioconjug Chem. 2010 21:1691-1702.
Scaggiante et al., Improving siRNA Bio-Distribution and Minimizing Side Effects, Curr Drug Metab 2011, 12:11-23.
Schnettler et al., The NS3 protein of rice hoja blanca virus complements the RNAi suppressor function of HIV-1 Tat, Embo Rep 2009, 10:258-263.
Shchepinov et al., The Synthesis of Branched Oligonucleotide Structures, Bioorg Khim+ 1998, 24:794-797.
Shchepinov et al., Oligonucleotide dendrimers: synthesis and use as polylabelled DNA probes, Nucleic Acids Res 1997, 25:4447-4454.
Sokol et al., Real time detection of DNAzRNA hybridization in living cells, P Natl Acad Sci USA 1998, 95:11538-11543.
Song et al., Crystal Structure of Argonaute and Its Implications for RISC Slicer Activity, Science 2004, 305:1434-1437.
Sontheimer et al., Argonaute Journeys into the Heart of RISC, Science 2004, 305:1409-1410.
Southern et al., Arrays of complementary oligonucleotides for analysing the hybridisation behaviour of nucleic acids, Nucleic Acids Res 1994, 22:1368-1373.
Southern et al., Analyzing and Comparing Nucleic Acid Sequences by Hybridization to Arrays of Oligonucleotides: Evaluation Using Experimental Models, Genomics 1992, 13:1008-1017.
Tsai et al., Viral hepatocarcinogenesis, Oncogene 2010, 29:2309-2324.
Tsourkas et al., Hybridization of 2'-O-methyl and 2'-deoxy molecular beacons to RNA and DNA targets, Nucleic Acids Res 2002, 30:5168-5174.
Tyagi et al., Molecular Beacons: Probes that Fluoresce upon Hybridization, Nat Biotechnol 1996, 14:303-308.
Tyagi et al., Multicolor molecular beacons for allele discrimination, Nat Biotechnol 1998, 16:49-53.
Vargas et al., Mechanism of mRNA transport in the nucleus, P Natl Acad Sci USA 2005, 102:17008-17013.

(Continued)

*Primary Examiner* — Delia M Ramirez
(74) *Attorney, Agent, or Firm* — Thomas|Horstemeyer, LLP

(57) ABSTRACT

Disclosed herein are improved nanozymes for targeting RNA. The disclosed nanozymes are synthesized using recombinant RNase A with site-specific cysteine-substituted mutations that can be covalently functionalized with a length-tunable multi-thiol tether and then loaded onto gold particles through multiple gold-sulfur bonds. This new RNase A loading mechanism is site specific, and it allows high-density loading of alkylthiol modified DNA oligonucleotides. The disclosed nanozymes can also include additional capturer strands and/or involve DNA-recombinant-RNase-A unibodies to further increase the nanozyme's enzymatic activity and target selectivity. Also disclosed are functional on-off switchable nanozymes to control nanozyme activity. In some embodiments, the disclosed nanozyme are core-free hollow forms. The removal of the inorganic nanoparticle cores from nanozymes can effectively eliminate the potential long-term toxicity induced by the core, and also creates a cavity for loading and delivery of small molecule drugs.

8 Claims, 54 Drawing Sheets

Specification includes a Sequence Listing.

(56) References Cited

OTHER PUBLICATIONS

Wang et al., Molecular Engineering of DNA: Molecular Beacons, Angew Chem Int Edit 2009, 48:856-870.
Wang et al., Locked Nucleic Acid Molecular Beacons, J Am Chem Soc 2005, 127:15664-15665.
Wang et al., Nanoparticle-based artificial RNA silencing machinery for antiviral therapy, P Natl Acad Sci USA 2012, 109:12387-12392.
Wang et al., Biomimetic RNA-Silencing Nanocomplexes: Overcoming Multidrug Resistance in Cancer Cells, Angewandte Chemie International Edition, vol. 53, Issue: 7, p. 1997-2001, 2014.
Whitesides et al., Molecular Self-Assembly ad Nanochemistry: A Chemical Strategy for the Synthesis of Nanostructures, Science 1991, 254:1312-1319.
Wolf et al., An in vivo RNAi screen identifies SALL1 as a tumor suppressor in human breast cancer with a role in CDH1 regulation, Oncogene 2014, 33:4273-4278.
Xue et al., Quantifying thiol-gold interactions towards the efficient strength control, Nature Communications, Issue: 5, Article No. 4348, 2014.
Yehl et al., Catalytic Deoxyribozyme-Modified Nanoparticles for RNAi-Independent Gene Regulation, ACS Nano, vol. 6, Issue: 10, p. 9150-9157, 2012.
Yokota et al., Inhibition of intracellular hepatitis C virus replication by synthetic and vector-derived small interfering RNAs, Embo Rep 2003, 4:602-608.
Young et al., Nanoparticle-siRNA: A potential cancer therapy?, Crit Rev Oncol Hemat 2016, 98:159-169.
Zhang et al., Self-assembled gold nanocrystal micelles act as an excellent artificial nanozyme with ribonuclease activity, JBIC Journal of Biological Inorganic Chemistry, vol. 14, Issue: 5, p. 653-662, 2009.
Zhu et al., Gene Expression Associated With Interferon Alfa Antiviral Activity in an HCV Replicon Cell Line, Hepatology 2003, 37:1180-1188.
International Search Report issued for PCT/US2019/042326, mailed Oct. 23, 2019.
Rutkoski, Engineering Ribonuclease-Based Cancer Therapeutics, University of Wisconsin-Madison, Dissertation, 2008.
Wang et al., A multi-coordinating polymer ligand optimized for the fictionalization of metallic nanocrystals and nanorods, Faraday Discussions, vol. 191, p. 481-494, 2016.
Li et al., Multiple thiol-anchor capped DNA-gold nanoparticle conjugates, Nucleic Acids Research, vol. 30, In 7, p. 1558-62, 2002.
Faghihi et al., Evidence for natural antisense transcript-mediated inhibition of microRNA function, Genome Biology, p. 1-13, 11:R56, 2010.
Abel et al., Fluorescence Assay for the Binding of Ribonuclease A to the Ribonuclease Inhibitor Protein, Anal Biochem 2002, 306:100-107.
Badwaik et al., Structure-property relationship for in vitro siRNA delivery performance of cationic 2-hydroxypropyl-b-cyclodextrin:PEG-PPGPEG polyrotaxane vectors, Biomaterials 2016, 84:86-98.
Bae et al., Ultrasound-Guided Delivery of siRNA and a Chemotherapeutic Drug by Using Microbubble Complexes: In Vitro and In Vivo Evaluations in a Prostate Cancer Model, Korean J Radiol 2016, 17:497-508.
Barnaby et al., Design Consideration for RNA Spherical Nucleic Acids (SNAs), Bioconjugate Chemistry, vol. 27, Issue: 9, p. 2124-2131, 2016.
Bhandare et al., Identification of possible siRNA molecules for TDP43 mutants causing amyotrophic lateral sclerosis: In silico design and molecular dynamics, Comput Biol Chem 2016, 61:97-108.
Bivalkar-Mehla et al., Viral RNA Silencing Suppressors (RSS): Novel Strategy of Viruses to Ablate the Host RNA Interference (RNAi) Defense System, Virus Res 2011, 155:1-9.
Bogen et al., Adoptive Transfer of Tumor-Specific Th2 Cells Eradicates Tumors by Triggering an In Situ Inflammatory Immune Response, Cancer Res 76, 6864-6877, 2016.
Boussif et al., A versatile vector for gene and oligonucleotide transfer into cells in culture and in vivo: Polyethylenimine, P Natl Acad Sci USA 1995, 92:7297-7301.
Briley et al., Quantification and real-time tracking of RNA in live cells using Sticky-flares, P Natl Acad Sci USA 2015, 112:9591-9595.
Brummelkamp et al., A System for Stable Expression of Short Interfering RNAs in Mammalian CellsScience 2002, 296:550-553.
Cerritelli et al., Ribonuclease H: the enzymes in eukaryotes, Febs J 2009, 276:1494-1505.
Conlon et al., Pyrene Excimer Signaling Molecular Beacons for Probing Nucleic Acids, J Am Chem Soc 2008, 130:336-342.
Corbet et al., Delivery of siRNA targeting tumor metabolism using non-covalent PEGylated chitosan nanoparticles: Identification of an optimal combination of ligand structure, linker and grafting methodJ Control Release 2016, 223:53-63.
Crook et al., Spectrophotometric Assay of Bovine Pancreatic Ribonuclease by the use of Cytidine 2':3'-Phosphate, Biochem J 1960 74:234-238.
D'Avino et al., Effects of a second-generation human anti-ErbB2 ImmunoRNase on trastuzumab-resistant tumors and cardiac cells, Protein Eng Des Sel 2014, 27:83-88.
Delcardayre et al., Engineering ribonuclease A: Production, purification and characterization of wild-type enzyme and mutants at Gln11, Protein Eng 1995 8:261-273.
Demers et al., A Fluorescence-Based Method for Determining the Surface Coverage and Hybridization Efficiency of Thiol-Capped Oligonucleotides Bound to Gold Thin Films and Nanoparticles, Abstr Pap Am Chem S 2000, 219:U870-U870.
Fire et al., Potent and specific genetic interference by double-stranded RNAin Caenorhabditis elegans, Nature 1998, 391:806-811.
Futami et al., Design of Cytotoxic Ribonucleases by Cationization to Enhance Intracellular Protein Delivery, Curr Pharm Biotechno 2008, 9:180-184.
Giljohann et al., Gene Regulation with Polyvalent siRNA-Nanoparticle Conjugates, J Am Chem Soc 2009, 131:2072.
Giljohann et al., Gold Nanoparticles for Biology and Medicine, Angew Chem Int Edit 2010, 49:3280-3294.
Grishok et al., Genes and Mechanisms Related to RNA Interference Regulate Expression of the Small Temporal RNAs that Control C. elegans Developmental Timing, Cell 2001, 106:23-34.
Horn et al., Chemical synthesis and characterization of branched oligodeoxyribonucleotides (bDNA) for use as signal amplifiers in nucleic acid quantification assays, Nucleic Acids Res 1997, 25:4842-4849.
Horn et al., An improved divergent synthesis of comb-type branched oligodeoxyribonucleotides (bDNA) containing multiple secondary sequences, Nucleic Acids Res 1997, 25:4835-4841.
Horn et al., Forks and combs and DNA: the synthesis of branched oligodeoxyribonucleotides, Nucleic Acids Res 1989, 17:6959-6967.
Hurst et al., Maximizing DNA Loading on a Range of Gold Nanoparticle Sizes, Anal Chem. 2006 78:8313-8318.
Jansen et al., Encapsulation of Guest Molecules into a Dendritic Box, Science 1994, 266:1226-1229.
Johnson et al., Cytotoxic Ribonucleases: The Dichotomy of Coulombic Forces, Biochemistry—Us 2007, 46:10308-10316.
Judge et al., Sequence-dependent stimulation of the mammalian innate immune response by synthetic siRNA, Nat Biotechnol 2005, 23:457-462.
Kaya et al., Guided Tour to the Heart of RISC, Science 2012, 336:985-986.
Kelemen et al., Hypersensitive substrate for ribonucleases, Nucleic Acids Res 1999, 27:3696-3701.
Kelly et al., Presence of a lysosomal enzyme, arylsulfatase-A, in in the prelysosme-endosome compartments of huma cultured fibroblasts, European Journal of Cell Biology 1989, 48:71-78.
Kobe et al., Mechanism of Ribonuclease Inhibition by Ribonuclease Inhibitor Protein Based on the Crystal Structure of its Complex with Ribonuclease A, J Mol Biol 1996, 264:1028-1043.
Leland et al., Ribonuclease A variants with potent cytotoxic activity, P Natl Acad Sci USA 1998, 95:10407-10412.

(56) References Cited

OTHER PUBLICATIONS

Li et al., An Artificial Supramolecular Nanozyme Based on β-Cyclodextrin-Modified Gold Nanoparticles, Catalysis Letters, vol. 124, Issue: 3-4, p. 413-417, 2008.

McMullan et al., Evidence for a functional RNA element in the hepatitis C virus core gene, P Natl Acad Sci USA 2007, 104:2879-2884.

Marques et al., Activation of the mammalian immune system by siRNAs, Nat Biotechnol 2005, 23:1399-1405.

Messmore et al., Ribonuclease A: Revealing Structure-Function Relationships with Semisynthesis, J Am Chem Soc 1995, 117:8057-8060.

Min et al., Microenvironmental Remodeling as a Parameter and Prognostic Factor of Heterogeneous Leukemogenesis in Acute Myelogenous Leukemia, Cancer Res 2015, 75.

Palliser et al., An siRNA-based microbicide protects mice from lethal herpes simplex virus 2 infection, Nature 2006, 439:89-94.

Park et al., Array-Based Electrical Detection of DNA with Nanoparticle Probes, Science 2002, 295:1503-1506.

Petree et al., Site-Selective RNA Splicing Nanozyme: DNAzyme and RtcB Conjugates on a Gold Nanoparticle, ACS Chemical Biology, vol. 13, Issue: 1, p. 215-224, 2017.

Praveen et al., Behavior of RNAi suppressor protein 2b of Cucumber mosaic virus in planta in presence and absence of virus, Virus Genes 2008, 37:96-102.

Randall et al., Clearance of replicating hepatitis C virus replicon RNAs in cell culture by small interfering RNAs, P Natl Acad Sci USA 2003, 100:235-240.

Rauschhuber et al., RNAi suppressor P19 can be broadly exploited for enhanced adenovirus replication and microRNA knockdown experimentsSci Rep-Uk 2013, 3.

Rimessi et al., Nanoparticle-Mediated Delivery of Antisense Oligoribonucleotides Allows Restoration of Dystrophin Expression in the mdx Mouse, Mol Ther 2009, 17:S336-S336.

Rizzo et al., Chimeric RNAÿDNA molecular beacon assay for ribonuclease H activity, Mol Cell Probe 2002, 16:277-283.

Rosi et al., Oligonucleotide-Modified Gold Nanoparticles for Intracellular Gene Regulation, Science 2006, 312:1027-1030.

Rutkoski et al., Site-specific PEGlation endows a mammalian ribonuclease with antitumor activity, Cancer Biol Ther 2011, 12:208-214.

Rutkoski et al., Evasion of Ribonuclease Inhibitor as a Determinant of Ribonuclease Cytotoxicity, Curr Pharm Biotechno 2008, 9:185-199.

* cited by examiner

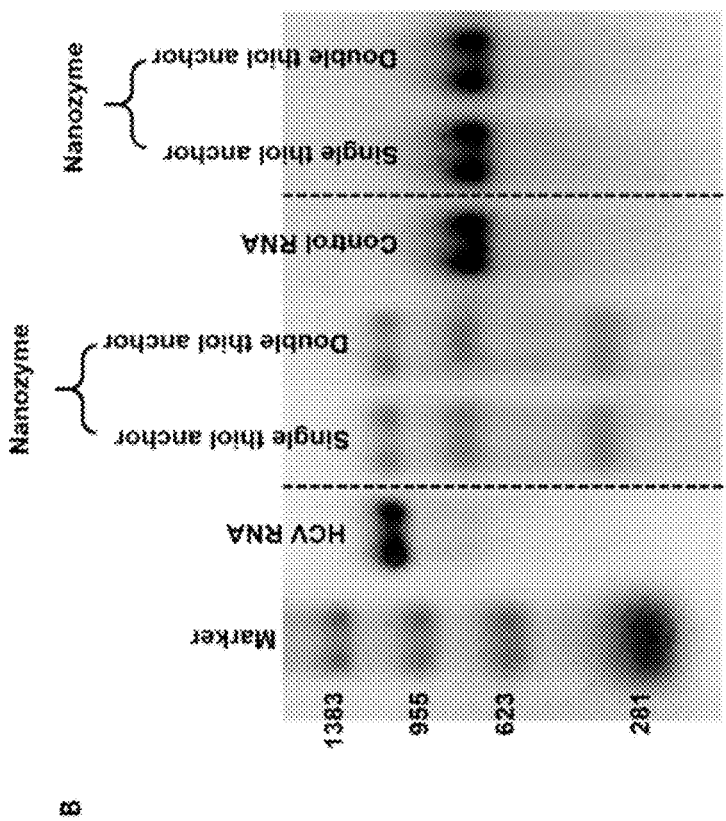
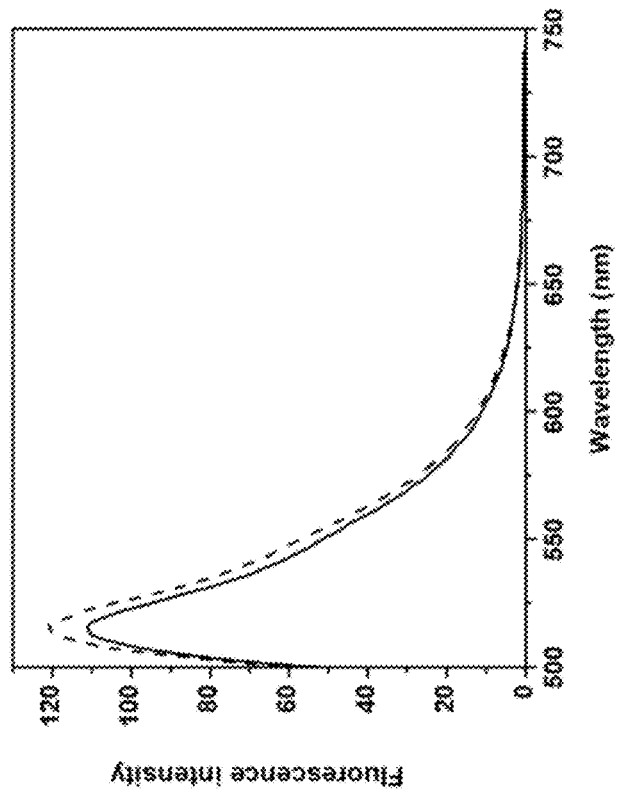
FIG. 22B
FIG. 22A

RNA SILENCING NANOZYMES

CROSS-REFERENCE TO RELATED APPLICATIONS

This application is a continuation-in-part of copending International Application Serial No. PCT/US2019/042326, filed Jul. 18, 2019, which claims benefit of U.S. Provisional Application No. 62/699,913, filed Jul. 18, 2018, which is hereby incorporated herein by reference in its entirety.

STATEMENT REGARDING FEDERALLY SPONSORED RESEARCH OR DEVELOPMENT

This invention was made with government support under DMR1710509 awarded by the National Science Foundation. The government has certain rights in the invention.

SEQUENCE LISTING

This application contains a sequence listing filed in electronic form as an ASCII.txt file entitled "222107-2270 Sequence Listing_ST25" created on Jul. 17, 2019. The content of the sequence listing is incorporated herein in its entirety.

BACKGROUND

To date, enzymes have been widely used in medicine. Most enzymes are used extracellularly for topical applications (e.g., collagenase), removal of toxic substances (e.g., rhodonase), and disorders within blood circulation system (e.g., urokinase). In addition, enzymes have a major potential application in treatment of cancer, e.g., asparagenase in the treatment of lymphocytic leukemia. However, enzyme applications in medicine are limited by and suffer from many limitations such as enzyme target specificity, enzyme stability against proteinase, and enzyme activity in the presence of its inhibitors in physiological environments, such as inside cytoplasmic matrix. Thus, there is a need to overcome limitation associated with enzyme.

SUMMARY

Disclosed herein are improved RNA silencing nanozymes. Nanozymes are engineered cellular machines containing oligonucleotides that act like siRNA strands in that they complement the target RNAs, while also containing an endoribonucleases to cleave those target RNAs.

First, the disclosed nanozymes can be synthesized using recombinant RNase A with a site-specific cysteine-substituted mutation. These RNase A mutants can be covalently functionalized with a length-tunable multi-thiol tether at the mutated cysteine site, and then loaded onto gold particles through multiple gold-sulfur bonds. The disclosed RNase A loading mechanism is site specific, and it allows high-density loading of alkylthiol modified DNA oligonucleotides, which would result in successful preparation of nanozymes with high target selectivity in a very controllable fashion.

Therefore, disclosed herein is a nanozyme that comprises a nanoparticle, an engineered RNase-A enzyme, and a oligonucleotide, wherein the oligonucleotide comprises a first RNA recognition moiety comprising a nucleic acid sequence complementary to a first region of an RNA target, wherein the recombinant RNase A enzyme comprises a mutated cysteine residue that is covalently linked with a length-tunable tether with a multi-thiol anchor group, wherein the engineered RNase A enzyme and the oligonucleotide are independently or collectively attached to the nanoparticle, and wherein the RNA target is cleaved by the engineered RNase A enzyme when the first RNA recognition moiety binds to the RNA target.

In some embodiments, the nanoparticle is gold, and the engineered RNase A enzyme and the DNA oligonucleotide are independently or collectively attached to the gold nanoparticle through gold-sulfur bonds. Other suitable nanoparticle materials include silver, iron oxide/gold core/shell nanoparticles, and II-VI semiconductor nanoparticles such as CdSe, CdS, and ZnS.

In some embodiments, the oligonucleotide is a DNA oligonucleotide. However, other suitable oligonucleotides are known in the art and include locked nucleic acid (LNA) oligonucleotides, peptide nucleic acid (PNA) oligonucleotides, and 2'-O-methyl RNA oligonucleotides.

The engineered RNase A enzyme is mutated to contain a cysteine so that it can be covalently functionalized with a length-tunable tether with a multi-thoil anchor group.

Cysteine substitutions can in some embodiments be made within the RNase A enzyme at any location that does not inhibit enzymatic activity or cause steric hindrance. In some embodiments, the recombinant RNase A enzyme comprises a cysteine substitution at amino acid residue Ala19, Gly88, Asp38, Asn67, Ala109, or a combination thereof.

Second, the disclosed nanozymes can include double capturer strands and/or DNA-recombinant-RNase-A unibodies to further increase the nanozyme's enzymatic activity and target selectivity. Therefore, in some embodiments, the disclosed nanozyme further comprises a second RNA recognition moiety comprising a nucleic acid sequence complementary to a second region of the RNA target, wherein the RNA target is cleaved by the recombinant RNase-A enzyme when both the first RNA recognition moiety and the second RNA recognition moiety binds to the RNA target. This second RNA recognition moiety can be on a separate DNA oligonucleotide independently attached to the gold nanoparticle, or it can be attached to the first RNA recognition moiety by a brancher molecule (e.g. 5-Me-dC), which is attached to the gold nanoparticle. Compositions and methods for producing branched oligonucleotides are disclosed in Southern, E M, et al. Nucleic Acids Res 1994, 22:1368-1373; Horn, T, et al. Nucleic Acids Res 1997, 25:4842-4849; and Horn, T, et al. Nucleic Acids Res 1997, 25:4835-4841, which are incorporated by reference in their entirety for the teaching of these compositions and methods.

Also disclosed are functional on-off switchable nanozymes. This design introduces an addition factor to control nanozyme activity, and thus allows specifically targeting a cell type where exists activators (such as a sequence-specific RNA and DNA, a peptide or a protein). Therefore, in some embodiments the DNA oligonucleotide further comprises a blocker moiety comprising a nucleic acid sequence complementary to a blocker oligonucleotide, wherein binding of the blocker oligonucleotide to the blocker moiety sterically inhibits the RNA target from binding to the first RNA recognition site.

The recombinant RNase A and the DNA oligonucleotide can independently attached to the gold nanoparticle. Therefore, in some embodiments, the DNA oligonucleotide is thiol-modified and is directly attached to the gold nanoparticle by a gold-sulfur bond. In other embodiments, the RNase A enzyme and DNA oligonucleotide(s) are present on the same molecule (unibody) that is attached to the gold nanoparticle. This allows greater control over the relative loading density of the recognition elements and enzymes. Therefore, in some embodiments, the nanozyme comprises a unibody molecule attached to the gold nanoparticle by a gold-sulfur bond, wherein the unibody comprises a recombinant RNase A enzyme and a first RNA recognition moiety, a second RNA recognition moiety, or a combination and/or a plurality thereof. In some embodiments, a plurality of first RNA recognition moieties and/or second RNA recognition moieties are connected by brancher molecules.

In some embodiments, the disclosed nanozyme are core-free hollow forms (H-Nanozymes). The removal of the inorganic nanoparticle cores from nanozymes can effectively eliminate the potential long-term toxicity induced by the core, and also creates a cavity for loading and delivery of small molecule drugs, such as sorafenib for cancer treatment. Therefore, also disclosed herein is a hollow nanozyme produced by a process comprising, affixing to a gold nanoparticle by gold-sulfur bonds, a recombinant RNase-A enzyme comprising a mutated cysteine residue that is functionalized with multi-alkylthiol-terminated sequences of poly-thymine bases modified with propargyl ether, and a first alkylthiol-terminated and propargyl-ether-modified DNA oligonucleotide comprising a first RNA recognition moiety comprising a nucleic acid sequence complementary a first region of an RNA target; wherein the recombinant RNase-A enzyme comprises a mutated cysteine residue that is functionalized with multi-alkylthiol-terminated sequences of poly-thymine bases modified with propargyl ether; polymerizing the propargyl ether groups; and removing the gold nanoparticle with potassium cyanide thereby producing a inorganic-core-free, pure-organic hollow nanoenzyme, wherein upon binding of the first RNA recognition moiety to the RNA target the RNA target is cleaved by the recombinant RNase-A enzyme.

Also disclosed herein are methods of silencing RNA using the disclosed nanozymes. The disclosed nanozymes are engineered cellular machines that mimic the RNA silencing function of RISC without disrupting natural processes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows qRT-PCR analyses of HCV RNA expression in the FL-Neo cells treated with anti-HCV nanozymes, DNA-NPs, control DNA-NPs, control nanozymes, and NZ-Ls at varying doses: 0.034 nM, 0.14 nM, and 0.54 nM. Abbreviations: Ctrl stands for blank control. Each bar presents the mean and standard deviation derived from three independent experiments; Student's t test, ns=non-significance: P>0.14, * for P<0.01, and * for P=0.00053. FIG. 3B shows qRT-PCR analysis of HCV RNA expression in the FL-Neo cells treated with nanozymes or DNA-NPs three times during seven days at concentration of 0.067 nM. ns: P=0.58, ** for P=0.00024. FIG. 3C shows western blot analysis of NS5A expression in the FL-Neo cells from the treatment in FIG. 3B, which was probed with anti-NS5A antibody and anti-β-actin antibody, respectively. The band intensity (NS5A/β-actin) relative to the control was found to be 0.25±0.02 in the cells treated with nanozymes, while it was 0.97±0.07 in the cells treated with DNA-NPs. FIG. 3D shows immunofluorescence analysis of HCV NS5A expression in the individual FL-Neo cells from the treatment in FIG. 3B. The cells were fixed and the HCV NS5A expression level was examined by using fluorescent immunostaining with anti-HCV NS5A antibody and secondary antibody (fluorescein isothiocyanate (FITC)-labeled goat anti-mouse immunoglobulin G antibody). The nuclei of the cells were stained with DAPI (4',6-diamidino-2-phenylindole) as an internal reference. Mean and standard deviation were derived from three independent experiments.

FIG. 22A shows fluorescence spectrum of OliGreen™ dye bound capturer 1 DNA with single thiol (solid line) and double thiol (dashed line) anchor released from 1.00 nm nanozyme IIa. The average number of oligonucleotide per one Au nanoparticle was 95.0±7.98 for single thiol DNA and 104±5.23 double thiol DNA. FIG. 22B shows ribonuclease activity tests for assessing the target selectivity of nanozyme IIa with single/double thiol anchor capturer 1 DNA.

FIG. 21B shows ribonuclease activity tests for assessing the target selectivity of nanozyme IIa with different oligonucleotide density.

FIG. 40 is a schematic representation of establishing an artificial Ebola testing model based on the intracellular self-replicating HCV RNA replicon (pJFH1). pJHF1 is the full length genomic replicon of HCV JFH1 strain, containing T7, T7 promoter, 5' UTR non-translation regions, NEO (neomycin phosphotransferase gene), EMCV IRES (encephalomyocarditis virus internal ribosomal entry site), structural proteins of HCV (C, P7, E1 and E2), nonstructural proteins of HCV (NS2, NS3, NS4A, NS4B, NS5A and NS5B), and 3' UTR non-translation region.

FIG. 41 is a schematic representation of establishing Huh7.5 cell line harboring HCV-Ebola hybrid replicon.

DETAILED DESCRIPTION

Figure 1:
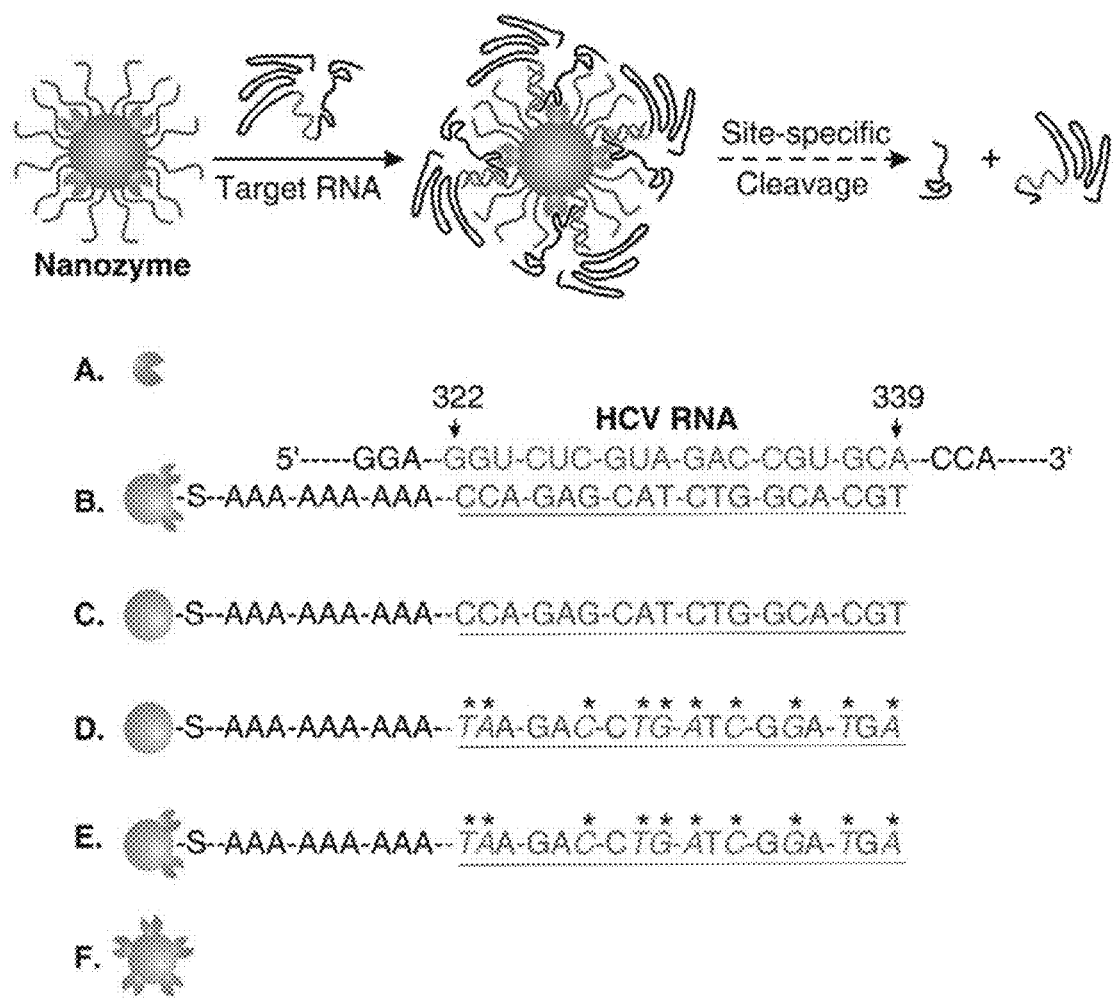
FIG. 1 is a schematic representation describing the design and function of a nanozyme: (A) an endoribonuclease, (B) a nanozyme with DNA oligonucleotides (SEQ ID NO:13 for underlined portion) complementary to the sequence at the HCV RNA position (322-339 nt, SEQ ID NO:12), (C) a DNA-NP: a nanozyme counterpart that does not bear endoribonucleases (SEQ ID NO:13 for underlined portion), (D) a control DNA-NP (SEQ ID NO:14 for underlined portion), (E) a control nanozyme (SEQ ID NO:14 for underlined portion), and (F) an RNase-NP.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Nanozymes

Embodiments of the present disclosure provides for nanozymes, methods of making nanozymes, methods of using nanozymes, and the like. In an embodiment, the nanozyme can include a gold nanoparticle, an enzyme, and a recognition moiety. Each of the enzyme and the recognition moiety are attached (e.g., directly or indirectly via a linker (e.g., compound or protein) or the like) to the nanoparticle by gold-sulfur bonds.

Kits

This disclosure encompasses kits, which include, but are not limited to, nanozymes, and directions (written instructions for their use). The components of the nanozyme can be tailored to the particular disease, condition, or even being studied and/or treated. The kit can further include appropriate buffers and reagents known in the art for administering various combinations of the components listed above to the host cell or host organism.

Example Aspects

Aspect 1. A nanozyme, comprising a gold nanoparticle, an engineered ribonuclease-A enzyme, and a DNA oligonucleotide,
wherein the DNA oligonucleotide comprises a first RNA recognition moiety comprising a nucleic acid sequence complementary to a first region of an RNA target,
wherein the engineered ribonuclease-A enzyme comprises a mutated cysteine residue that is functionalized with a length-tunable multi-thiol tether,
wherein the engineered ribonuclease-A enzyme and the DNA oligonucleotide are independently or collectively attached to the gold nanoparticle directly or indirectly by gold-sulfur bonds,
wherein the RNA target is cleaved by the engineered ribonuclease-A enzyme when the first RNA recognition moiety binds to the RNA target.

Aspect 2. The nanozyme of aspect 1, wherein the engineered ribonuclease-A enzyme comprises a cysteine substitution at amino acid residue A19, G88, or a combination thereof.

Aspect 3. The nanozyme of aspect 1 or 2, further comprising a second RNA recognition moiety comprising a nucleic acid sequence complementary to a second region of the RNA target, wherein the RNA target is cleaved by the recombinant RNase-A enzyme when both the first RNA recognition moiety and the second RNA recognition moiety binds to the RNA target.

Aspect 4. The nanozyme of any one of aspects 1 to 3, wherein the DNA oligonucleotide is thiol-modified and is directly attached to the gold nanoparticle by a gold-sulfur bond.

Aspect 5. The nanozyme of aspect 4, wherein the second RNA recognition moiety is located on a second thiol-modified DNA oligonucleotide attached to the nanoparticle by a gold-sulfur bond.

Aspect 6. The nanozyme of aspect 4, wherein the DNA oligonucleotide is a branched DNA oligonucleotide, and wherein the first RNA recognition moiety and the second RNA recognition moiety are linked by a brancher molecule.

Aspect 7. The nanozyme of aspect 6, wherein the brancher molecule comprises a 5-Me-dC brancher.

Aspect 8. The nanozyme of any one of aspects 1 to 7, wherein the DNA oligonucleotide further comprises a blocker moiety comprising a nucleic acid sequence complementary to a blocker oligonucleotide, wherein binding of the blocker oligonucleotide to the blocker moiety sterically inhibits the RNA target from binding to the first RNA recognition site.

Aspect 9. The nanozyme of any one of aspects 1 to 8, wherein the nanozyme comprises a unibody molecule attached to the gold nanoparticle by a gold-sulfur bond,
wherein the unibody comprises a recombinant RNase-A enzyme and a first RNA recognition moiety, a second RNA recognition moiety, or a combination and/or a plurality thereof.

Aspect 10. A hollow nanozyme produced by a process comprising, affixing to a gold nanoparticle by gold-sulfur bonds,
(a) an engineered ribonuclease-A enzyme comprising a mutated cysteine residue that is functionalized with multi-alkylthiol-terminated sequences of poly-thymine bases modified with propargyl ether, and
(b) a first alkylthiol-terminated and propargyl-ether-modified DNA oligonucleotide comprising a first RNA recognition moiety comprising a nucleic acid sequence complementary a first region of an RNA target;
wherein the recombinant RNase-A enzyme comprises a mutated cysteine residue that is functionalized with multi-alkylthiol-terminated sequences of poly-thymine bases modified with propargyl ether;
polymerizing the propargyl ether groups; and
removing the gold nanoparticle with potassium cyanide thereby producing a hollow nanoenzyme,
wherein upon binding of the first RNA recognition moiety to the RNA target the RNA target is cleaved by the engineered ribonuclease-A enzyme.

Aspect 11. A method for silencing RNA in a cell, comprising contacting the cell with the nanozyme of any one of aspects 1 to 10.

A number of embodiments of the invention have been described. Nevertheless, it will be understood that various modifications may be made without departing from the spirit and scope of the invention. Accordingly, other embodiments are within the scope of the following claims.

EXAMPLES

Messenger RNA (mRNA)—carrying the information of protein sequences and controlling the level of protein translation—are a major class of therapeutic targets for treating human diseases (Kim, D. H., et al. Nat Rev Genet 2007, 8:173-184). Two general methods have been developed to control the level of mRNA: antisense (Giljohann, D. A., et al. J Am Chem Soc 2009, 131:2072; Rosi, N. L., et al. Science 2006, 312:1027-1030) and RNAi (Grishok, A., et al. Cell 2001, 106:23-34; Fire, A., et al. Nature 1998, 391:806-811; Judge, A. D., et al. Nat Biotechnol 2005, 23:457-462; Brummelkamp, T. R., et al. Science 2002, 296:550-553). The antisense method is based on single-stranded nucleic acids, while RNAi uses double-stranded small interfering RNA (siRNA). Due to its high efficacy, RNAi is the primary method used for controlling mRNA levels (Badwaik, V. D., et al. Biomaterials 2016, 84:86-98; Bogen, D., et al. Cancer Res 2016, 76; Bhandare, V. V., et al. Comput Biol Chem 2016, 61:97-108; Bae, Y. J., et al. Korean J Radiol 2016, 17:497-508). Because these RNA-control methods are sequence specific, they have the potential to achieve effective personalized medicine for cancers and viral infections (Corbet, C., et al. J Control Release 2016, 223:53-63; Conlon, P., et al. J Am Chem Soc 2008, 130:336-342).

Successful delivery of predesigned synthetic nucleic acids to target tissues and even cells holds the key to these RNA-control methods and achieving successful RNA-based therapy. Various nanoparticle vehicles have been developed for RNA-based therapy for viral diseases and cancer (Min, L., et al. Cancer Res 2015, 75; Young, S. W. S., et al. Crit Rev Oncol Hemat 2016, 98:159-169). Shuttled by nanoparticle vehicles, antisense oligonucleotides exhibit enhanced inhibitory effects of cancer cell growth in mouse models (Rimessi, P., et al. Mol Ther 2009, 17:S336-S336); and synthetic siRNAs have achieved efficient (80%) silencing of the mRNA of hepatocyte-specific genes in mice models (Palliser, D., et al. Nature 2006, 439:89-94). In addition, spherical nucleic acids (SNAs) have been used to deliver both antisense DNA and siRNAs, which have both shown strong effects in controlling expression of protein in cells possess several unique characteristics (Briley, W. E., et al. P Natl Acad Sci USA 2015, 112:9591-9595): (1) they exhibit cooperative binding to their complementary target, (2) have higher binding constants for complements than free strands with the same sequence, (3) are resistant to nuclease degradation, and (4) are capable of transfecting living cell without the need of additional physical or chemical transfection methods.

All these RNA-based therapeutic approaches utilize cellular machineries such as RISC or RNase H to achieve their major therapeutic effects. However, this intervention could perturb natural cellular gene regulation pathways mediated by endogenous microRNAs that also rely on the same cellular machineries (Scaggiante, B., et al. Curr Drug Metab 2011, 12:11-23), thus resulting in potential toxicity and side effects. In addition, the therapeutic effects of siRNA can be inhibited by RNAi suppressors (Briley, W. E., et al. P Natl Acad Sci USA 2015, 112:9591-9595; Wolf, J., et al. Oncogene 2014, 33:4273-4278; Rauschhuber, C., et al. Sci Rep-Uk 2013, 3; Praveen, S., et al. Virus Genes 2008, 37:96-102; Bivalkar-Mehla, S., et al. Virus Res 2011, 155:1-9), which are encoded by pathogenic viruses such as the hepatitis C virus (HCV) and human immunodeficiency virus (HIV) (Schnettler, E., et al. Embo Rep 2009, 10:258-263).

Example 1: Nanozymes that Target HCV

To overcome this difficulty, biomimetic cellular machines can be designed that would not interfere with natural processes. Nanoparticles can be used as building blocks to construct multi-component macromolecular complexes (i.e., nanozymes, FIG. 1) for mimicking the RNA-cleavage function of the RISC machinery in vitro and in vivo.

In cellular RNAi pathways, RISC is an endoribonuclease-containing multiprotein complex that incorporates one strand of a siRNA (Kaya, E., et al. Science 2012, 336:985-986; Song, J. J., et al. Science 2004, 305:1434-1437; Sontheimer, E. J., et al. Science 2004, 305:1409-1410); it uses this single RNA strand to recognize and capture a complementary messenger RNA (mRNA) and then cleaves it into two pieces. Inspired by the structure and function of the RISC machinery, a nanozyme was designed that is comprised of a nanoparticle, single-stranded DNA, and sequence-nonspecific endo-ribonucleases. Due to gold's low toxicity and unique surface properties for alkylthiol functionalization (Rosi, N. L., et al. Science 2006, 312:1027-1030; Park, S. J., et al. Science 2002, 295:1503-1506; Giljohann, D. A., et al. Angew Chem Int Edit 2010, 49:3280-3294), gold nanoparticles were chosen as the backbone to provide a large surface area for holding single-strand DNA at close proximity to the catalytically active endoribonucleases-RNase A-which does not degrade single-stranded DNA but only sequence-nonspecifically degrades single-stranded RNA. Single-strand DNA recognize target RNA via Watson-Crick base pairing, and direct the neighboring endoribonucleases to cleave sequence complementary RNA. Also, it is well documented that RNase A can effectively bind onto gold nanoparticles through noncovalent adsorption.

HCV was chosen as a model system to evaluate the function and efficacy of the nanozyme for silencing gene expression and suppressing viral replication. HCV is a major cause of liver diseases such as chronic hepatitis, cirrhosis, and liver cancers (Tsai, W. L., et al. Oncogene 2010, 29:2309-2324). HCV is a positive-strand RNA virus and has six major genotypes and numerous subtypes. The 5' non-translated region (5' NTR) in the HCV genome is highly conserved among the six major genotypes and this region contains an important structure known as the internal ribosome entry site that controls the initiation of HCV RNA translation (Yokota, T., et al. Embo Rep 2003, 4:602-608; McMullan, L. K., et al. P Natl Acad Sci USA 2007, 104:2879-2884). Previous reports have shown that, by targeting this viral genomic region, siRNA 331 can effectively inhibit the replication of HCV in cultured cells (Yokota, T., et al. Embo Rep 2003, 4:602-608). The sequence of siRNA 331 was used in the design of an alkylthiol-terminated DNA oligonucleotide as the recognition component to synthesize anti-HCV nanozymes. This oligonucleotide consists of an $A_9$ tether and an 18 nucleotide (nt)-long fragment with sequence complementary to that of the region (nt 322-339) in the HCV genome; this $A_9$ tether was used as a spacer between the nanoparticle surface and the 18-nt recognition sequence for increasing the efficiency of the hybridization between a nanozyme and its complementary target (Demers, L. M., et al. Abstr Pap Am Chem S 2000, 219:U870-U870). A mutant version of the alkylthiol-terminated oligonucleotide with 9 mismatches was synthesized as a control DNA.

Nanozymes were synthesized using a two-step method. Gold was first functionalized with RNase A and then modified with the anti-HCV oligonucleotide (or the control DNA). The average numbers of RNase A and oligonucleotide on each nanozyme were determined using an RNase activity assay and the OliGreen assay, respectively.

To assess the target specificity of the anti-HCV nanozyme, an in vitro RNase activity assay was performed with DNA-NPs, control DNA-NPs, control nanozymes as negative controls, and particle-free RNase A as a positive control. The target substrate was an HCV RNA segment (nt 1-1149) that contains the entire 5' NTR region of the HCV RNA genome of the HCV JFH-1 strain. The control substrate was a 1257-nt RNA segment of human alpha-1 antitrypsin (AAT) gene that does not contain complementary sequences to the nanozyme-bearing oligonucleotides.

Figure 2A:
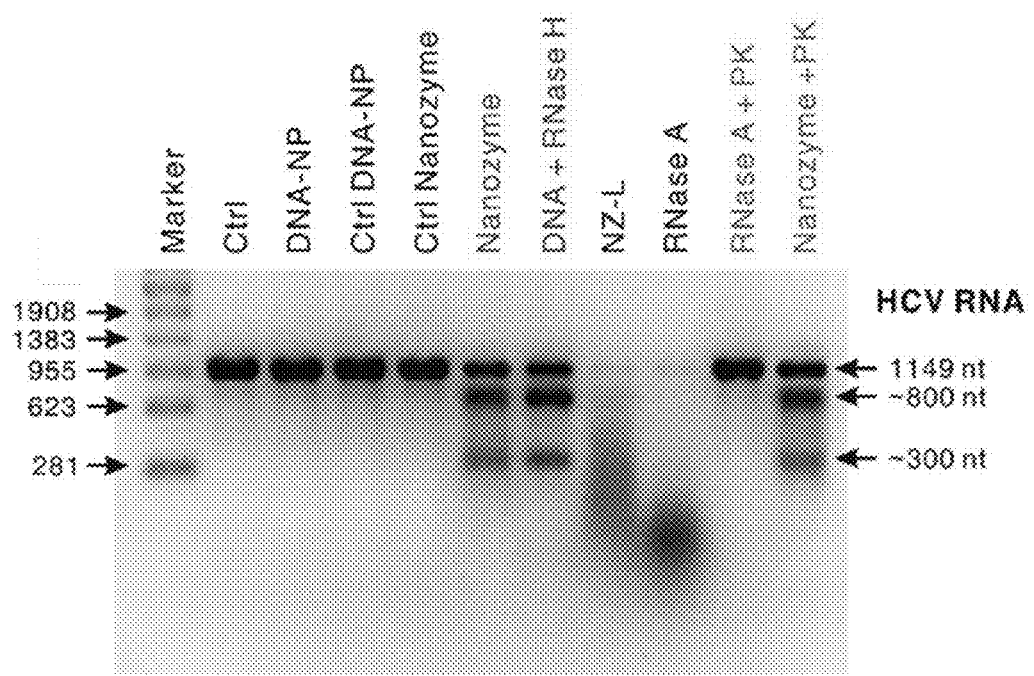
FIGS. 2A and 2B show ribonuclease activity tests for assessing the target selectivity of anti-HCV nanozyme and its ability to resist the degradation of proteinase activities. In these tests, the concentrations of anti-HCV nanozyme (or a control: DNA-NP, control DNA-NP, control nanozyme, and NZ-L) were 0.034 nM and that of unbound RNase A was 0.408 nM. The products of these tests were analyzed by using electrophoresis in a 2% formaldehyde agarose gel, and RNA bands were stained by using SYBR Green II. (A) HCV RNA segment (nt 1-1149) as the substrate. (B) 1257-nt AAT RNA segment as the substrate. In a typical proteinase K resistance test, nanozymes (0.034 nM) or particle-free RNase A (0.408 nM) were first incubated with proteinase K (10 nM) in a PBS buffer (pH 7.4) at 37° C. for 1 h. Then the product of this proteinase K treatment was divided into two parts and further incubated with the HCV (or AAT) RNA segment (0.12 μM) in a PBS buffer (11 μL; NaCl, 0.138 M; KCl, 0.027 M; pH 7.4) at 37° C. for 15 min. Abbreviations: Ctrl stands for blank control; and PK for proteinase K.
Figure 2B:
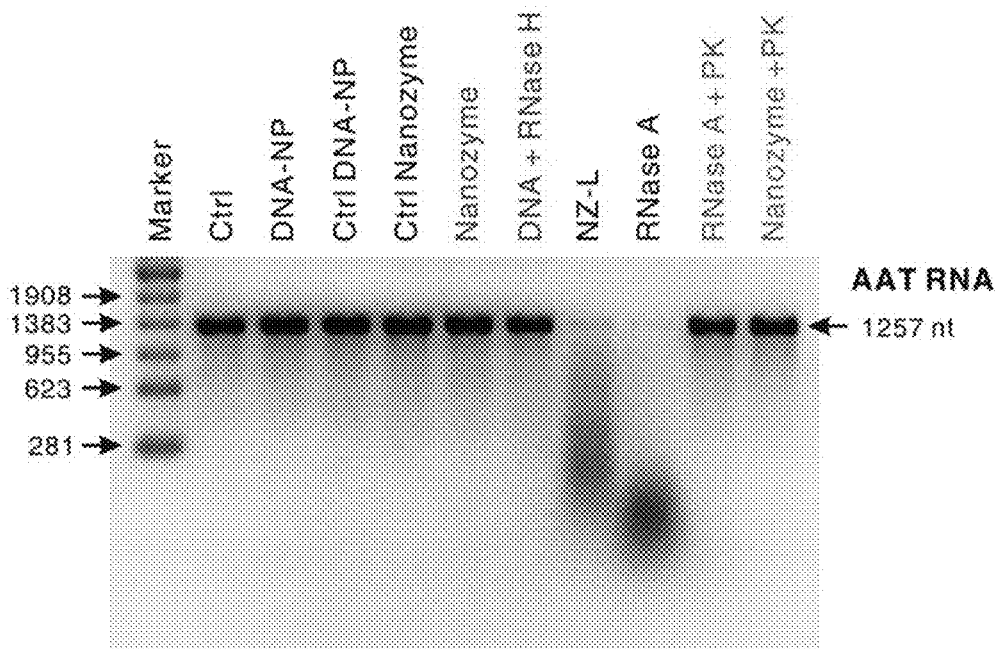

Electrophoresis analyses show that, while the anti-HCV nanozyme displayed no measurable cleavage activity on the AAT RNA, it did cleave the HCV RNA target into two major fragments with sizes of about 300 nt and 800 nt (FIG. 2A). This result corresponds to a RNA cleavage site fully matching the predicted position where the HCV RNA binds to the nanozyme via DNA/RNA hybridization (FIG. 1). In addition, the sizes of these two RNA fragments almost perfectly match the sizes of those corresponding HCV RNA fragments cut by RNase H—an endonuclease that specifically degrades the RNA of RNA-DNA hybrids (Cerritelli, S. M., et al. Febs J 2009, 276:1494-1505)—in the presence of the free anti-HCV DNA oligonucleotide (FIG. 2A); this result further suggests that the anti-HCV nanozyme induced site-specific RNA cleavage (FIG. 1). Moreover, RNase H showed no cleavage activity towards the mixture of AAT RNA and the anti-HCV oligonucleotide (FIG. 2B), which experimentally shows that AAT RNA does not have complementary sequences to the anti-HCV oligonucleotide (Cerritelli, S. M., et al. Febs J 2009, 276:1494-1505). The remarkable target specificity of nanozymes is further consistent with the results that the negative controls showed no cleavage activity against either the HCV or AAT RNAs (FIG. 2). On the contrary, unbound RNase A nonspecifically degraded both RNA substrates into short fragments, which appeared as broad smear bands (FIG. 2). Together, these results demonstrate that, like the RISC machinery, the anti-HCV nanozyme was capable of cleaving its target RNAs in a sequence- and site-specific manner (FIG. 1).

Given the potential for RNase A degradation by proteinases in the cell or in vivo (Kelly, B. M., et al. European Journal of Cell Biology 1989, 48:71-78), the in vitro resistance of the anti-HCV nanozyme against proteinase K compared with particle-free RNase A was next examined (FIG. 2). RNase activity tests show that unbound RNase A lost its activity almost completely after 1 h incubation with proteinase K in a PBS buffer (pH 7.4) at 37° C. In contrast, nearly no measurable change was observed in the nanozyme activity after an identical proteinase K treatment (FIG. 2). The resistance to proteinase degradation was attributed to the fact that the RNase molecules on the nanozyme were protected by the densely packed oligonucleotides through steric hindrance (FIG. 1). The ability to resist proteinase degradation should enhance the stability of these nanozymes in the cell and in vivo (vide infra).

To examine the intracellular activity of the nanozyme against HCV replication, an HCV replicon cell culture system, a FL-Neo cell line, which is a stable human hepatoma Huh7-derived cell line (Randall, G., et al. P Natl Acad Sci USA 2003, 100:235-240) was used. This cell line harbors autonomously replicating genomic length genotype 1b HCV replicons and is an excellent system to evaluate anti-HCV agents in cell culture (Randall, G., et al. P Natl Acad Sci USA 2003, 100:235-240). The cellular uptake and cytotoxicity of anti-HCV nanozymes was first evaluated. The assay based on inductively coupled plasma mass spectrometry shows that the nanozymes were effectively internalized by cultured FL-Neo cells. Uptake was nearly proportional to the concentration of nanozymes added to the cell media at low concentrations; an average number of nanozymes found in each cell was (4.6±0.2)×104 at a concentration of 0.54 nM. Cell viability tests show that the nanozymes displayed no detectable toxicity to FL-Neo cells at concentrations ranging from 0.034 to 0.54 nM.

The intracellular activity of the anti-HCV nanozyme was then examined with respect to gene knockdown for suppressing the replication of HCV RNA. FL-Neo cells were treated once with the nanozyme (or a control) at varying concentrations, incubated at 37° C. for 72 h, and then harvested and processed for a viral RNA assay using a quantitative real-time reverse-transcription polymerase chain reaction (qRT-PCR), with the endogenous glyceraldehyde-3-phosphate dehydrogenase (GAPDH) gene as an internal standard. Results showed that the treatments using anti-HCV nanozymes, control nanozymes, RNase-NPs, DNA-NPs, or control DNA-NPs did not lead to a measurable change in the GAPDH-RNA levels in FL-Neo cells, indicating that these treatments did not induce toxicity effects on cell proliferation, which is in agreement with the results from our cell viability tests.

Figure 3A:
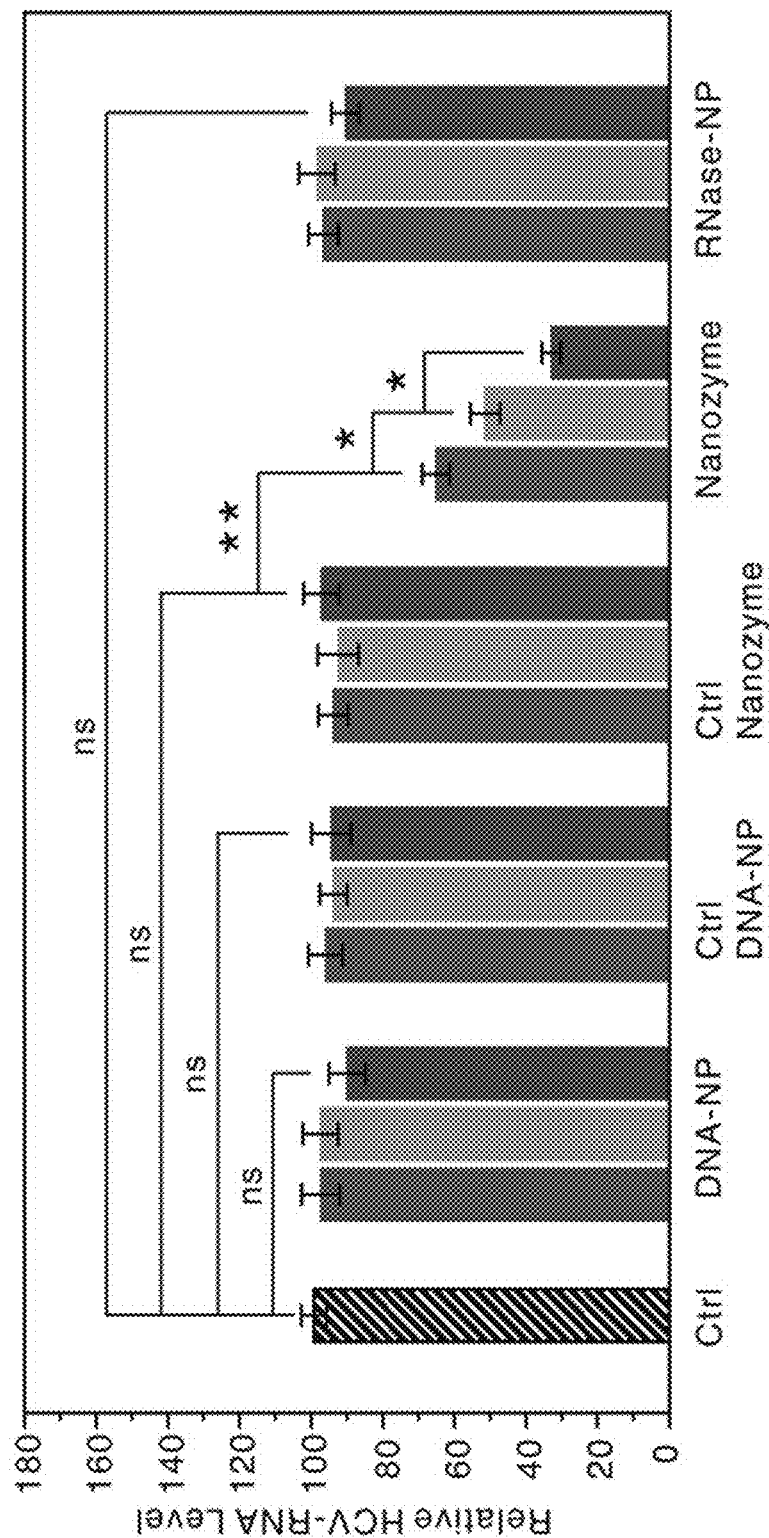
FIG. 3A to 3D show anti-HCV effects of the anti-HCV nanozyme in FL-Neo cells.

No measurable reduction in the HCV RNA levels was observed in the treatments using DNA-NPs at concentrations of 0.034, 0.14, and 0.54 nM (FIG. 3A). The inability of these conjugates to cause significant antisense effects on HCV replication is likely due to their low concentrations in our experiments (Rosi, N. L., et al. Science 2006, 312:1027-1030). In contrast, when treated respectively with the corresponding nanozyme dosages, HCV replication in the cells dramatically decreased, and the inhibitory effect was dose dependent (FIG. 3A). As additional controls, neither control nanozymes nor control DNA-NPs induced detectable antiviral effects (FIG. 3A), which further confirms that these nanozymes exhibit excellent intracellular target specificity.

In addition, the treatments with RNase-NPs did not lead to measurable effects on HCV RNA replication. This result is likely associated with the RNase deactivation/inhibition by intracellular proteinases and ribonuclease inhibitors (Kelly, B. M., et al. European Journal of Cell Biology 1989, 48:71-78; Kobe, B., et al. J Mol Biol 1996, 264:1028-1043), and it indicates that the densely packed oligonucleotides are important for the nanozyme activity in cell and in vivo (vide supra). Moreover, the nanozyme-induced antivirus effects observed herein might also be caused by IFN activation (Marques, J. T., et al. Nat Biotechnol 2005, 23:1399-1405). To evaluate this possibility, the expression of gene 6-16 (G1P3), a downstream gene in the IFN signaling pathway (Zhu, H. Z., et al. Hepatology 2003, 37:1180-1188) was examined. No changes were observed in the mRNA level of this gene in FL-Neo cells treated with anti-HCV nanozymes at the concentrations tested, and this result essentially rules out the possibility of IFN pathway induction by these nanoparticles (Zhu, H. Z., et al. Hepatology 2003, 37:1180-1188).

Figure 3B:
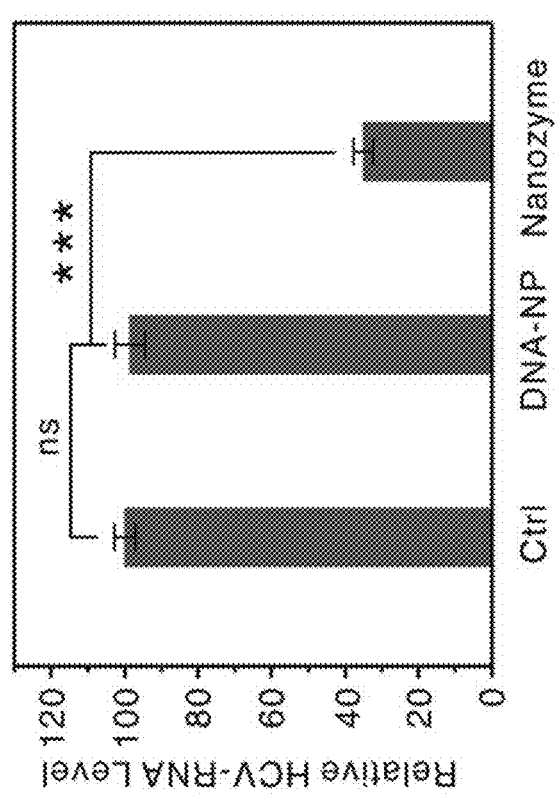

To further assess the intracellular antiviral activity of the anti-HCV nanozyme, whether the nanozyme-mediated HCV RNA reduction is associated with suppression of viral protein synthesis was examined. The non-structured 5A (NS5A) protein of HCV-which plays key roles in both viral RNA replication and modulation of the physiology of the host cell—was used to evaluate HCV protein levels in FL-Neo cells. In a typical experiment, FL-Neo cells were treated with the anti-HCV nanozyme (0.068 nM) or a control on days 1, 3, and 5, and then harvested on day 7. The results from qRT-PCR analyses show that the nanozyme treatment resulted in a 65% decrease in HCV RNA levels in FL-Neo cells, whereas the treatment using the same amount of DNA-NPs did not induce measurable effects on HCV RNA replication (FIG. 3B).

Figure 3C:
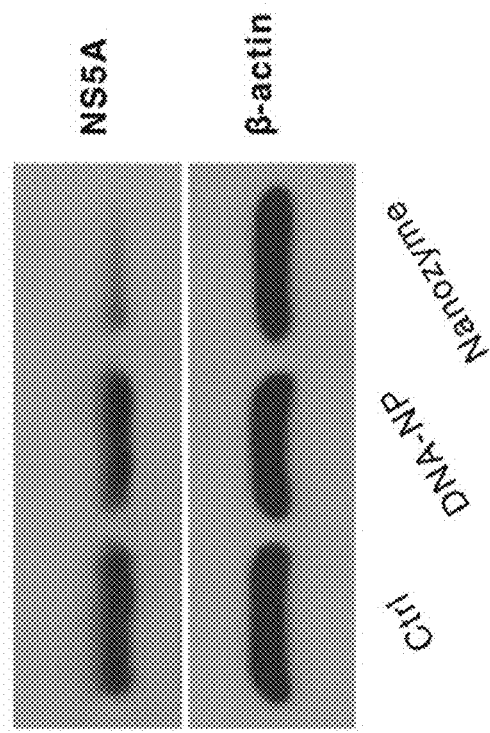
Figure 3D:
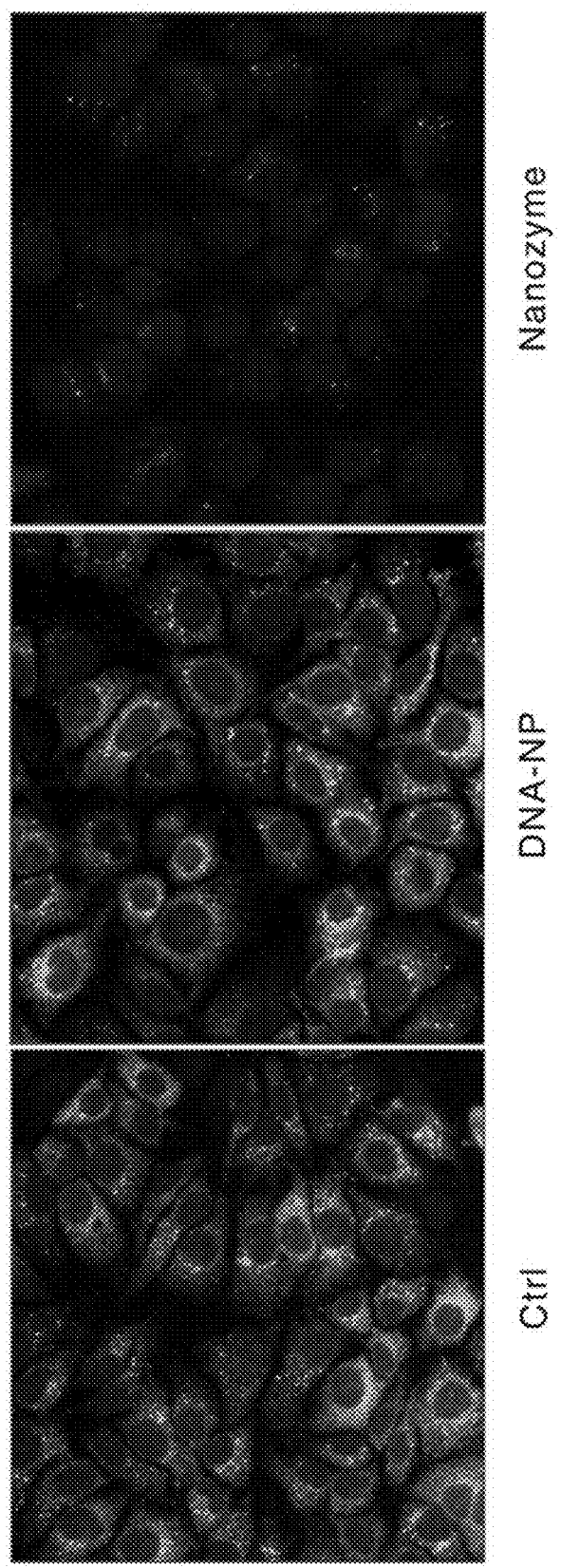

Western blot analyses show fairly consistent results regarding the protein level: barely any effect was observed in the FL-Neo cells treated with DNA-NPs, whereas the FL-Neo cells displayed a significant decrease in NS5A protein level of ~75% upon nanozyme treatment (FIG. 3C). NS5A protein reductions slightly exceeded the reduction levels obtained from HCV RNA, and this could be due to post-transcriptional mechanisms that have been observed previously (Kanda, T., et al. J Virol 2007, 81:669-676). In addition, the results from these ensemble measurements are consistent with those from single-cell level observations on the basis of fluorescent immunohistochemical staining for NS5A protein (FIG. 3D). After the nanozyme treatment, more than 99% of FL-Neo cells displayed a significant decrease in the level of NS5A protein expression when compared to the control treatments (FIG. 3D). Altogether, these results unambiguously demonstrate that the anti-HCV nanozyme was capable of inducing an HCV gene knockdown in both the RNA and protein levels.

Example 2: Nanozyme Design Rationale

Generally speaking, a nanozyme's enzymatic activity is determined by (1) the distance between the oligonucleotide recognition site and its RNase's active site, (2) the orientation of the RNase's active site, and (3) the number of RNase A. A nanozyme's target selectivity is determined by the surface packing density of oligonucleotides. This is because the nanozyme's selectivity is substantiated by the cooperative coupling between the RNase and DNA-oligonucleotide components of the nanozyme. On one hand, the access of non-complementary RNA to the nanozyme-bearing RNase molecules is blocked by the densely packed oligonucleotides through steric hindrance and repulsive Coulombic interactions. On the other hand, these DNA oligonucleotides can also bind to target RNA via base pairing and bring them to the RNase molecules on the nanozyme, resulting in the endonucleolytic cleavage of these RNA into two fragments at positions close to the binding site (FIGS. 1 and 2A). Therefore, the DNA oligonucleotide surface density should be critical for RNA target specificity in nanozymes. Indeed, the RNase activity assay shows that the anti-HCV nanozymes with a low oligonucleotide surface coverage (i.e., NZ-Ls) did not exhibit target specificity but did cut both the HCV and AAT RNA in a sequence non-specific manner (FIGS. 1 and 2).

Preparation of nanozymes with dense oligonucleotide packing required a large excess of alkylthiol-functionalized oligonucleotides. However, the weakly-bound wild-type RNase A can be easily removed from the surface of the nanoparticles by alkylthiol-functionalized oligonucleotides. The nanozyme synthesis process is under a very unstable kinetic control. As a result, it is very difficult to reproducibly prepare nanozymes possessing densely-packed oligonucleotides around the RNase A with a high synthetic yield. In addition, nanozymes' enzymatic activity decreases during relatively-long term room temperature storage because of the loss of the weakly-bound RNase A. These two drawbacks have significantly slowed the use of nanozymes in fundamental genomic function studies and their use as therapeutic agents for clinical trials.

To overcome these difficulties, a recombinant RNase A is developed-choosing two well-known cysteine-substituted mutants as models—to construct a new generation of nanozymes (Abel, R. L., et al. Anal Biochem 2002, 306: 100-107; Rutkoski, T. J., et al. Cancer Biol Ther 2011, 12:208-214). These mutants are covalently functionalized with a length-tunable multi-thiol tether at the cysteine site, and then loaded onto gold particles through multiple gold-sulfur bonds. This new RNase A loading mechanism is site specific, and it allows high-density loading of alkylthiol modified DNA oligonucleotides, which would result in successful preparation of nanozymes with high target selectivity in a very controllable fashion.

Figure 4:
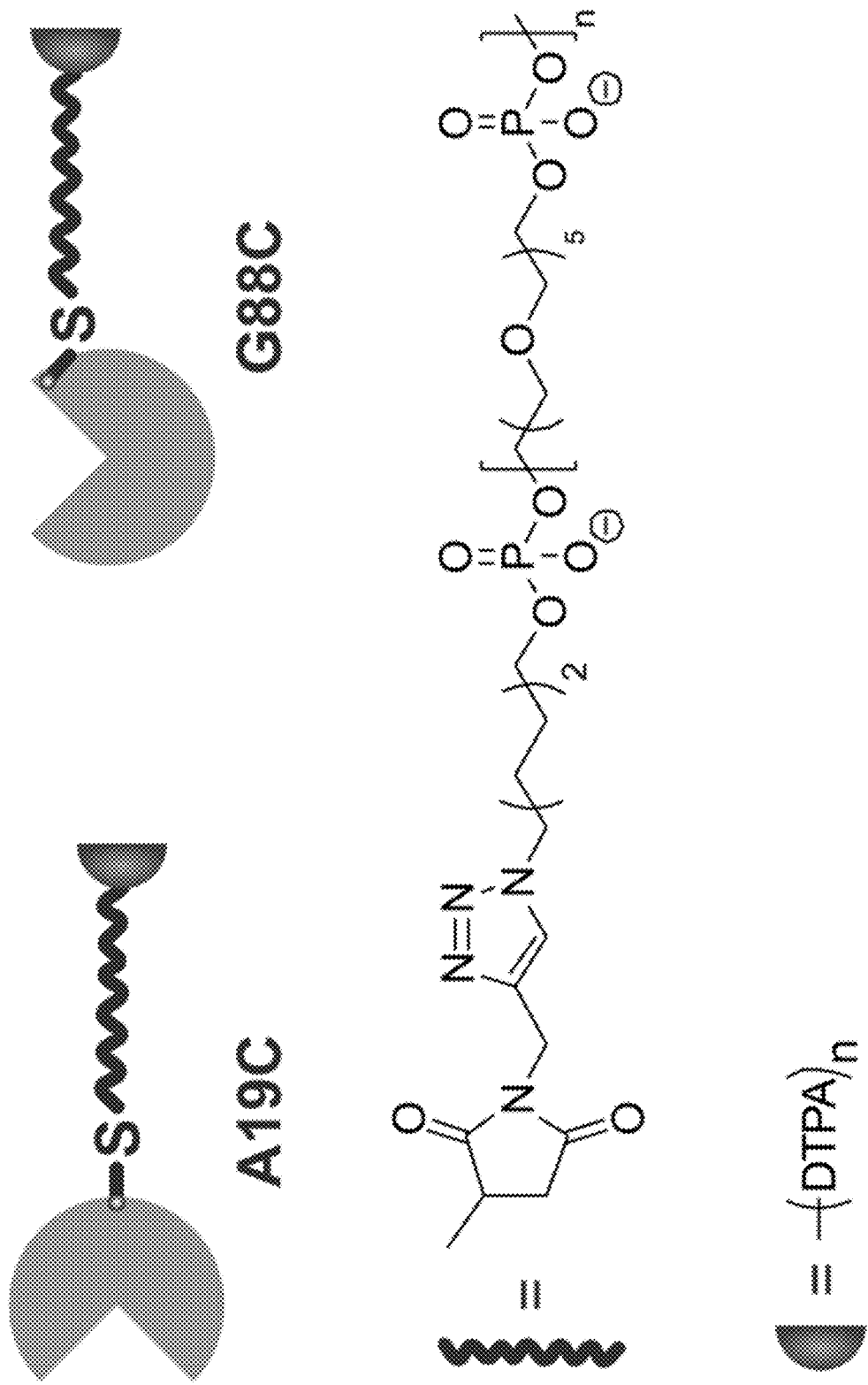
FIG. 4 is a schematic representation for the designing of multi-thiol functionalized RNase A. The RNase A is mutated at positon Ala19 (A19C) or Gly88 (G88C) and linked to a DTPA (dithiol anchor) terminated PEG spacer via click chemistry.

The reaction kinetics of an ideal nanozyme (NZ) and its target RNA (i.e., substrate, S) can be written as Eq. 1. Because the turnover number ($k_{cat}$) of the two chosen RNase A mutants is about six orders of magnitude larger than the rate constants $k_1$ and $k_2$, this three-step enzymatic reaction can be simplified into a three-step consecutive reaction. Its rate law is shown in Eq. 2, which can be further reduced to Eq. 3. This rate law shows that the product rate of an ideal nanozyme is only determined by the rate constants of DNA/RNA hybridization ($k_1$) and dehybridization ($k_2$). When the nanozyme only binds to its substrate at a single site, the high binding strength required by the high target selectivity leads to smaller rate constants $k_1$ and $k_2$, and thus a slower overall nanozyme reaction rate. To promote this reaction, $k_1$ and $k_2$ be increased via a two-site target binding mechanism. When two binding sites are in suitable close proximity, the overall binding strength stays high due to the cooperative effect between the two binding sites, which ensures the high target selectivity for the nanozyme. After being cut, the loss of binding cooperativity can lead to a significantly larger $k_2$, and thus an overall higher nanozyme reaction rate. Accordingly, nanozymes are prepared with double-sequenced oligonucleotide capturers, which can bind to specific RNA targets at two close proximity sites (FIG. 4).

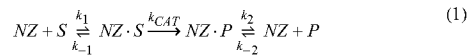

$$NZ + S \underset{k_{-1}}{\overset{k_1}{\rightleftharpoons}} NZ \cdot S \xrightarrow{k_{CAT}} NZ \cdot P \underset{k_{-2}}{\overset{k_2}{\rightleftharpoons}} NZ + P \quad (1)$$

$$[P] = [S_0]\left\{1 - \frac{k_{CAT} \cdot k_2 \cdot e^{-k_1 \cdot t}}{(k_{CAT} - k_1)(k_2 - k_1)} - \frac{k_1 \cdot k_2 \cdot e^{-k_{CAT} \cdot t}}{(k_{CAT} - k_1)(k_{CAT} - k_2)} + \frac{k_1 \cdot k_{CAT} \cdot e^{-k_2 \cdot t}}{(k_2 - k_1)(k_{CAT} - k_2)}\right\} \quad (2)$$

$$\approx [S_0]\left\{1 - \frac{k_2}{k_2 - k_1}e^{-k_3 \cdot t} + \frac{k_1}{k_2 - k_1}e^{-k_2 \cdot t}\right\} \quad (3)$$

To further maximize the nanozyme's target selectivity and enzymatic activity for efficient cleavage of target RNA, nanozymes are prepared with two- and multiple-branched dendron structures, which can further increase the local density of single-stranded capture oligonucleotides around RNase A on the surface of nanozymes.

Example 3: Preparation of Recombinant RNase A with a Multi-Thiol Modified Tether Production of RNase A Mutant.

RNase A mutants for functionalization are produced. Because of the well-established production procedures and relatively high enzymatic activities as compared with the wild type RNase A (Futami, J., et al. Curr Pharm Biotechno 2008, 9:180-184; Rutkoski, T. J., et al. Curr Pharm Biotechno 2008, 9:185-199; Leland, P. A., et al. P Natl Acad Sci USA 1998, 95:10407-10412), two mutants were chosen as model enzymes for constructing the nanozyme, A19C and G88C (Abel, R. L., et al. Anal Biochem 2002, 306:100-107; Rutkoski, T. J., et al. Cancer Biol Ther 2011, 12:208-214), in which Ala19 and Gly88 are mutated into cysteine, respectively. Ala19 is on the back of the active site, while Gly88 is close to the active site (FIG. 4). The thiol groups in A19C and G88C enable precise multi-thiol functionalization at these two locations.

According to well-established procedures, these two mutants are expressed using pET22b(+)/pET27b(+) plasmid and *Escherichia coli* (*E. coli*) BL21(DE3) cells (Rutkoski, T. J., et al. Cancer Biol Ther 2011, 12:208-214; Delcardayre, S. B., et al. Protein Eng 1995, 8:261-273). All the solutions used for dissolving inclusion bodies containing mutants and buffers for enzyme refolding will be purged with $N_2$ to prevent the possible oxidation of free thiol groups. After purification with gel filtration chromatography, 5,5'-dithiobis(2-nitrobenzoic acid) is used for thiol protection and the protein is stored at −80° C. after further cation exchange chromatography (Abel, R. L., et al. Anal Biochem 2002, 306:100-107; Johnson, R. J., et al. Biochemistry-Us 2007, 46:10308-10316; D'Avino, C., et al. Protein Eng Des Sel 2014, 27:83-88).

Preparation of Multi-Thiol Functionalized RNase A

A multi-thiol functionalized RNase A is produced. As shown FIG. 4, multi-thiol functionalized RNase A is prepared as follows. The mutant enzyme is firstly reacted with propargyl-maleimide to introduce an alkynyl group. Meanwhile the PEG tether is synthesized in a solid-state oligonucleotide synthesizer using 3'-dithiol serinol CPG, spacer phosphoramidite 18 and 5'-bromohexyl phosphoramidite, followed by converting the 5'-bromide into an azide using sodium azide. Finally, the multi-thiol terminated PEG is linked to alkynyl-functionalized RNase A via "click" chemistry. All the reagents above are commercially available and reactions are easy and robust. The prepared multi-thiol functionalized RNase A is purified by cation exchange chromatography and tested on its enzymatic activity using a small fluorescence RNA substrate 6-FAM-dArUdAdA-6-TAMRA, following established procedures (Rutkoski, T. J., et al. Cancer Biol Ther 2011, 12:208-214).

Example 4: Preparation and Characterization of Nanozymes Formed with Single-Sequenced Capturers as Well as Branched Double-Sequenced Capturers Preparation of RNA Molecular Beacon for Nanozyme Enzymatic Test An RNA molecular beacon for nanozyme enzymatic test was constructed. Based on theoretical simulations (Tyagi, S., et al. Nat Biotechnol 1996, 14:303-308; Rizzo, J., et al. Mol Cell Probe 2002, 16:277-283; Wang, K. M., et al. Angew Chem Int Edit 2009, 48:856-870), nucleotides 322 to 370 in 5'-untranslated genome (5' UTR) of HCV genome was selected for constructing the molecular beacon (Table 1). Seven additional nucleotides are added to construct the stem of the designed molecular beacon. Moreover, a control beacon with two oligonucleotides mutated is also designed (Tsourkas, A., et al. Nucleic Acids Res 2002, 30:5168-5174). Both molecular beacons are synthesized using a solid-state oligonucleotide synthesizer and commercially available reagents.

TABLE 1

Sequence design of RNA molecular/control beacon and capturer/control strands on NZ.

| Name | Sequence |
|---|---|
| Molecular beacon | 5' Cy3-GGU-CUC-GUA-GAC-CGU-GCA-CCA-UGA-GCA-CAC-UUC-CAA-AAC-CCC-AAA-GAA-AAc-gag-acc-Dabcyl 3' (SEQ ID NO: 1 for underlined portion) |
| Control beacon | 5' Cy3-GGU-CUG-GUA-UAC-CGU-GCA-CCA-UGA-GCA-CAC-UUC-CAA-AAC-CCC-AAG-GAA-AAc-gag-acc-Dabcyl 3' (SEQ ID NO: 2 for underlined portion) |
| Nanozyme IIa capturer 1 | 3' HS-(CH$_2$)$_3$-spacer-CCA-GAG-CAT-CTG-GCA-CGT 5' (SEQ ID NO: 3 for underlined portion) |
| Nanozyme IIa control I | 3' HS-(CH$_2$)$_3$-spacer-CCA-GAC-CAT-ATG-GCA-CGT 5' (SEQ ID NO: 4 for underlined portion) |
| Nanozyme IIa capturer 2 | 3' HS-(CH$_2$)$_3$-spacer-CCA-GAG-CAT-CTG-GCA 5' (SEQ ID NO: 5 for underlined portion) |
| Nanozyme IIa capturer 3 | 3' HS-(CH$_2$)$_3$-spacer-CCA-GAG-CAT-CTG 5' (SEQ ID NO: 6 for underlined portion) |
| Nanozyme IIb capturer | C$_1$: 3' spacer-CCA-GAG-CAT-CTG 5' (SEQ ID NO: 7 for underlined portion)<br>C$_2$: 3' spacer-TTT-CTT-T 5' |
| Nanozyme IIb control | C$_1$: 3' spacer-CCA-GAC-CAT-ATG 5' (SEQ ID NO: 8 for underlined portion)<br>C$_2$: 3' spacer-TTC-CTT-T 5' |
| Blocker | 5' Cy3-GGU-CUC-GUA-GAC-CGU-GCA 3' (SEQ ID NO: 9 for underlined portion) |
| Switch | 5' Cy3-GUA-GAC-CGU-GCA-AAA-AAA-AAA-AAA-AAA-AAA-AA 3' (SEQ ID NO: 10 for underlined portion) |
| Activator | 5' TTT-TTT-TTT-TTT-TTT-TTT-TTT-GCA-CGG-TCT-AC 3' (SEQ ID NO: 11 for underlined portion) |

For the designed molecular beacon to be functional in nanozyme testing, its fluorescence on/off is tested with free capturer strands that are complementary to the beginning 18 nucleotides in the 5' end of the molecular beacon. Without free capturer strands, the annealed molecular beacon should give low florescence signals, while with free capturer strands, the loop should be open and the fluorescence signal should be significantly increased due to the separation of fluorophore and quencher (Sokol, D. L., et al. P Natl Acad Sci USA 1998, 95:11538-11543; Tyagi, S., et al. Nat Biotechnol 1998, 16:49-53; Vargas, D. Y., et al. P Natl Acad Sci USA 2005, 102:17008-17013; Wang, L., et al. J Am Chem Soc 2005, 127:15664-15665).

Preparation and Characterization of Nanozymes Formed with Single-Sequenced Capturers (Nanozyme IIa)

Figure 5A:
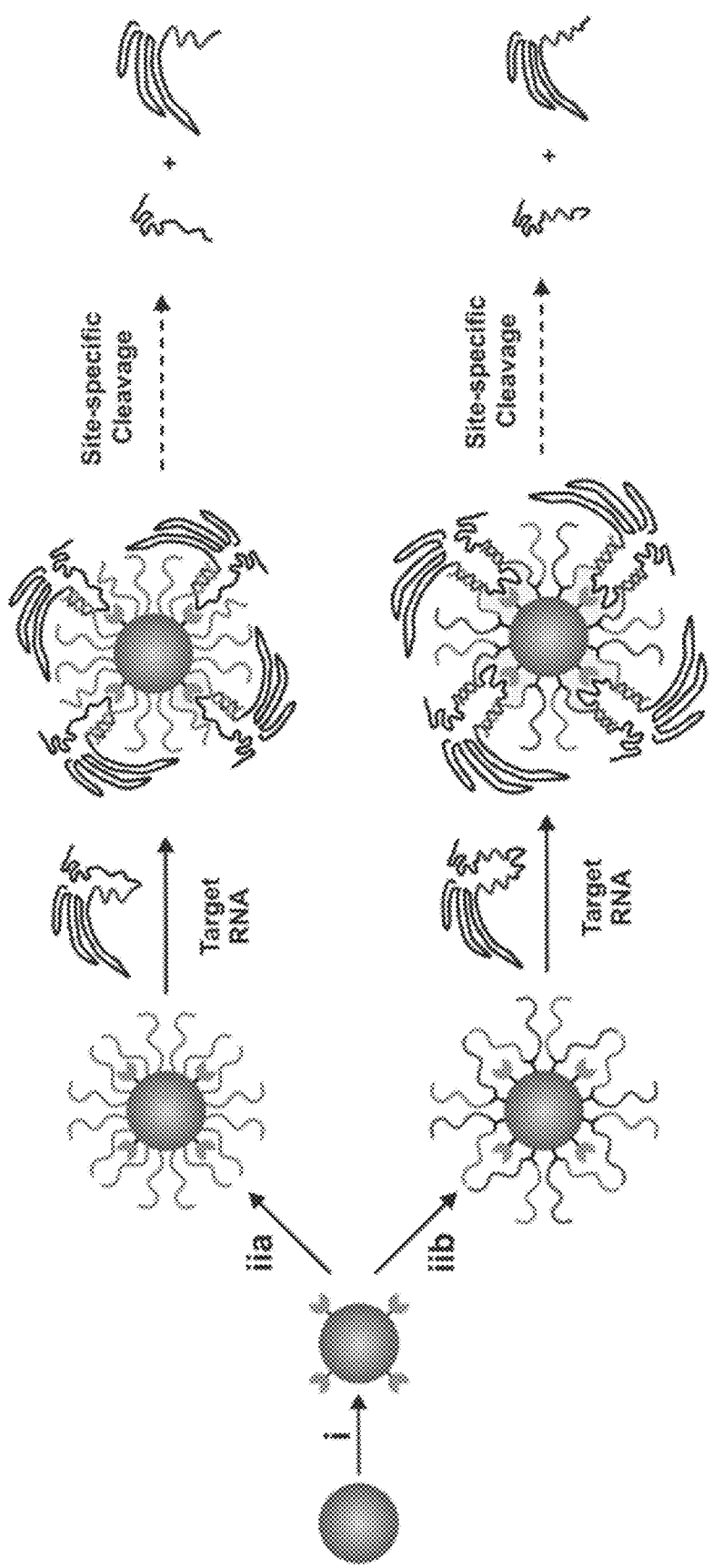
FIG. 5A is a schematic representation describing the synthesis procedures of nanozyme IIa (single capturer strand, top) and IIb (double capturer strands, bottom).
Figures 5B, 5C:
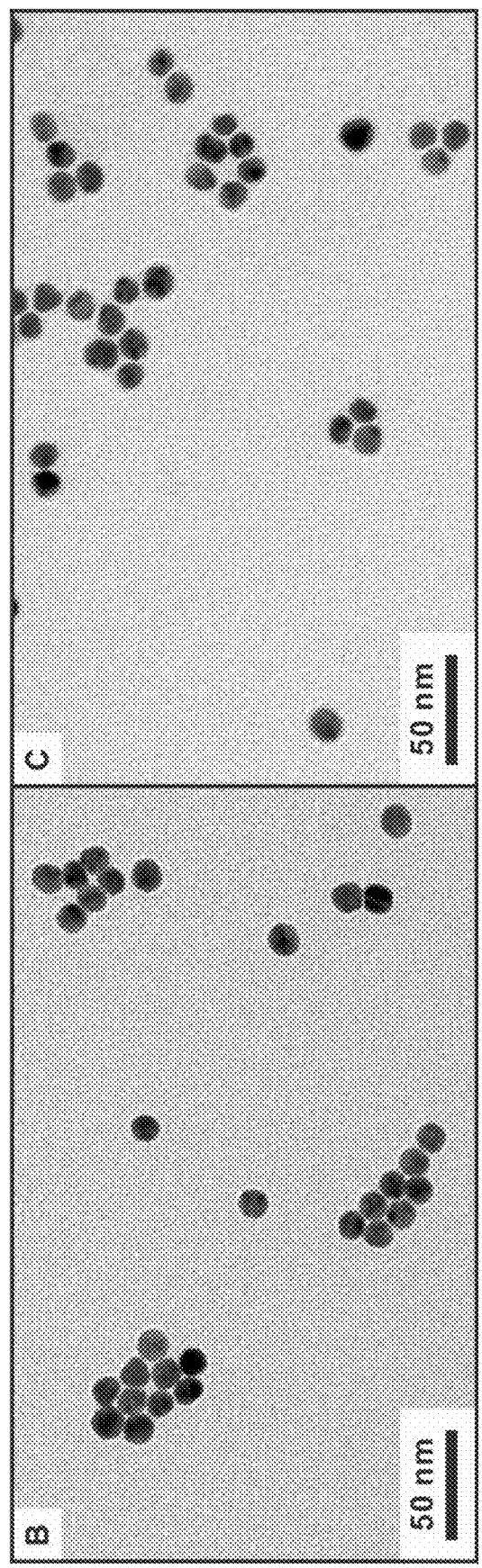
FIGS. 5B and 5C show typical transmission electron microscope images of Nanozyme IIa (FIG. 5B) and Nanozyme Iib (FIG. 5C).
Figure 6:
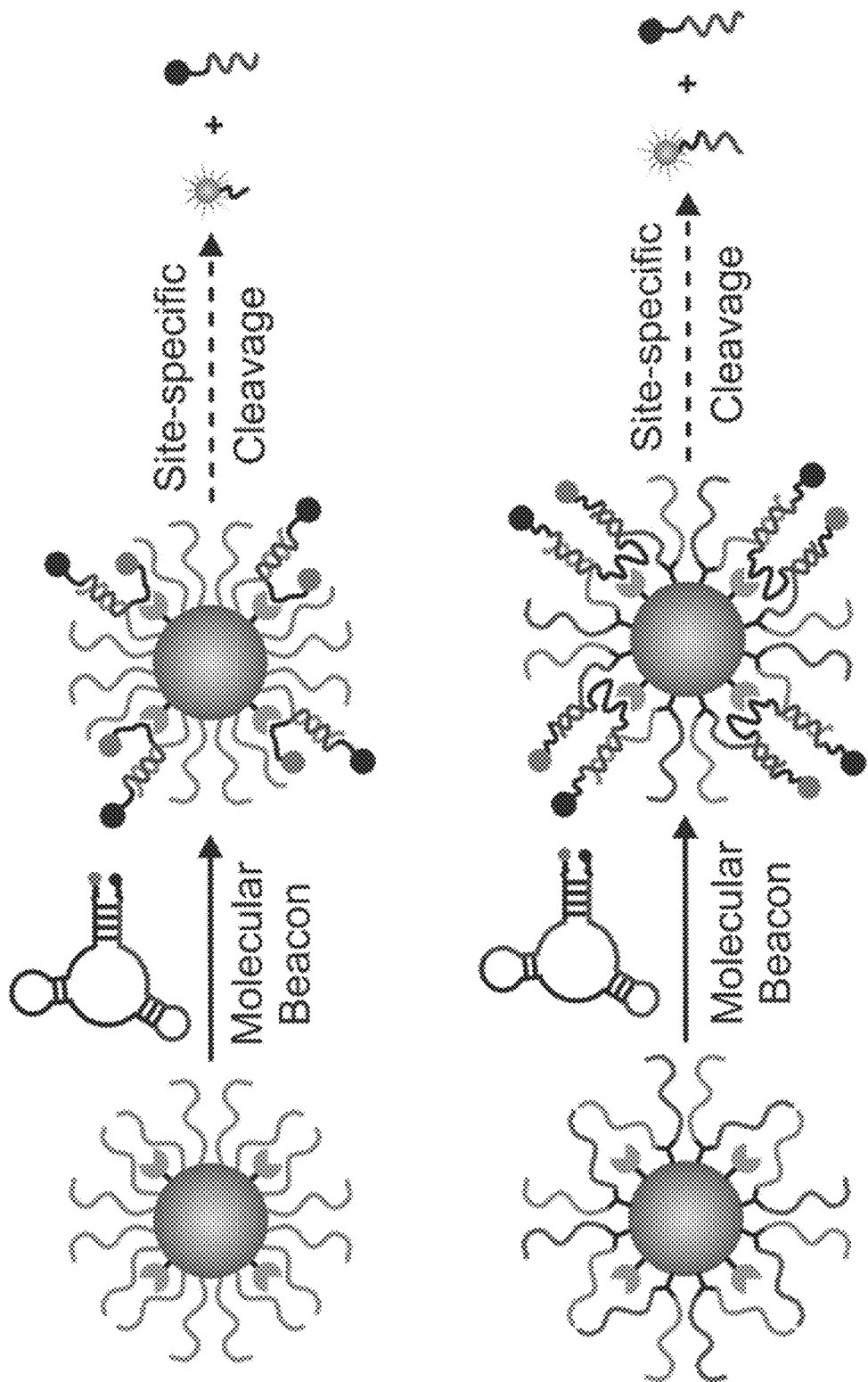
FIG. 6 is a schematic representation of enzyme kinetics testing for nanozyme IIa (single capturer strand) and IIb (double capturer strands) using RNA molecular beacon.

Nanozyme IIa with single-sequenced capturers is prepared and characterized. Generally, nanozyme IIa is prepared via a two-step synthesis (Wang, Z. L., et al. P Natl Acad Sci USA 2012, 109:12387-12392) (FIG. 5). First of all, multi-thiol functionalized RNase A is loaded onto Au nanoparticles with various loading densities to optimize the activity. Secondly, single-sequenced capturers designed and synthesized based on the molecular beacon are densely loaded onto the surface of Au nanoparticles. The enzymatic activity of nanozyme is tested using the designed molecular beacon (FIG. 6).

During the first stage of RNase A loading, various enzyme/Au nanoparticle ratios (enzyme:Au=1 to 10) are carried out and the corresponding enzymatic activity of RNase-nanoparticle (RNase NP) is tested using the same method mentioned above and compared with that of free multi-thiol functionalized RNase A, RNase A mutant before multi-thiol functionalization, and wild type RNase A. Due to the conformational constraint and lack of freedom, RNase-NP may exhibit significantly lowered enzymatic activity. Under such circumstances, the length of PEG tether between RNase A and thiol anchor is increased to render the enzyme more conformationally free so as to improve its enzymatic activity. Considering the functionalization position of two mutants, A19C may show better activity with a relatively short PEG tether since its catalytic pocket will be exposed toward the outside (Messmore, J. M., et al. J Am Chem Soc 1995, 117:8057-8060) (FIG. 4).

High oligonucleotide loading density is critical for a nanozyme's selectivity. Therefore, during the second step of NZ preparation, the capture strand loading density on RNase-NP is maximized with a large strand/Au nanoparticle ratio and high NaC concentration in salt aging. Once finished, prepared nanozymes are dissolved by KCN solution to remove the Au nanoparticle backbone, and RNase and oligonucleotides per Au nanoparticle are quantified as previously described (Wang, Z. L., et al. P Natl Acad Sci USA 2012, 109:12387-12392) to ensure that high density capturer strand loading is achieved.

Starting from low RNase A loading, evenly distributed RNase A on Au nanoparticle is achieved, thus it is evenly covered by densely loaded oligonucleotides. Accordingly, the nanozyme has high selectivity discriminating between targets and control molecular beacon. If no selectivity is observed, it can be due the insufficient coverage of enzyme molecule because of relatively short spacers in capturer strands; or if nanozymes show no enzymatic activity while sufficient RNase A loading is confirmed, the too-long spacer's length in the capturer strand may be the cause since it prevents the bound molecular beacon to be cut by the enzyme. Under such circumstances, the length of spacer in capturer strand and RNase A is optimized.

Moreover, to further optimize the nanozyme's selectivity and activity, the enzyme kinetics is studied using a molecular beacon as previously described (Kelemen, B. R., et al. Nucleic Acids Res 1999, 27:3696-3701). By fitting the experimental data into the Equation 3, kinetic parameters can be obtained and used in further tailoring nanozyme's activity and selectivity.

Preparation and Characterization of Nanozymes Formed with Branched Double-Sequenced Capturers (Nanozyme IIb)

The nanozyme's enzyme kinetic efficiency are improved by facilitating the product leaving after cleavage. Double capturer strand DNA is synthesized via a solid state oligonucleotide synthesizer using the asymmetrical doubler (5-Me-dC brancher phosphoramidite) following manufacturer recommendations, and the two sequences are designed to capture the molecular beacon as well (Southern, E. M., et al. Nucleic Acids Res 1994, 22:1368-1373; Horn, T., et al. Nucleic Acids Res 1997, 25:4842-4849; Horn, T., et al. Nucleic Acids Res 1997, 25:4835-4841).

Nanozyme IIb is synthesized based on the optimized enzyme loading number and spacers' length (FIG. 5), and enzymatic testing experiments are carried out following the same methods as nanozyme IIa. With such double capturer design, it is expected that nanozyme IIb may present much better enzyme kinetic efficiency then nanozyme IIa.

In Vitro Evaluation of Nanozyme IIa and IIb Activities

Nanozyme II's enzymatic activity and selectivity with large HCV RNA substrates and is tested and its effect on target cellular mRNA level and corresponding protein expression is evaluated. Nanozyme's selective cleavage toward target HCV and control RNA substrate is evaluated using gel electrophoresis, following previous procedures. Meanwhile, nanozyme's effect on cellular mRNA level is quantified using quantitative real-time polymerase chain reaction (qRT-PCR). As for protein expression evaluation, immunostaining is used for single cell protein level testing and Western blotting is used to assess the average level among all cells. All in vitro experiment follow previous procedures (Wang, Z. L., et al. P Natl Acad Sci USA 2012, 109:12387-12392).

Example 5: Preparation and Characterization of Nanozymes Formed with Unibodies of RNase A and DNA Dendrons (Nanozyme IIIa and IIIb)

This Example focuses on preparation and characterization of nanozymes composed of unibodies that contain six branches of capturer strands (single-sequenced capturers, IIA, or double-sequenced capturers, IIIb) and one mutated RNase A. Such design overcomes the possible uneven distribution of RNase A in nanozyme II preparation and further increase the capturer strand density surround RNase A, which is already discussed in Rationale.

Unibody Synthesis

Figure 7:
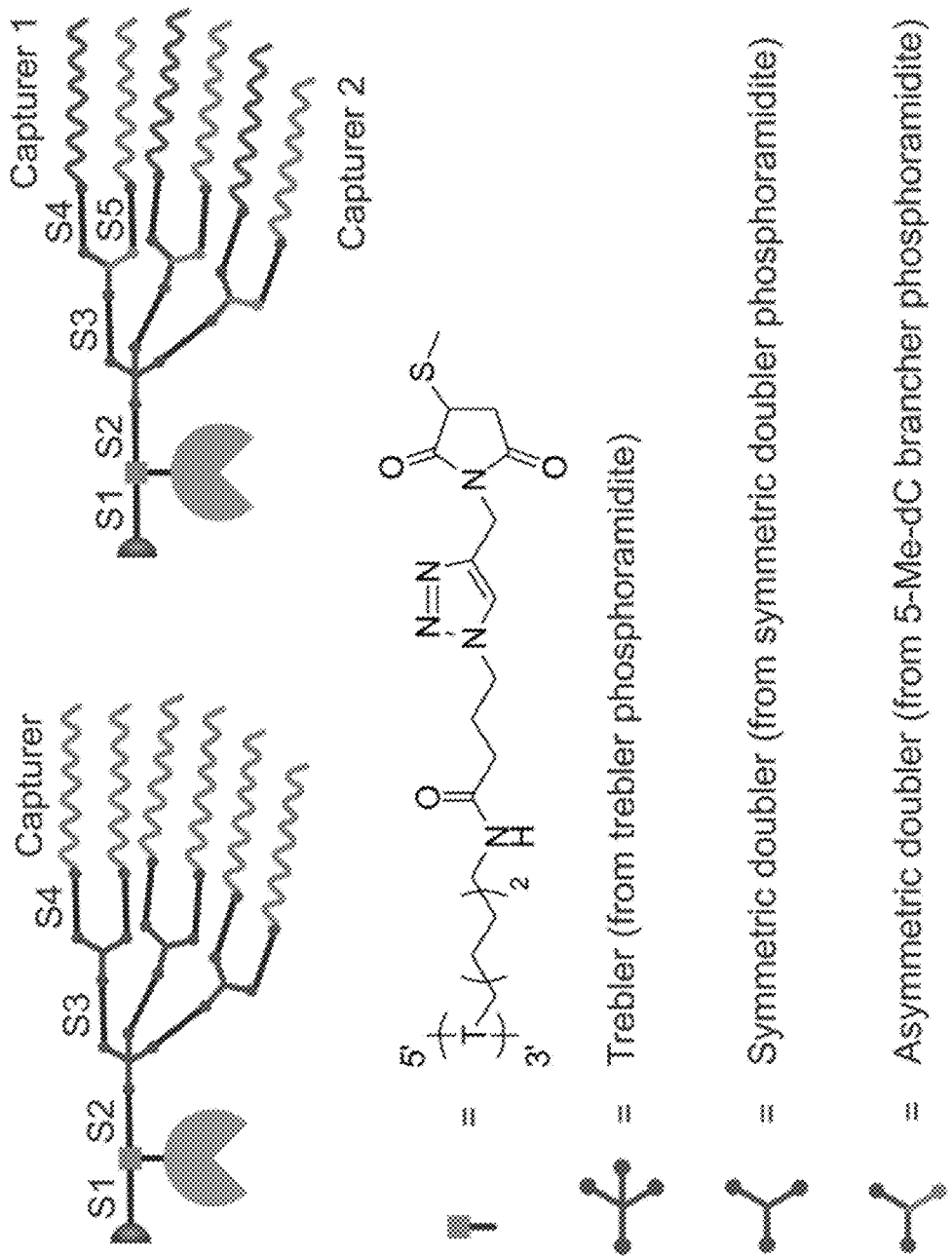
FIG. 7 is a schematic representation describing the design of unibody for nanozyme IIIa and IIIb. A single unibody contains six branches of capturer strands, either single (for nanozyme IIIa) or double type (for nanozyme IIIb), and one mutated RNase A, either A19C or G88C. All the branching reagents listed are commercially available from Glen Research. S stands for spacer.

Generally, the first step of unibody synthesis involves synthesizing six branched capturer strands dendron (Southern, E. M., et al. Genomics 1992, 13:1008-1017; Whitesides, G. M., et al. Science 1991, 254:1312-1319) using Trebler, symmetric/assymetric doubler phosphoramidite (Boussif, O., et al. P Natl Acad Sci USA 1995, 92:7297-7301; Jansen, J. F. G. A., et al. Science 1994, 266:1226-1229; Horn, T., et al. Nucleic Acids Res 1989, 17:6959-6967; Shchepinov, I. S., et al. Bioorg Khim+ 1998, 24:794-797; Shchepinov, M. S., et al. Nucleic Acids Res 1997, 25:4447-4454) (for single-sequenced and double-sequenced unibody, respectively, FIG. 7). All these branching reagents are commercially available and the synthesis is carried out using solid state oligonucleotide synthesizer following manufacturer's procedures. The synthesized dendron is characterized by MALDI-TOF to ensure the structural integrity. The RNase A is linked to the stem of the capturer dendron via a maleimide-thiol reaction, N-hydroxysuccinimide-amine reaction, and "click" chemistry. Finally, the unibody is characterized again with MALDI-TOF to ensure the successful enzyme cross-linking, and its enzymatic activity is tested with the same method mentioned before (C1.2).

Nanozyme IIIa and IIb Preparation and Enzymatic Testing

Figure 8:
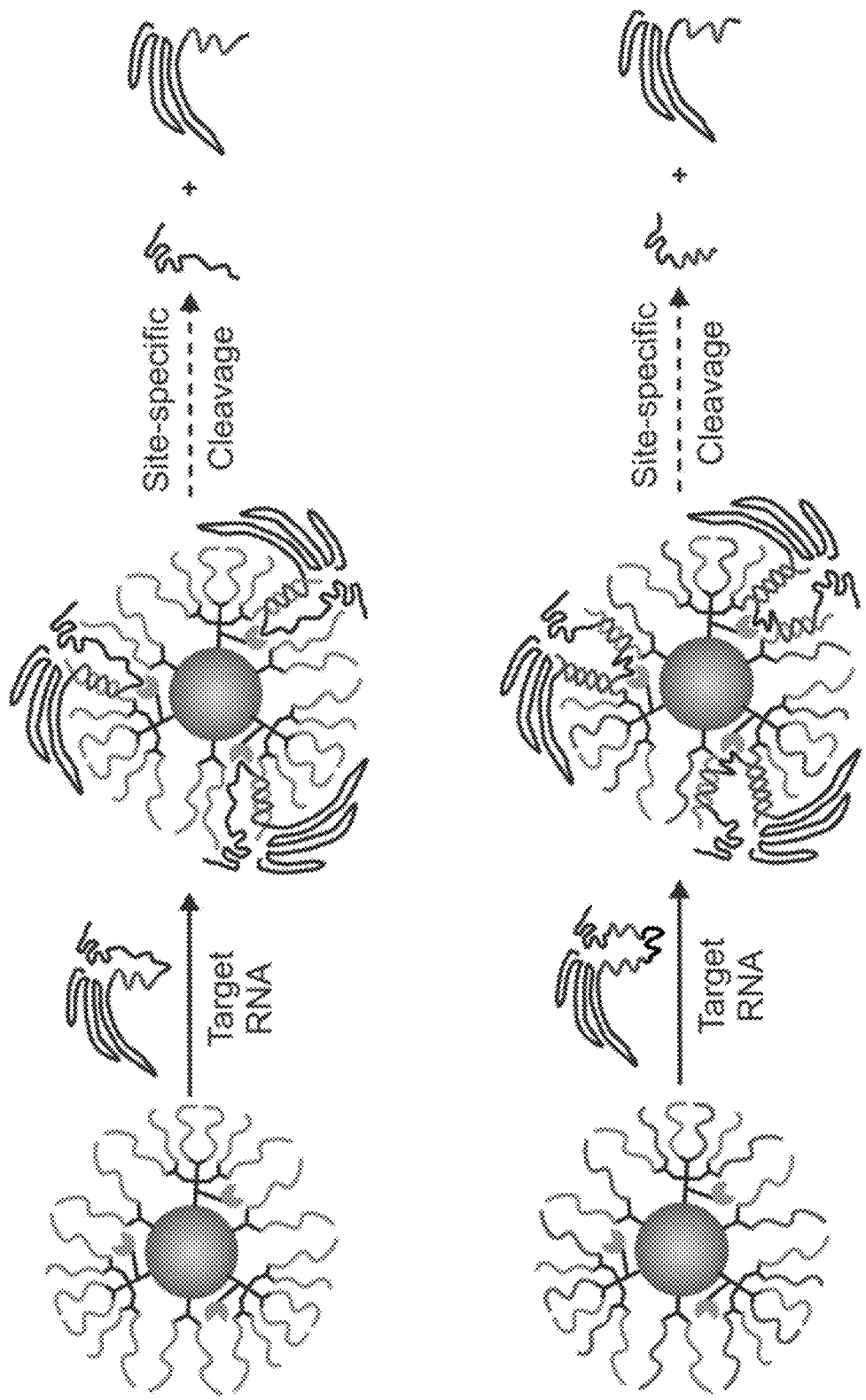
FIG. 8 is a schematic representation describing the design and function of a nanozyme IIIa (top) and IIIb (bottom).

Nanozyme IIIa or IIIb are prepared by loading single-sequenced or double sequenced unibodies onto gold nanoparticles under similar conditions as those for preparing nanozyme IIa and IIb. The selectivity and activity of nanozyme IIIa and IIIb is characterized in a similar way as mentioned above. To optimize the nanozyme's enzymatic activity and selectivity, the lengths of different spacers in DNA dendron and tether between RNase A and DNA dendron (FIG. 7) is tuned, and double capturers, either single type or double type, are loaded to fill the possible gap between unibodies on Au nanoparticle surface if necessary (FIG. 8).

In Vitro Evaluation of Nanozyme IIIa and IIb Activities

Nanozyme IIIa and IIIb is tested by similar methods as above, with their selective cleavage toward target HCV and control RNA substrate (FIG. 8) evaluated via gel electrophoresis, and in cellular gene expression regulation effect assessed by qRT-PCR, immunostaining and western blotting (Wang, Z. L., et al. P Natl Acad Sci USA 2012, 109:12387-12392).

Example 6: Preparation and Characterization of Nanozymes with an On-Off Switch

Figure 9:
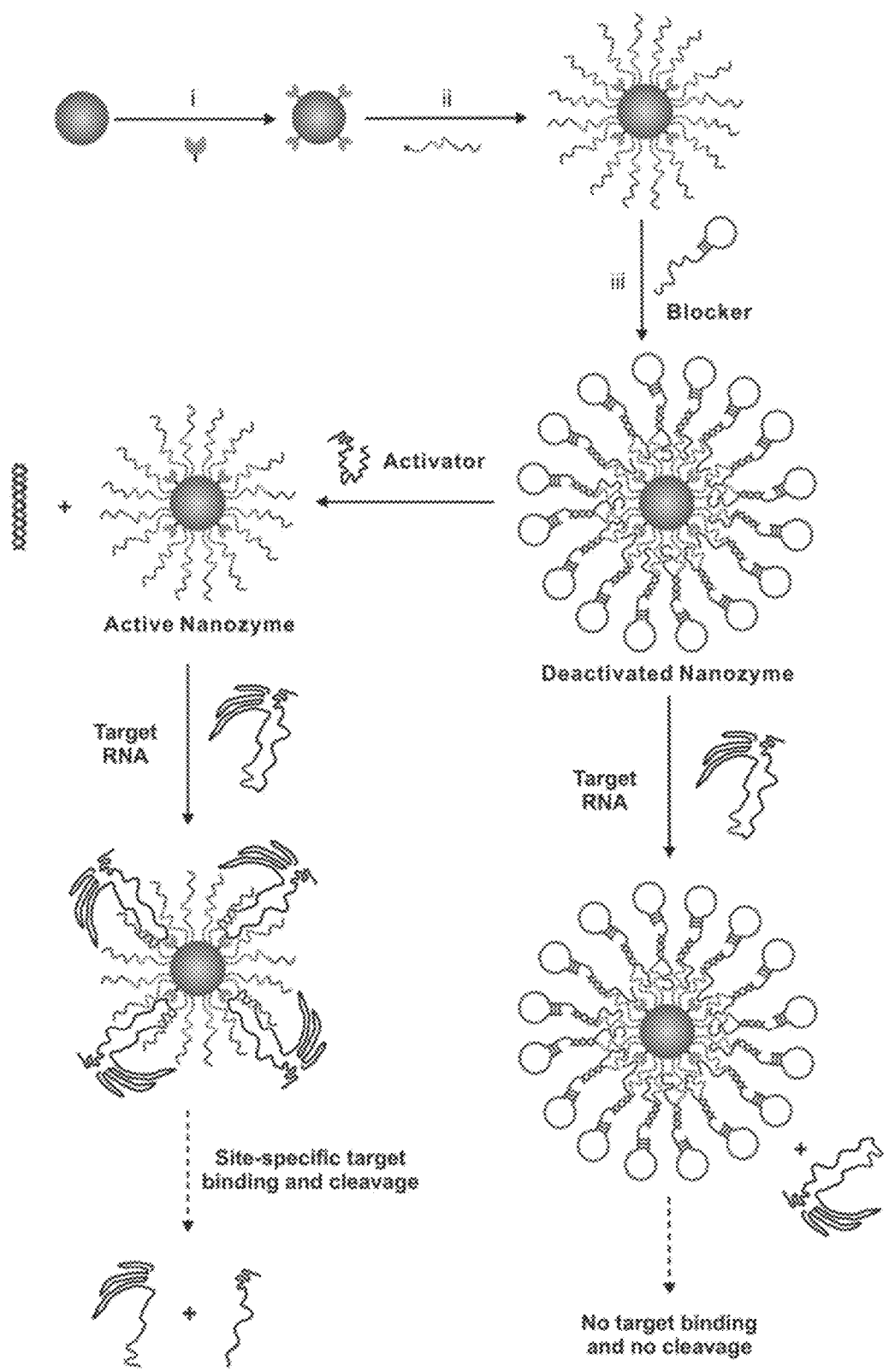
FIG. 9 is a schematic representation describing the design and function of an on-off switchable nanozyme.
Figure 10A:
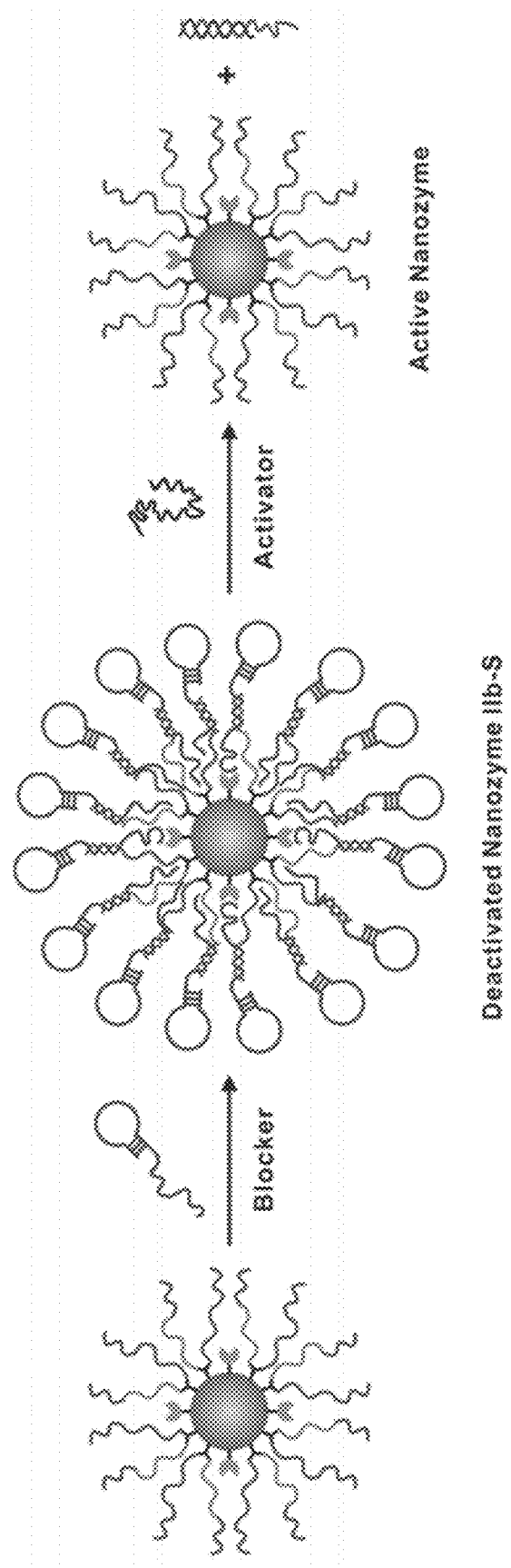
FIGS. 10A to 10C are schematic representations describing the design of on-off switchable nanozyme IIb-S (FIG. 10A), nanozyme IIIa-S (FIG. 10B) and nanozyme IIIb-S (FIG. 10C).
Figure 10B:
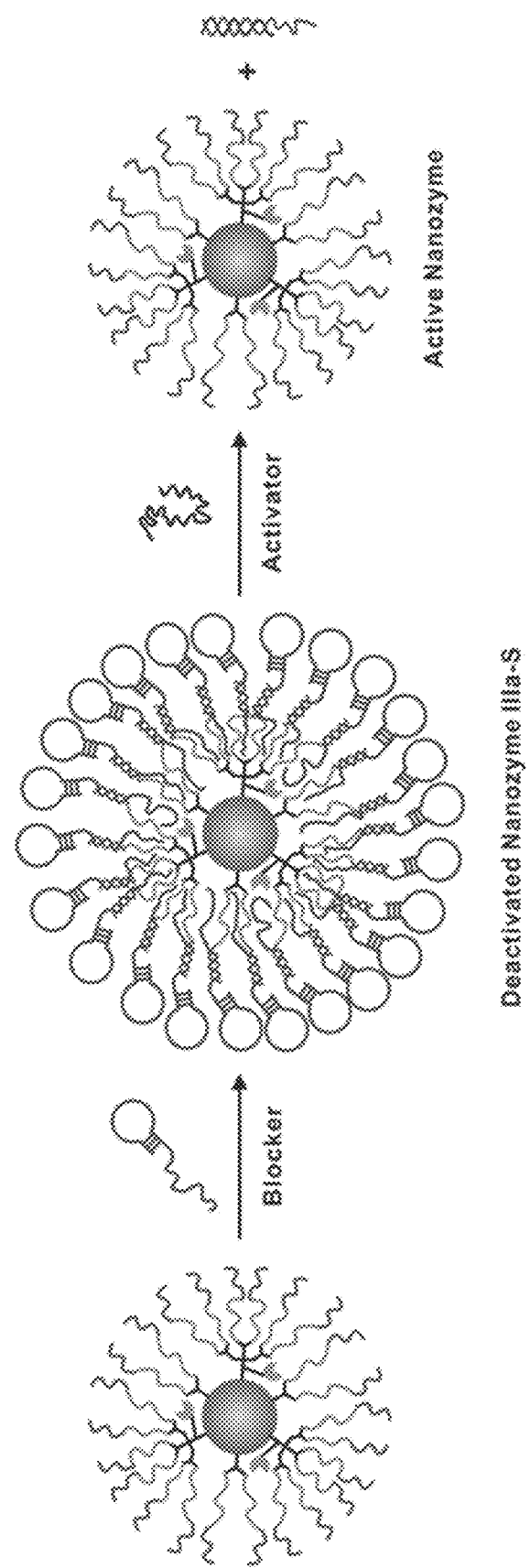
Figure 10C:
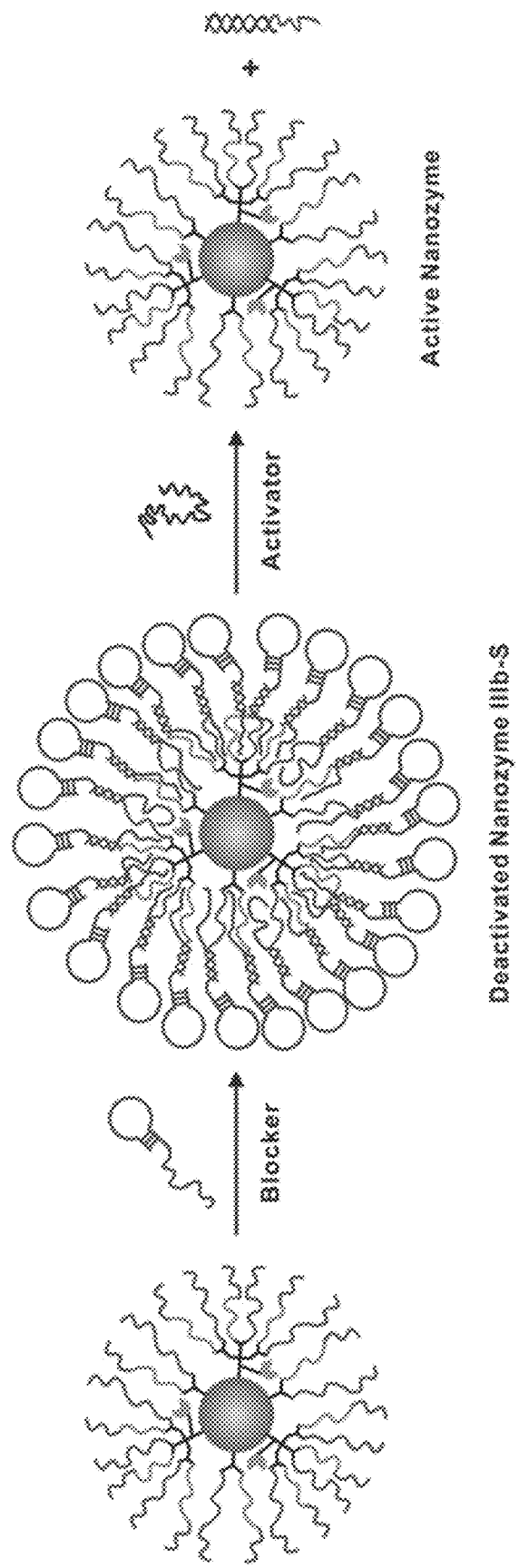
Figure 11:
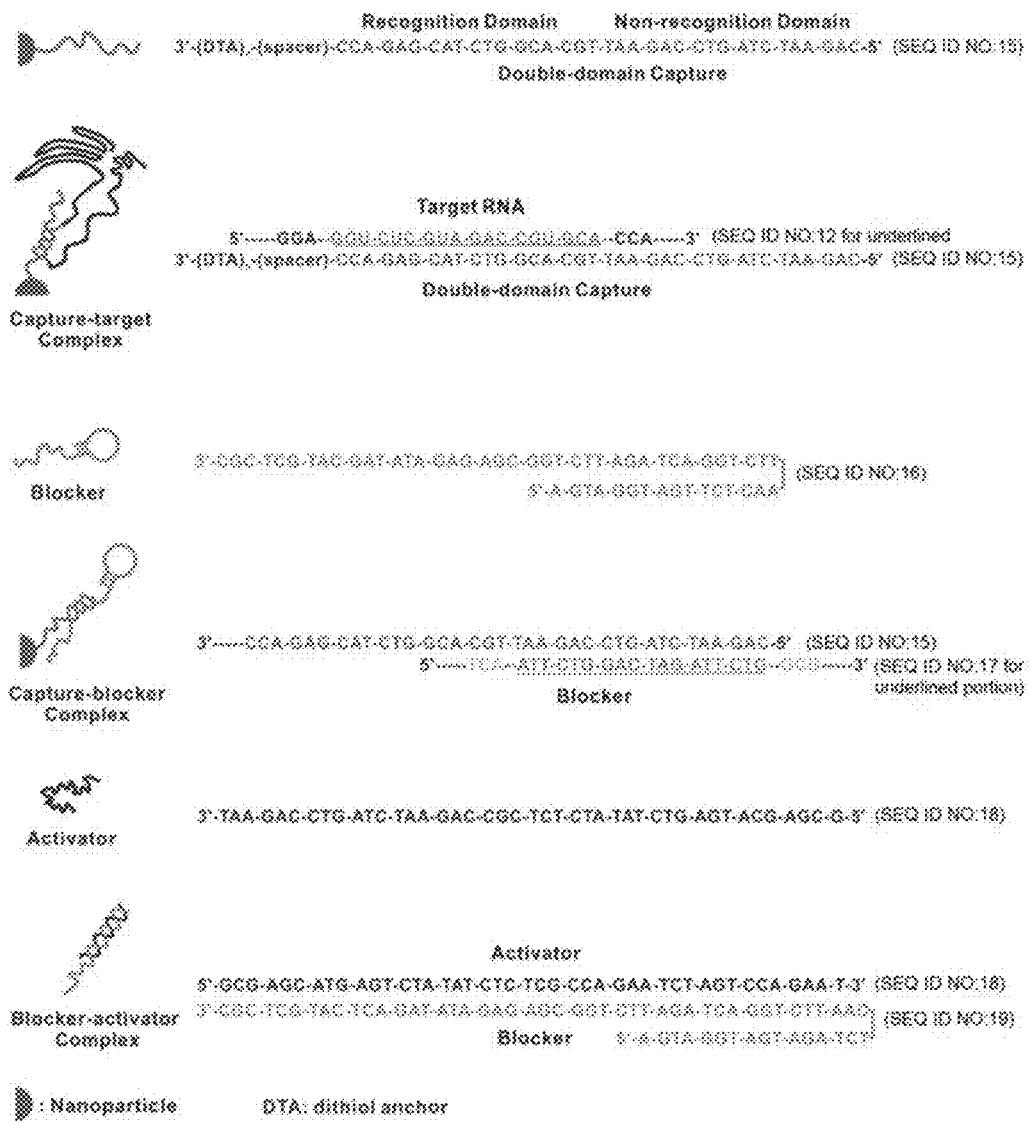
FIG. 11 is a schematic representation describing the nucleotide sequences of double-domain capture, blocker, activator and their complexes.

In this Example, nanozymes with an on-off-switching function are synthesized (FIGS. 9-11). Such nanozymes allow for an additional trigger to activate their function. This capability can provide additional selectivity for nanozyme's activity in a chosen environment (such as in a specific cell type, a tissue, or an organs), where exists a specific activator (or stimulus). This activator can be an RNA, DNA, or protein located in such living environment endogenously, or being created/delivered exogenously. Thus, this on-off switchable capability allows for selectively turning-on nanozyme's activities in response to a specific activator that exists in a targeted cell type, a tissue, or an organ.

Design and Synthesis of Nanozymes with On-Off-Switchable Functions

A specific design of on-off-switchable nanozymes is examined. In this design, functional blocker is a nucleic acid oligonucleotide, and active nanozymes have oligonucleotides with two sequence domains: (1) the recognition domain in Nanozyme IIa-S and IIIa-S has a "capture" oligonucleotide sequence complementary to that of an RNA target, and the recognition domain in nanozyme IIb-S and IIIb-S have branched double "capture" oligonucleotide sequence, and (2) the non-recognition domain has oligonucleotide sequence complementary to that of blocker oligonucleotides (FIGS. 9-11). Functional blockers can sequence-specifically bind onto nanozyme's the non-recognition oligonucleotide domain forming hairpin loops, thus deactivating the function of nanozymes through steric effects (FIGS. 9-11). Specifically, functional switchable nanozymes are formed in a three-step synthesis: (i) gold nanoparticles are functionalized with multi-thiol-capped RNase A, (ii) the resulting nanoparticles are functionalized with thiol-capped oligonucleotides that have both recognition and non-recognition domains, forming active nanozymes, and (iii) the active nanozymes are further functionalized with blocker oligonucleotides through hybridization in a PBS (e.g., 0.6 M NaCl) solution at the room temperature for a time period such as 12 hours forming deactivated nanozymes (FIGS. 9 and 10). The resulting deactivated nanozymes are isolated from synthesis solution via centrifugation and can be re-dispersed in a PBS buffer (e.g., 0.15 M NaCl) solution at room temperature. The size of deactivated nanozyme are characterized with dynamic light scattering, which show a size increase as compared with their active form, which is consistent with the binding between active nanozymes with their blocker oligonucleotides hairpins shown in FIGS. 9 and 10.

Evaluation of Nanozyme's On-Off-Function Switching Capability

The functional switchable capability of nanozymes are evaluated with three types of experiments. First, the deactivated nanozymes are incubate with their activator oligonucleotides in a PBS buffer (e.g., 0.15 M NaCl) solution at room temperature for 6 hours. The size of resulting nanozymes are characterized using dynamic light scattering, which shows a size decrease as compared with the deactivated nanozymes. This result suggests that the formation of active nanozymes via the hybridization between the blocker and activator oligonucleotides (FIG. 9-11). Second, the enzymatic activity of deactivated nanozymes (i) with and (ii) without the presence of activators are evaluation using the RNA molecular beacon target with fluorescence spectroscopy. Third the enzymatic activity of deactivated nanozymes (i) with and (ii) without the presence of activators are evaluated using 1149-nt HCV RNA target with 1257-nt AAT RNA as a control (FIG. 2), and electrophoresis analyses are used to examine the products of these reactions.

Example 7: Synthesis and Evaluation of Hollow Nanozyme without Inorganic Nanoparticle Cores All the above nanozymes can be made in the form of hollow nanozyme (H-nanozymes) without inorganic nanoparticle cores. The removal of the inorganic nanoparticle cores from nanozymes can effectively eliminate the potential long-term toxicity induced by the core, and also creates a cavity for loading and delivery of small molecule drugs (such as sorafenib) for cancer treatment.

To make core-removable nanozymes, RNA endonucleases and recognition ss-DNA oligonucleotides and unibodies are modified with multi-alkylthiol-terminated sequences of poly-thymine (T) bases modified with propargyl ether groups linked through an amidohexylacrylamido linker to the 5 position of the T base, and a subsequent spacer of six unmodified T bases for flexibility and accessibility of the remaining moieties. Propargyl ether groups can undergo polymerization on the surface of gold nanocrystals and cross-link all the ligands into monolithic structures, which can maintain their structural integrity after the removal of gold nanocrystal with KCN.

Synthesis and Characterization of H-Nanozyme (IIa) and H-Nanozyme (IIb)

Figure 12:
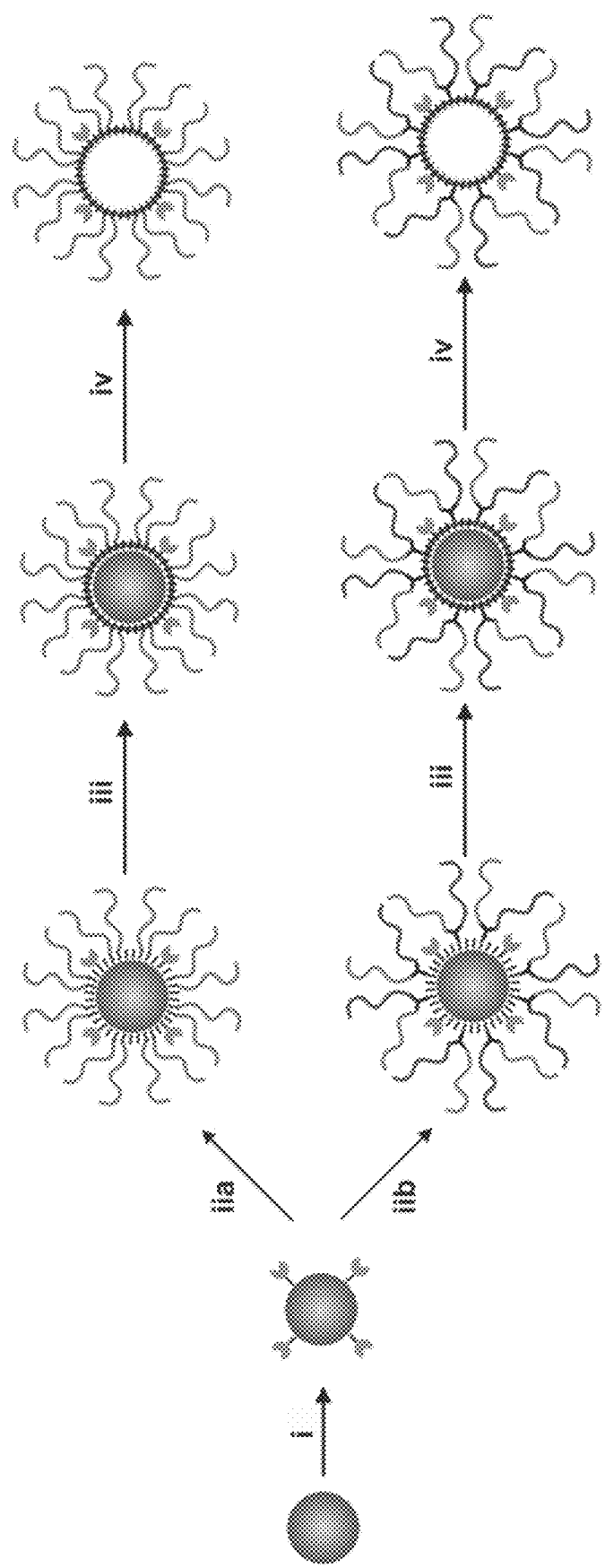
FIG. 12 is a schematic representation describing the synthesis of H-nanozyme IIa and H-nanozyme IIb. i. surface functionalization with alkylthiol-terminated and propargyl-ether-modified RNA endonucleases; ii. functionalization with alkylthiol-terminated and propargyl-ether-modified, single-sequenced capturers (a) and branched double-sequenced Capturers (b), and then co-functionalization with alkylthiol-terminated and propargyl-ether-modified supporter oligonucleotides; iii. polymerization; and iv. Au core removal with KCN.

H-nanozymes with single-sequenced capturers (H-Nanozyme IIa) and H-nanozyme with branched double-sequenced capturers (H-Nanozyme IIb) are synthesized in four steps (FIG. 12). In the first step, gold nanoparticles are modified with multi-alkylthiol-terminated and propargyl-ether-modified RNA endonucleases via gold/thiol linking chemistry. In the second step, god-nanoparticle-RNA-endonucleases complexes are first functionalized with alkylthiol-terminated and propargyl-ether-modified single-sequenced capturers (iia) and branched double-sequenced Capturers (iib), respectively. Then, the resulting particles are further capped with structural supporters (alkylthiol-terminated and propargyl-ether-modified poly-thymine (T) sequences Co-functionalization with structural supporter oligonucleotides is important for the maintenance of structural integrity of H-nanozymes. In the third step, the resultant nanoparticles from previous step are isolated via centrifugation and are re-dispersed in phosphate-buffered saline (0.15 M) and then are incubated at the room temperature for 12 hours, cross-linking takes place between the propargyl groups on the surface of the gold nanoparticle and along the modified T bases, yielding a densely packed, cross-linked DNA shell on the surface of gold nanoparticles. In the fourth step, gold nanoparticle cores are removed with an aqueous KCN solution (1 µM), and the resulting hollow nanostructures is purified through multiple centrifugations (FIG. 12). The resulting H-nanozyme IIa and IIb are characterized with TEM and dynamic light scattering. Their enzymatic activity and selectivity are characterized using methods described in above.

H-Nanozyme IIIa and IIIb Preparation and Enzymatic Testing

Figure 13:
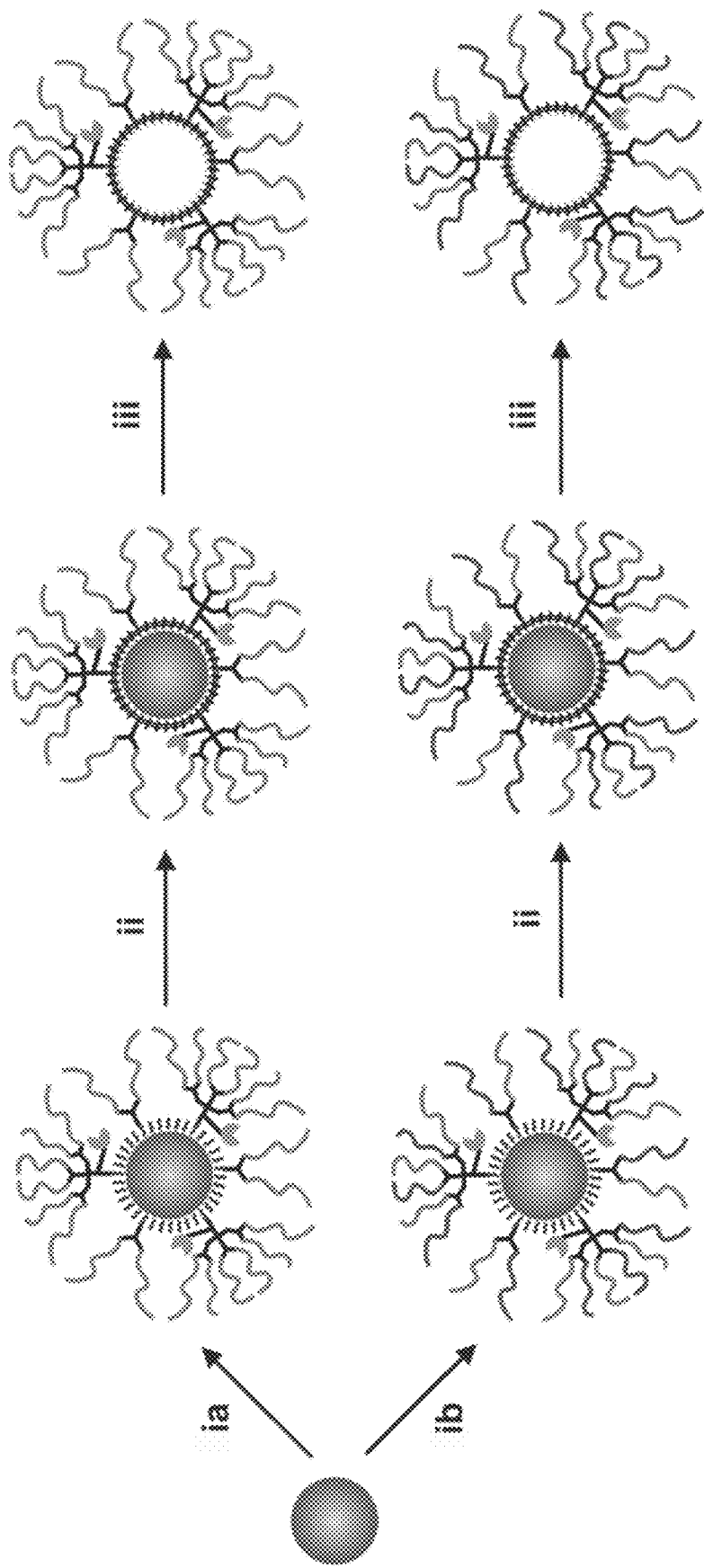
FIG. 13 is a schematic representation describing the synthesis of H-Nanozyme IIIa and H-Nanozyme IIIb. i. Surface functionalization with alkylthiol-terminated and propargyl-ether-modified DNA-RNase unibodies with single-sequenced capturers (a) and unibodies with branched double-sequenced capturers (b). Then, co-functionalization with alkylthiol-terminated and propargyl-ether-modified supporter oligonucleotides; ii. polymerization; and iii. Au nanoparticle core removal with a KCN solution.
Figure 14:
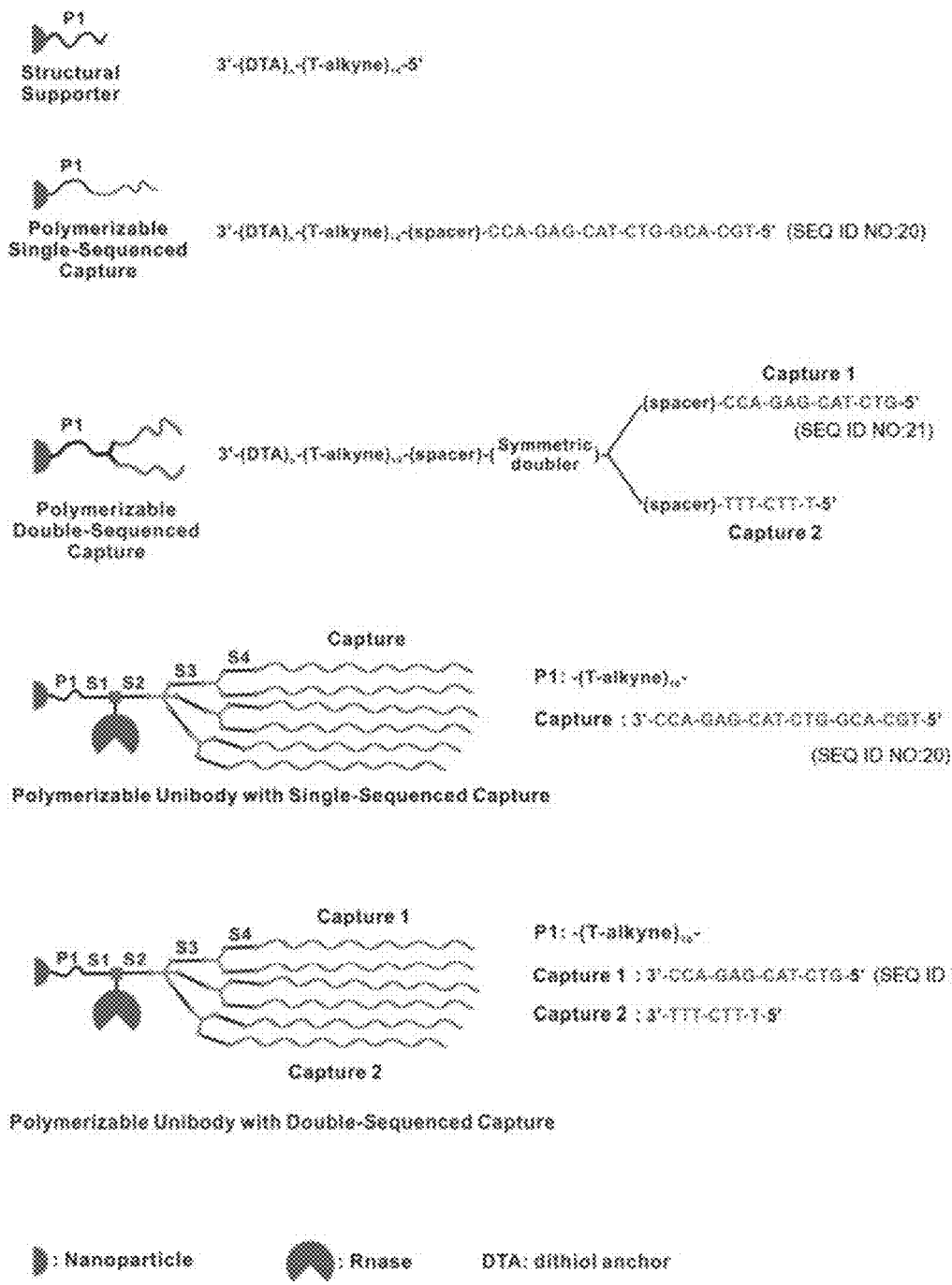
FIG. 14 is a schematic representation describing the nucleotide sequences of structure supporter and polymerizable building blocks used in H-nanozymes shown in FIGS. 11 and 12.

H-nanozymes formed from DNA-RNase unibodies with single-sequenced capturers (H-Nanozyme IIIa) and from unibodies with branched double-sequenced capturers (H-Nanozyme IIIb) are prepared in a three-step synthesis (FIGS. 13 and 14). In the first step, gold nanoparticles are functionalized with multi-alkylthiol-terminated and propargyl-ether-modified unibodies with single-sequenced capturers (a) and branched double-sequenced capturers (b), respectively. Then, the resulting particles are further functionalized with alkylthiol-terminated and propargyl-ether-modified structural supporters. In the second step, the resultant nanoparticles from previous step are isolated via centrifugation and are re-dispersed in phosphate-buffered saline (0.15 M) and incubated at the room temperature for 12 hours. Cross-linking takes place between the propargyl groups on the surface of the gold nanoparticle and along the modified T bases, yielding a densely packed, cross-linked DNA shell on the surface of gold nanoparticles. In the fourth step, gold nanoparticle cores are removed with an aqueous KCN solution (1 µM), and the resulting hollow nanostructures will be purified through multiple centrifugations (FIG. 13). The resulting H-nanozyme IIIa and IIIb are characterized with TEM and dynamic light scattering. Their enzymatic activity and selectivity are characterized using methods described in C 3.2 and C 3.3.

On-Off Switchable H-Nanozyme II and Enzymatic Testing

Figure 15A:
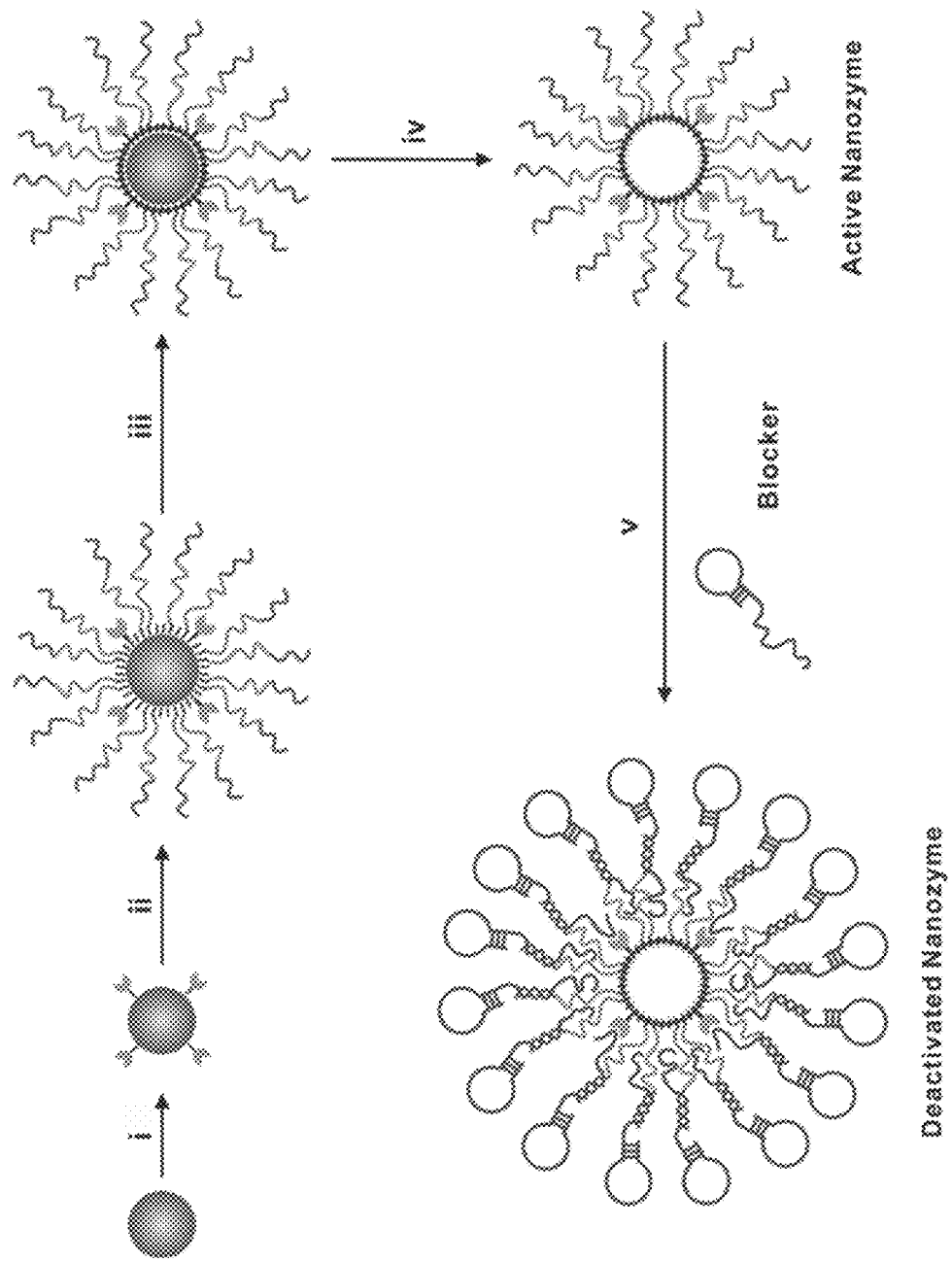
FIGS. 15A and 15B are schematic representations describing the synthesis of functional on-off switchable H-nanozyme IIa-S (FIG. 15A) and H-nanozyme IIb-S (FIG. 15B). i. surface functionalization with alkylthiol-terminated and propargyl-ether-modified RNA endonucleases; ii. functionalization with alkylthiol-terminated and propargyl-ether-modified, two-domain oligonucleotides, and then co-functionalization with alkylthiol-terminated and propargyl-ether-modified supporter oligonucleotides; iii. polymerization; iv. Au core removal with KCN; and v. hybridization with blocker oligonucleotides forming deactivated H-Nanozymes, which function can be switched on in the presence of activators as shown in FIGS. 9 and 10.
Figure 15B:
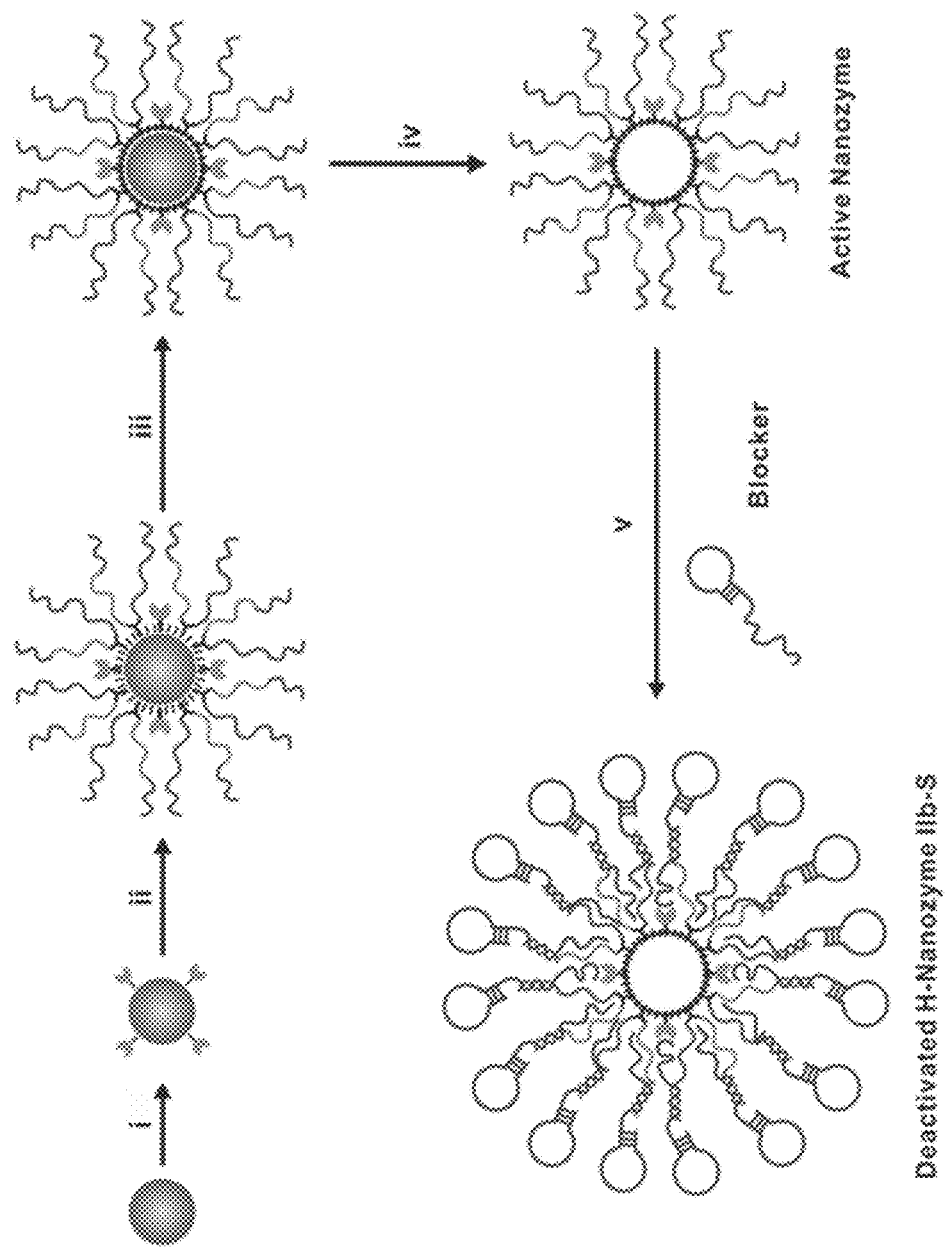
Figure 17:
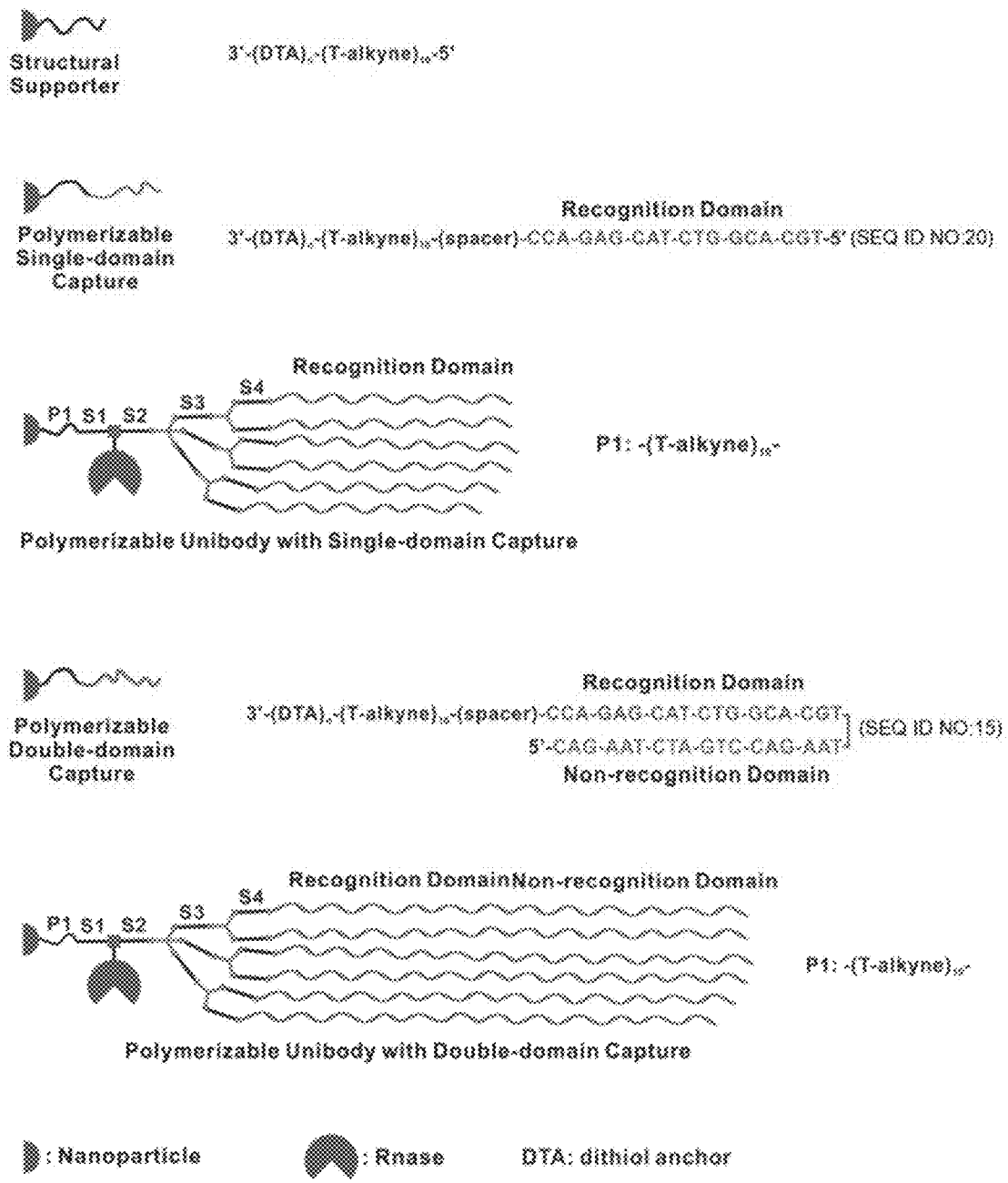
FIG. 17 is a schematic representation describing the nucleotide sequences of structure supporter and polymerizable building blocks used in H-nanozymes shown in FIGS. 15 and 16.

H-Nanozymes IIa and IIb with an on-off switchable function are synthesized in five steps (FIGS. 15 and 17). In the first step, gold nanoparticles are modified with multi-alkylthiol-terminated and propargyl-ether-modified RNA endonucleases. In the second step, gold-nanoparticle-RNase complexes are first functionalized with alkylthiol-terminated and propargyl-ether-modified oligonucleotide with recognition and non-recognition domains. Then, the resulting particles are functionalized with structural supporters (alkyl-thiol-terminated and propargyl-ether-modified poly-thymine (T) sequences). In the third step, the resultant nanoparticles from previous step are isolated via centrifugation and are re-dispersed in phosphate-buffered saline (0.15 M), and then they are incubated at the room temperature for 12 hours. Cross-linking takes place between the propargyl groups on the surface of the gold nanoparticle and along the modified T bases, yielding a densely packed, cross-linked DNA shell on the surface of gold nanoparticles. In the fourth step, gold nanoparticle cores are removed with an aqueous KCN solution (1 µM), and the resulting hollow nanostructures are purified through multiple centrifugations (FIGS. 15 and 17). The resulting H-nanozyme are in their active form. In the fifth step, the active H-Nanozymes are incubated with their sequence specific blocker oligonucleotides in a phosphate-buffered saline (0.6 M) at the room temperature for 12 hours, forming deactivated H-Nanozymes. The resulting deactivated H-Nanozymes are purified with multiple centrifugations and are re-dispersed in a phosphate-buffered saline solution (0.15 M) for use. The resulting active and deactivated H-nanozymes are characterized with TEM and dynamic light scattering. Their enzymatic activity and target selectivity are examined using the method described above.

On-Off Switchable H-Nanozyme III and Enzymatic Testing

Figure 16A:
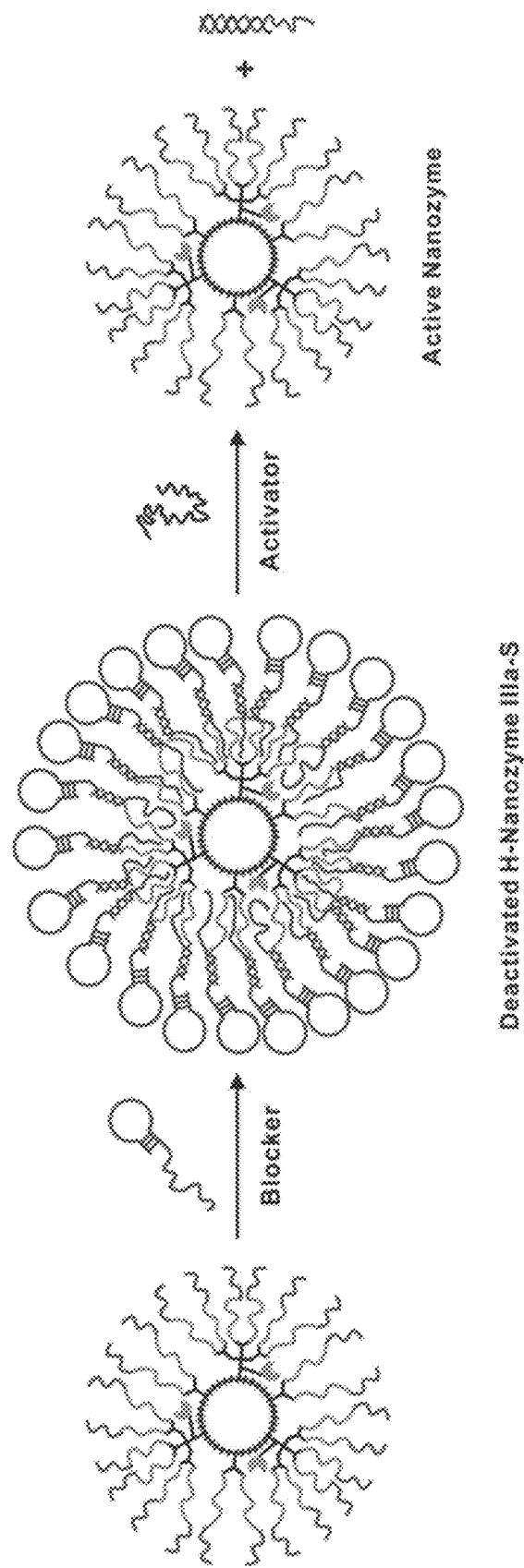
FIGS. 16A and 16B are schematic representations describing the design of functional on-off switchable H-nanozyme IIIa-S (FIG. 16A) and H-nanozyme IIIb-S (FIG. 16B).
Figure 16B:
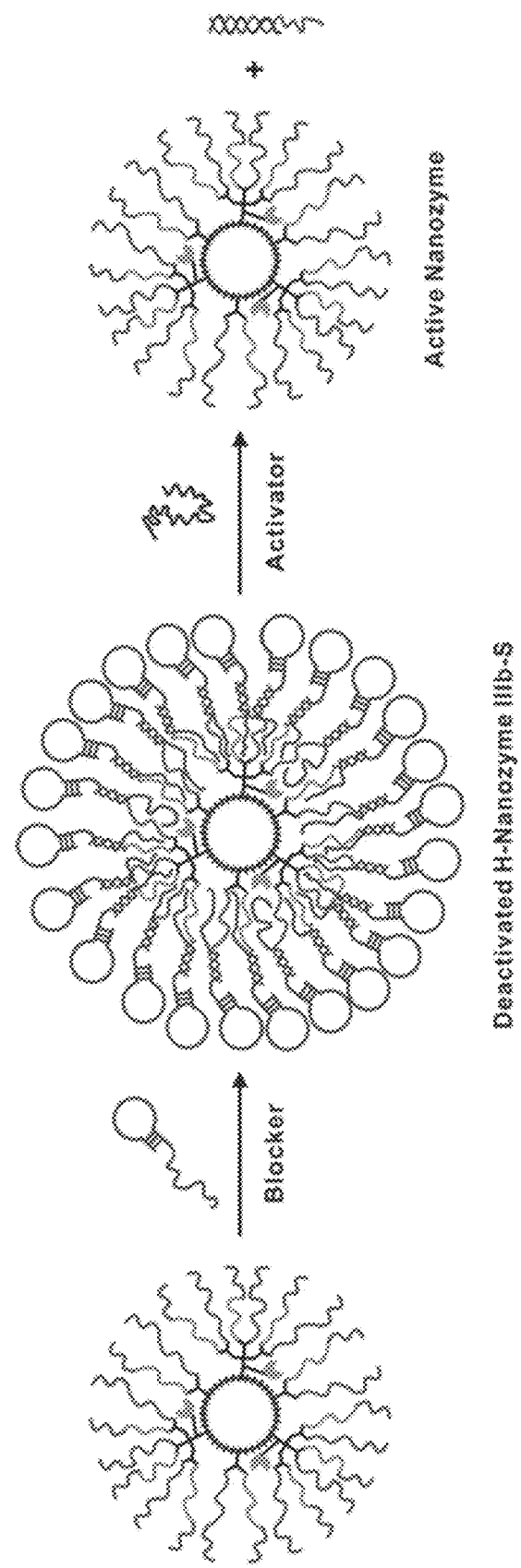

H-Nanozymes IIIa and IIIb with an on-off switchable function are synthesized in five steps (FIGS. 16 and 17). In the first step, gold nanoparticles are modified with multi-alkylthiol-terminated and propargyl-ether-modified DNA-RNase unibodies with single-sequenced capturers (H-Nanozyme IIIa) and from unibodies with branched double-sequenced capturers (H-Nanozyme IIIb). Then the resulting particles are functionalized with structural supporters (alkylthiol-terminated and propargyl-ether-modified poly-thymine (T) sequences). In the second step, the resultant nanoparticles from previous step are isolated via centrifugation and are re-dispersed in phosphate-buffered saline (0.15 M), and then they are incubated at the room temperature for 12 hours. Cross-linking takes place between the propargyl groups on the surface of the gold nanoparticle and along the modified T bases, yielding a densely packed, cross-linked DNA shell on the surface of gold nanoparticles. In the third step, gold nanoparticle cores are removed with an aqueous KCN solution (1 µM), and the resulting hollow nanostructures are purified through multiple centrifugations (FIGS. 16 and 17). The resulting H-nanozyme are in their active form. In the fourth step, the active H-Nanozymes are incubated with their sequence specific blocker oligonucleotides in a phosphate-buffered saline (0.6 M) at the room temperature for 12 hours, forming deactivated H-Nanozymes. The resulting deactivated H-Nanozymes are purified with multiple centrifugations and are re-dispersed in a phosphate-buffered saline solution (0.15 M) for use. The resulting active and deactivated H-nanozymes are characterized with TEM and dynamic light scattering. Their enzymatic activity and target selectivity are examined using the method described above.

Example 8. Expression and Purification of A19C and G88C Mutant RNase A (Ala19 and Gly 88 Mutated into Cysteine, Respectively)

Figure 32:
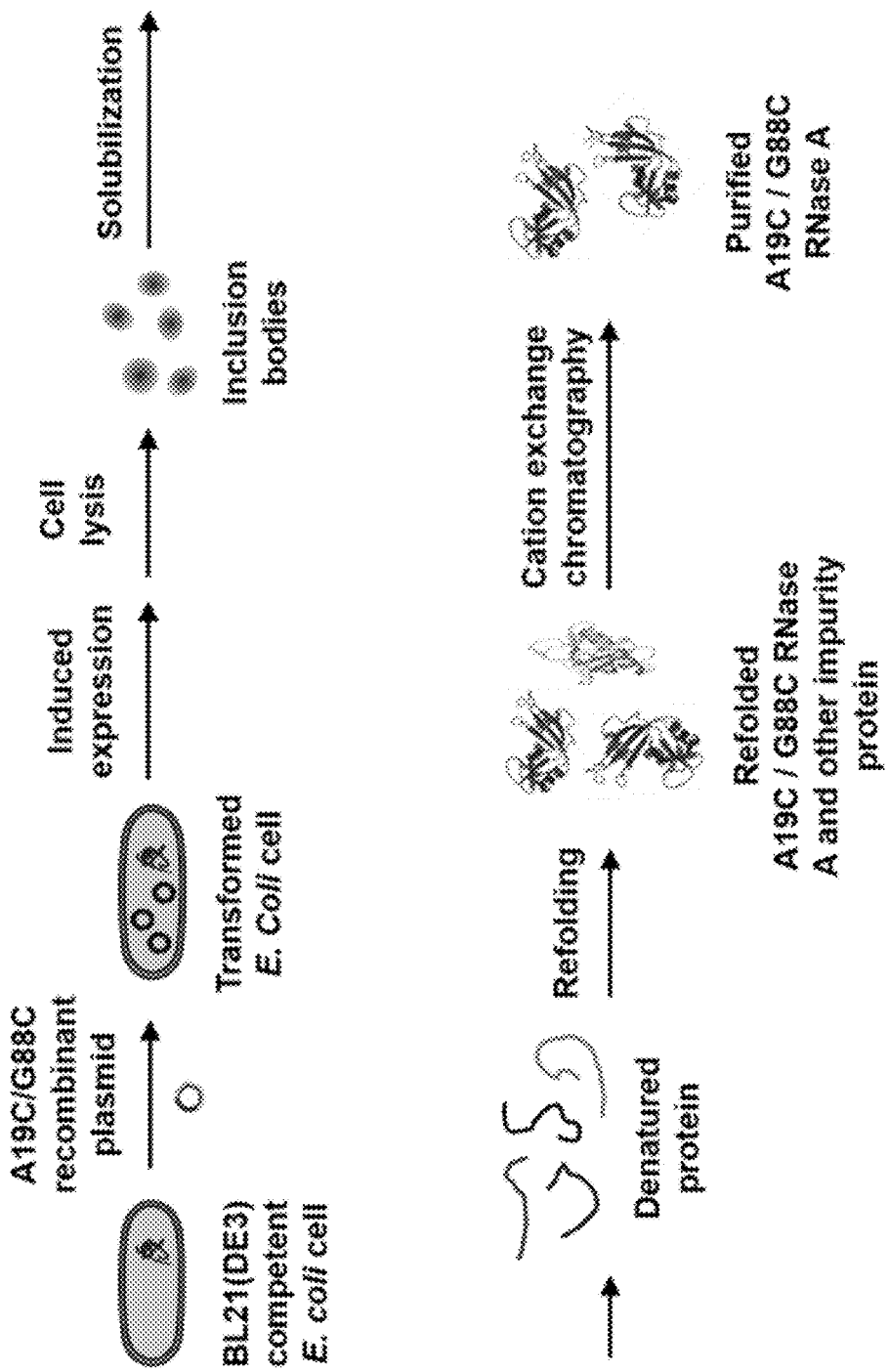
FIG. 32 shows A19C/G88C mutant RNase A expression and purification procedures.

The protocol of mutant RNase A expression and purification was based on reported procedures (Scheme 1, FIG. 32) (Delcardayre, S B., et al. Protein Eng 1995 8:261-273; Rutkoski, T J., et al. Cancer Biol Ther 2011 12:208-214). Specifically, BL21(DE3) Competent *E. coli* carrying T7 RNA polimerase gene (New England BioLabs, strain genotype: fhuA2 [lon] ompT gal (λ DE3) [dcm]ΔhsdS λ, DE3=λ sBamHIo ΔEcoRI-B int::(lacI::PlacUV5::T7 gene1) i21 Δnin5) were transformed with pET22b(+)/pET27b(+) plasmids encoding mutated RNase A following the protocol from cell suppliers and cultured in Lysogeny broth containing ampicillin overnight, then tiny amount of *E. coli* cells were transferred onto ampicillin-containing Lysogeny broth agar plate. After 8 h growth, a single colony was picked and further cultured in Lysogeny broth to expand the colony. After 12 h growth, E. coli cells were harvested and plasmids were extracted. The extracted plasmids were sequenced to confirm the successful transformation of correct plasmids. For large scale expression of A19C/G88C mutant RNase A, 20 mL of overnight cultured E. coli cells with corresponding plasmids encoding mutant RNase A were used to inoculate a large culture (1.0 L terrific broth). After 4.5 h growth, isopropyl β-D-thiogalactoside was added to induce the expression of mutant RNase A, then after 3.0 h growth, E. coli cells were harvested by centrifuge at 5000 rpm for 10 min.

The pelleted E. coli cells containing mutant RNase A were first lysed with Bugbuster buffer (Millipore Sigma) following manufacturer's instructions and centrifuged to collect the inclusion bodies. The collected inclusions bodies were further washed with PBS for 3 more times by centrifuge and then solubilized by solubilization buffer (Tris-HCl pH 7.80, urea 6.00 M, NaCl 0.400 M, DTT 100 mM, ethylenediaminetetraacetic acid 1.00 mM). The fully dissolved solution of inclusion bodies was centrifuged to remove any insoluble precipitate, then diluted by 10-fold with degassed 20 mM acetic acid solution. Such diluted solution of dissolved inclusion bodies was dialyzed (10 kDa molecular weight cut-off, ThermoFisher Scientific) overnight against 20 mM acetic acid pre-purged with nitrogen to obtained denatured mutant RNase A solution.

To prepare enzymatically-active protein, the denatured mutant RNase A was refolded. Specifically, the denatured mutant RNase A solution was slowly added into nitrogen pre-purged refolding solution (Tris-HCl buffer 0.10 M pH 8.0, NaCl 0.10 M, L-arginine 0.50 M, ethylenediaminetetraacetic acid 10 mM, reduced glutathione 1.0 mM, oxidized glutathione 0.20 mM). This solution was stored under 4° C. for over 5 days to complete the refolding process.

Figure 18B:
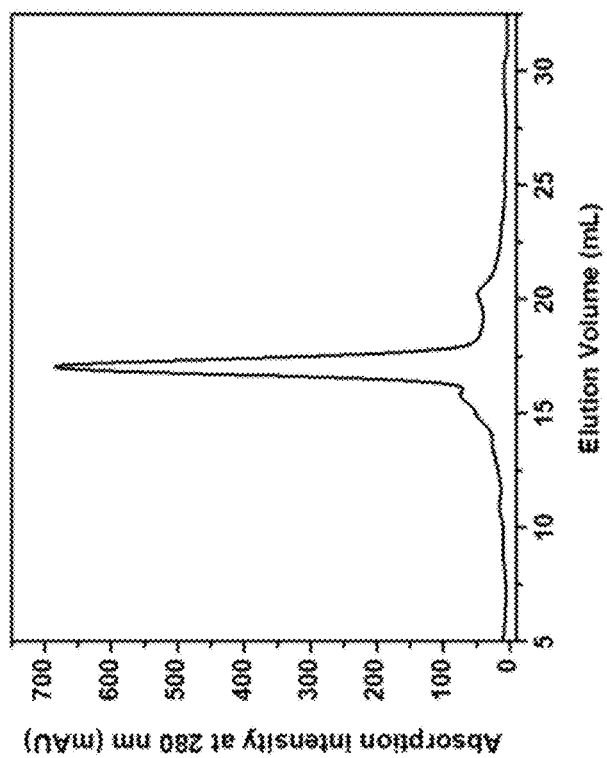
FIGS. 18A to 18B show typical A19C (FIG. 18A) and G88C (FIG. 18B) fast protein liquid chromatography chromatogram.
Figure 18A:
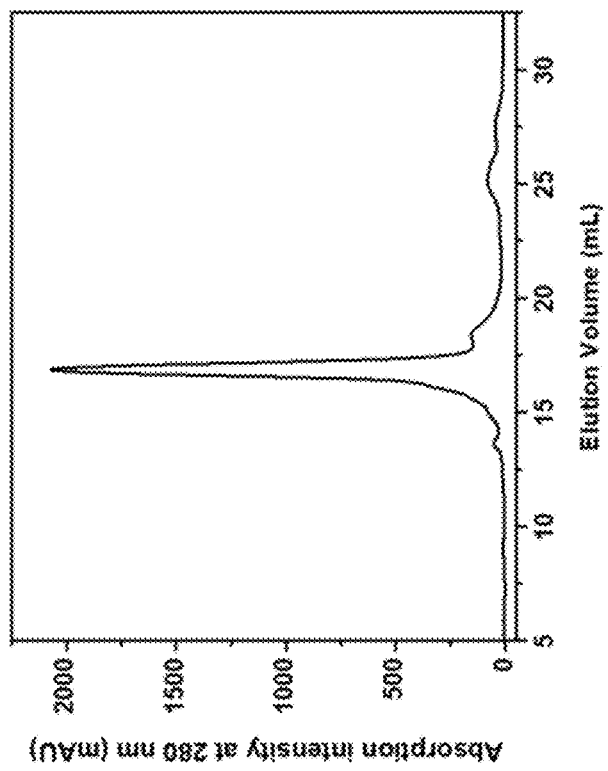
Figure 33:
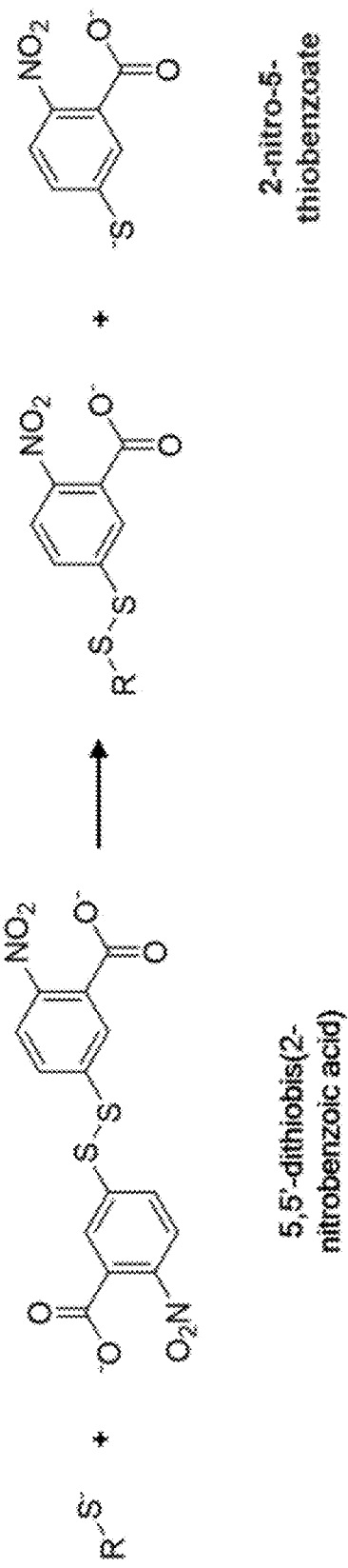
FIG. 33 shows thiol capping with 5,5'-dithiobis(2-nitrobenzoic acid).

The solution of refolded protein was concentrated with centrifugal filters (10 kDa molecular weight cut-off, Millipore Sigma). In order to protect the thiol group from being oxidized, 10-fold excess 5,5'-dithiobis(2-nitrobenzoic acid) was used to react with the refolded mutant RNase A in Tris-HCl buffer (pH 8.0) containing 10 mM ethylenediaminetetraacetic acid to cap the thiol group (Scheme 2, FIG. 33). The excess 5,5'-dithiobis(2-nitrobenzoic acid) was removed by NAP-10 desalting column (GE healthcare). Finally, the thiol-capped mutant RNase A was applied to a HiTrap SP cation-exchange column (GE healthcare) and eluted with a linear gradient of NaCl (0.15-1.0 M) in 50 mM NaOAc buffer (pH 5.0). Typical fast protein liquid chromatography data of A19C and G88C purification were shown in FIG. 18. Upon usage, the capped thiol group was de-capped by 1.0 mM dithiothreitol treatment and desalted into proper buffer using NAP-5 desalting column (GE Healthcare).

Figure 19B:
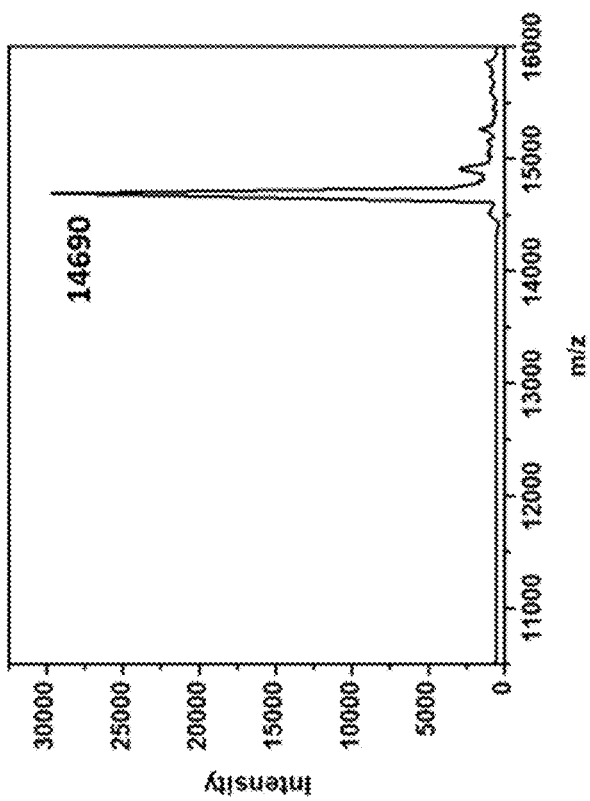
FIGS. 19A and 19B show MALDI-TOF spectrum of A19C (FIG. 19A) and LA-A19C (FIG. 19B) via copper free click chemistry. The expected m/z for A19C and LA-A19C were 13803 and 14753. The observed m/z for them were 13747 and 14690.
Figure 19A:
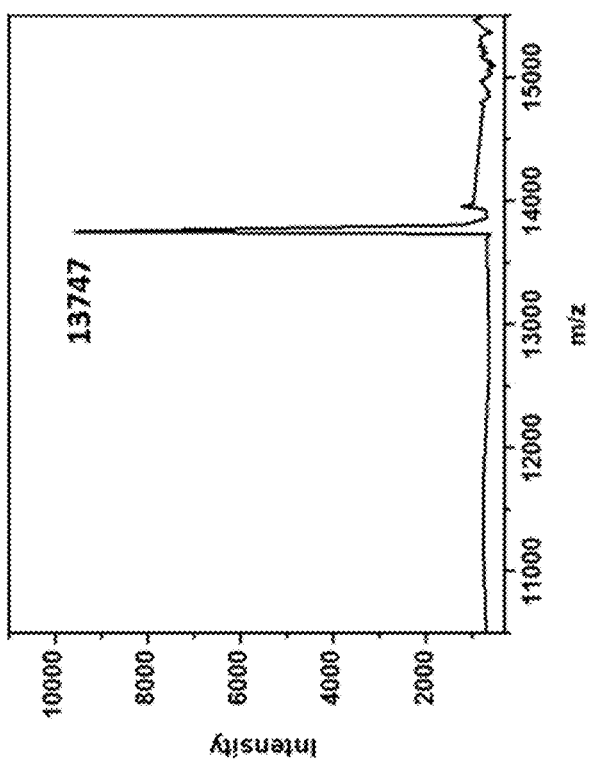
Figure 34:
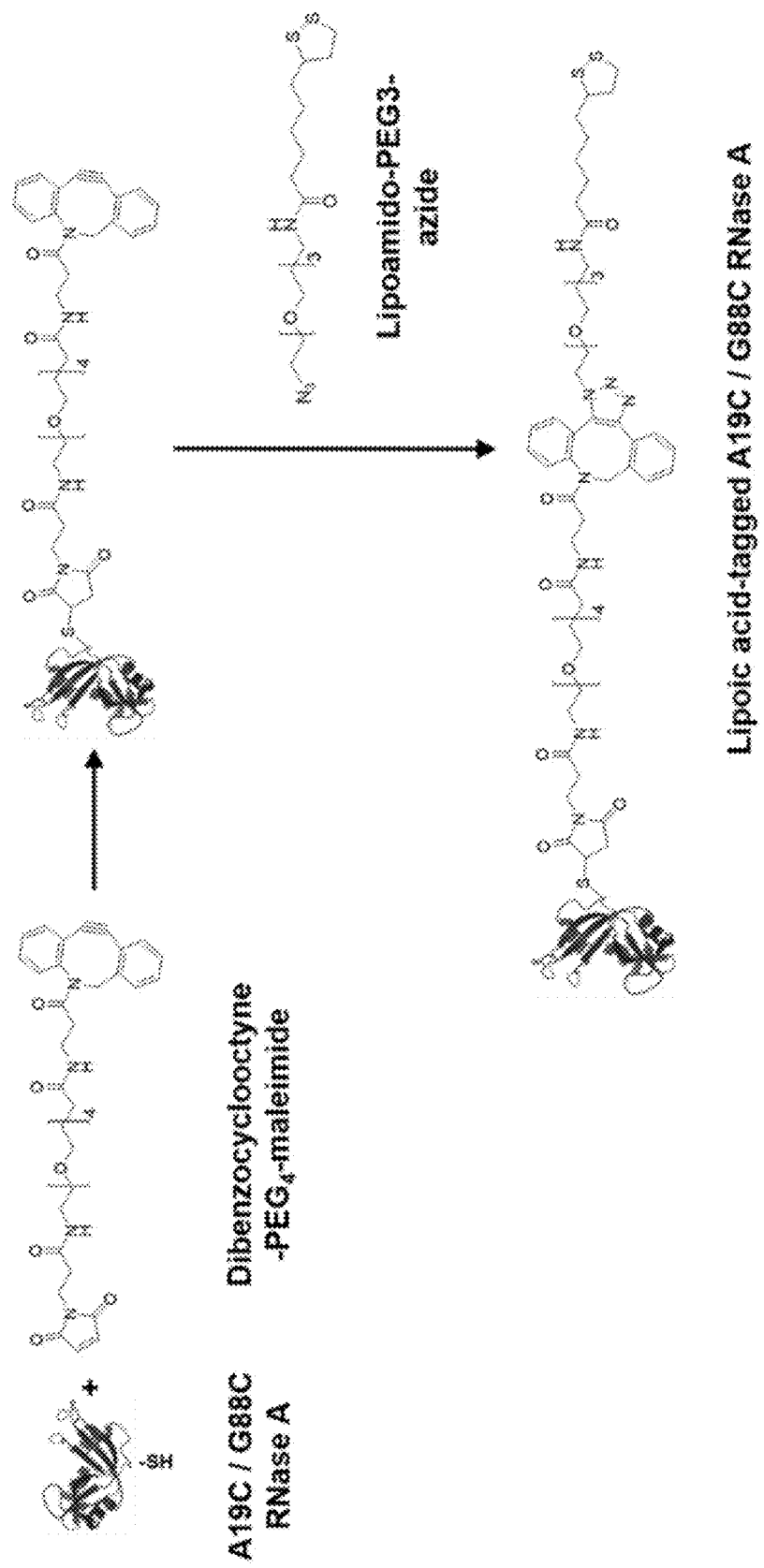
FIG. 34 shows A19C/G88C tagging with lipoic acid moiety via copper free click chemistry.

Example 9. A19C/G88C Tagging with Lipoic Acid Moiety (LA-A19C/G88C) Via Click Chemistry LA-A19C/G88C was prepared through two steps of reactions (Scheme 3, FIG. 34). First of all, clickable dibenzylcyclooctyne functional groups were introduced onto mutated cysteine site by reacting A19C/G88C mutant RNase A with 10-fold molar excess of dibenzylcyclooctyne-PEG$_4$-maleimide in 0.10 M phosphate buffer (pH 7.0) containing 10 mM ethylenediaminetetraacetic acid for 3 hours. The unreacted dibenzylcyclooctyne-PEG$_4$-maleimide was removed by NAP-5 desalting column. Then the obtained dibenzylcyclooctyne-containing A19C/G88C mutant RNase A was further reacted with 10-fold molar excess of lipoamido-PEG3-azide in PBS for 5 hours to yield LA-A19C/G88C. The crude product was applied to HiTrap SP cation-exchange column and eluted with a linear gradient of NaCl (0.15-1.0 M) in 50 mM NaOAc buffer (pH 5.0) to have pure LA-A19C/G88C A19C. The purity was checked by MALDI-TOF (FIG. 19).

Figure 20B:
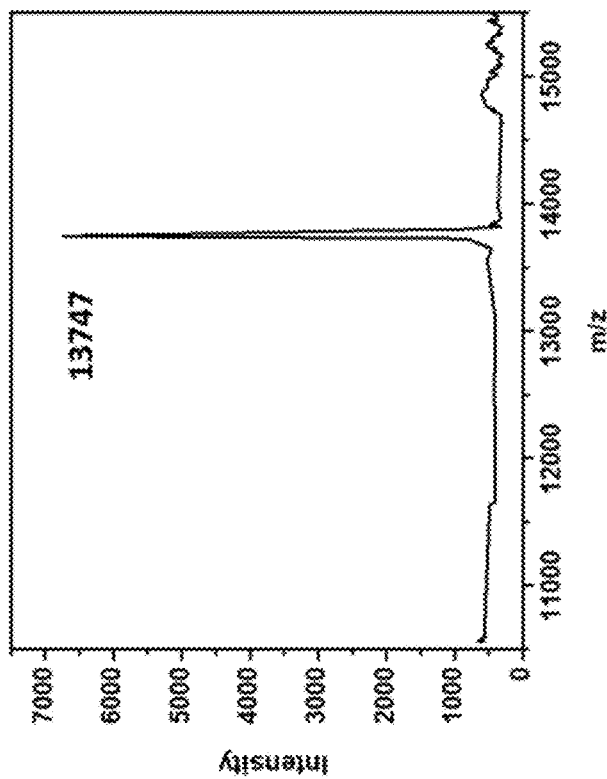
FIGS. 20A and 20B show MALDI-TOF spectrum of A19C (FIG. 20A) and LA-A19C (FIG. 20B) via copper assisted click chemistry. No m/z change were observed after reaction.
Figure 20A:
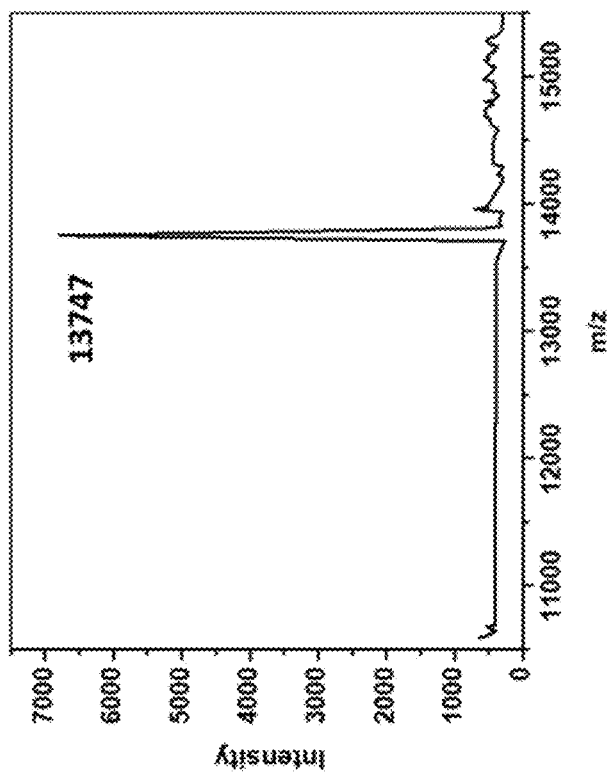
Figure 35:
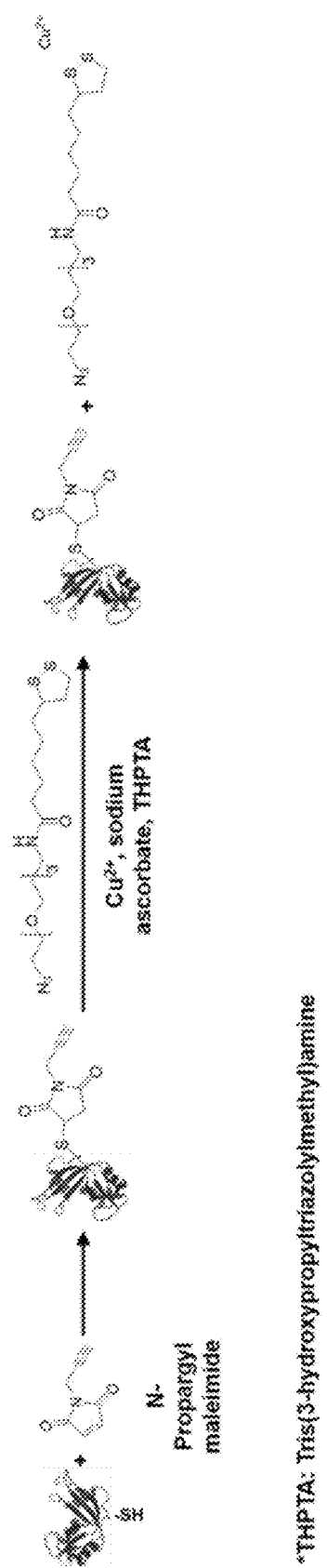
FIG. 35 shows A19C/G88C tagging with lipoic acid moiety via copper assisted click chemistry.

Classical copper assisted click chemistry was also tried to tag A19C and G88C with lipoic acid moiety (Scheme 4, FIG. 35). However, due to the strong chelating interaction between copper and thiol, the reaction exhibited extremely low yield and no product was detected in MALDI-TOF (FIG. 20).

Example 10. Evaluation of Enzymatic Activity of A19C/G88C and LA-A19C/G88C

Figure 36:
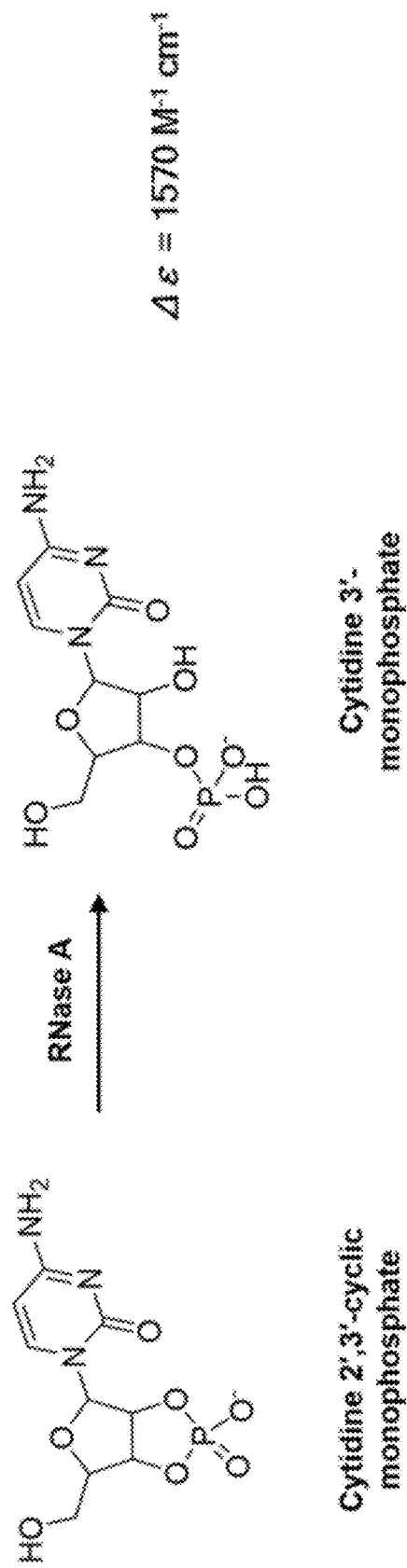
FIG. 36 shows cytidine 2',3'-cyclic monophosphate hydrolyzing by RNase A.

The ribonucleolytic activity of RNase A is essential for the gene silencing effect of nanozyme. Thus, the steady-state kinetic parameters of A19C/G88C mutant RNase A as wells as LA-A19C/G88C was measured and compared with those of wild type RNase A, following a method developed by Crook et al. (Scheme 5, FIG. 36) (Crook, E M., et al. Biochem J 1960 74:234-238). Specifically, cytidine 2',3'-cyclic monophosphate was used as the substrate. Substrate of different concentrations was mixed with 1.00 μM of enzyme and the mixtures' absorbance at 286 nm was recorded as a function of time. With cytidine 2',3'-cyclic monophosphate being hydrolyzed into cytidine 3'-monophosphate, the absorbance at 286 nm keeps increasing. From the absorbance increasing, the reaction's initial velocity was calculated and fitted into Lineweaver-Burk plot to determine the enzyme's steady-state kinetic parameters.

Compared with wild-type RNase A, both A19C and G88C exhibited only a slightly decreased activity, and their $k_{cat}/K_M$ was found to be about 75% of that for wild type RNase A (Table 2). This is in accordance with the previous reported data (Rutkoski, T J., et al. Cancer Biol Ther 2011 12:208-214; Rutkoski, T J., Bioconjug Chem. 2010 21:1691-1702). After being tagged with lipoic acid moiety, the $k_{cat}/K_M$ of LA-A19C/G88C was found to be about 90% of those for A19C/G88C before reaction, indicating that tagging with lipoic acid moiety did not cause a significant change in enzyme's catalytic activity.

TABLE 2

Steady-state kinetic parameters of wild-type RNase A, A19C, G88C, LA-A19C and LA-G88C.

|  | $k_{cat}$ (s$^{-1}$) | $K_M$ (mM) | $k_{cat}/K_M$ (M$^{-1}$ × s$^{-1}$) |
|---|---|---|---|
| Wild-type RNase A | 1.19 ± 0.162 | 1.23 ± 0.158 | 975 ± 44.6 |
| A19C | 0.860 ± 0.104 | 1.13 ± 0.123 | 758 ± 13.5 |
| G88C | 1.10 ± 0.50 | 1.52 ± 0.123 | 728 ± 41.5 |
| LA-A19C | 1.16 ± 0.222 | 1.71 ± 0.393 | 682 ± 40.2 |
| LA-G88C | 1.15 ± 0.97 | 1.80 ± 0.182 | 642 ± 37.7 |

Example 11. Optimization of RNase A Loading Conditions

Figure 37:
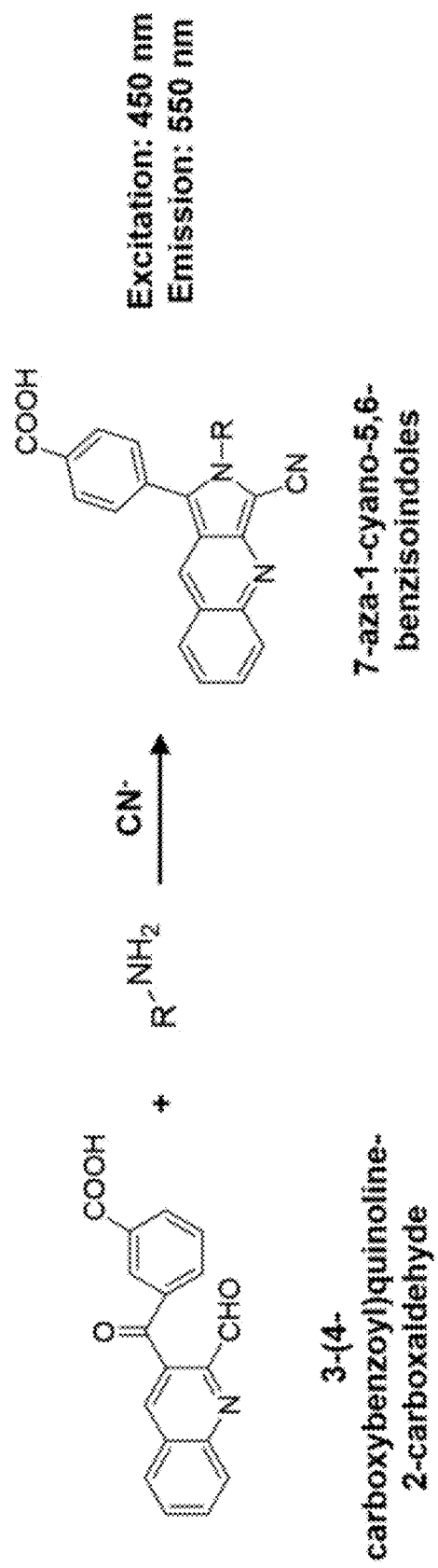
FIG. 37 shows reaction of the fluorogenic 3-(4-carboxybenzoyl)quinoline-2-carboxaldehyde with primary amine.

With lipoic acid moiety, the modified mutant RNase A still has some possibility of nonspecifically binding onto Au nanoparticles. In order to find the optimized RNase A loading conditions with enzymes binding onto Au nanoparticle exclusively via gold-sulfur bond, RNase A loading conditions was studied. Wild type RNase A was used as a model enzyme and the effects of different additive molecules on enzymes' nonspecific binding was evaluated. Three additive molecule candidates, citrate, p-toluenesulfonate and tween 20 were chosen, because they only weakly interact with Au NPs and have no interference on thiol-containing ligands' binding. For quantifying the amount of RNase A on Au nanoparticles, the Au core was dissolved with KCN and released RNase A were measured with CBQCA Protein Quantitation Kit (ThermoFisher Scientific) following manufacturer's instructions. This kit quantify the protein concentration based on the fluorescence signal generated by the reaction between 3-(4-carboxybenzoyl)quinoline-2-carboxaldehyde and the primary amine of protein molecules (Scheme 6, FIG. 37).

None of the three additive molecules alone could totally suppress the nonspecific binding of wild type RNase A onto Au nanoparticles. For citrate, the number of RNase A bound on one Au nanoparticle decreased from 15.9 to 7.30 with citrate concentration increased to 50.0 mM. Further elevating citrate concentration up to 200 mM did not lead to less nonspecific binding, instead, it promoted more RNase A (13.9 per one Au nanoparticle) nonspecifically bind onto Au nanoparticle (Table 3). Similarly, as the P-toluenesulfonate concentration gradually increased to 100 mM, the number of wild type RNase A nonspecifically bound on one Au nanoparticle gradually decreased from 16.3 to 8.01 (Table 3). With further increased P-toluenesulfonate concentration up to 200 mM, the number of wild type RNase A bound on Au Nanoparticle remains to be 8.33. Tween 20 outperformed citrate and P-toluenesulfonate, and the number of RNase A per Au nanoparticle was reduced to 2.00 at concentration of 1.25% (Table 4), but still couldn't completely suppress the nonspecific binding. By combining 1.25% tween 20 with 50.0 mM citrate, no RNase A molecules were detected bound on Au nanoparticles, implying the almost complete suppression of RNase A's nonspecific binding. Thus, 1.25% tween 20 with 50.0 mM citrate was used later on during the loading of lipoic acid tagged mutant RNase A onto Au nanoparticles.

TABLE 3

Number of wild type RNase A per one Au nanoparticle under different concentration of citrate or P-toluenesulfonate as additives (with 0.0100% tween 20).

| | Number of RNase A/Au nanoparticle | |
| --- | --- | --- |
| Additive concentration | Citrate as additive | P-toluenesulfonate as additive |
| 0.00 mM | 15.9 ± 0.790 | 16.3 ± 1.03 |
| 10.0 mM | 11.7 ± 0.310 | 10.7 ± 0.946 |
| 25.0 mM | 7.40 ± 0.725 | 10.4 ± 0.635 |
| 50.0 mM | 7.30 ± 0.554 | 8.94 ± 0.938 |
| 100 mM | 8.98 ± 0.420 | 8.01 ± 1.11 |
| 150 mM | 10.1 ± 0.885 | 7.95 ± 0.836 |
| 200 mM | 13.9 ± 0.883 | 8.33 ± 0.735 |

TABLE 4

Number of wild type RNase A per one Au nanoparticle under different concentration of tween 20 as additives.

| | Number of RNase A/Au nanoparticle | |
| --- | --- | --- |
| Tween 20 concentration | With 0.00 mM citrate | With 50.0 mM citrate |
| 0.00200% | 38.0 ± 0.637 | 15.2 ± 0.637 |
| 0.0100% | 14.7 ± 1.08 | 7.31 ± 0.550 |
| 0.0250% | 11.6 ± 0.872 | 2.97 ± 1.14 |
| 0.0500% | 11.8 ± 0.165 | 2.81 ± 1.08 |
| 0.250% | 9.66 ± 0.623 | 2.18 ± 0.942 |
| 1.25% | 1.95 ± 1.03 | 0.00 ± 0.729 |

Example 12 Demonstration of Nanozyme IIa with Capturer 1 DNA of Different Spacers Nanozyme IIa was prepared using capturer 1 DNA containing PEG or 9 adenine nucleotides (PA) as spacers between Au nanoparticle and capture DNA (All capturer sequences used in example nanozymes are listed in Table 1). In order to quantify the actual oligonucleotide loading density on Au nanoparticles, the Au core of 1.00 nM nanozyme with either PEG or $PA_9$ spacer capture DNA was dissolved by KCN and the released oligonucleotide was respectively measured using Quant-iT™ OliGreen™ ssDNA Assay Kit (ThermoFisher Scientific) following manufacturer's instructions. This kit quantifies oligonucleotides concentration based on the fluorescence signal generated by OliGreen™ dye molecules bound on oligonucleotides (excitation: 480 nm; emission: 515 nm).

Figure 21A:
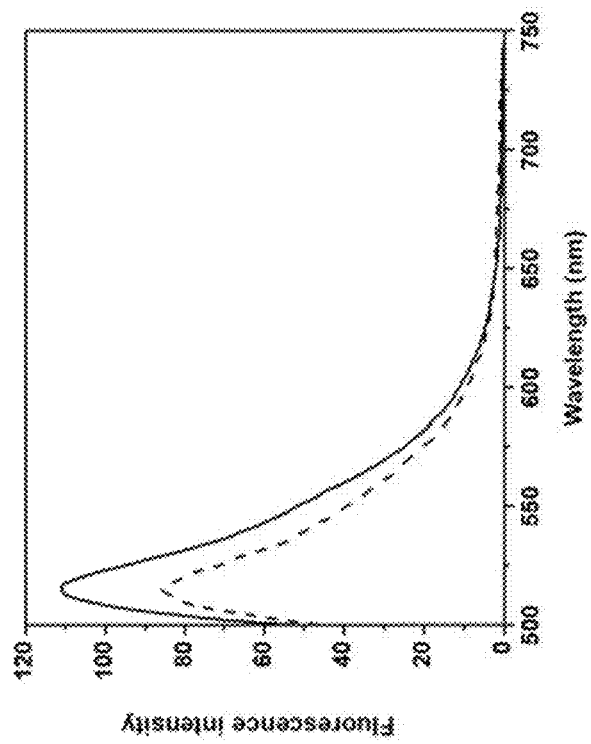
FIG. 21A shows fluorescence spectrum of OliGreen™ dye bound PEG (solid line) and PA9 spacer (dashed line) capturer 1 DNA released from 1.00 nM nanozyme IIa. The average number of oligonucleotide per one Au nanoparticle was 95.0±7.98 for PEG spacer capture DNA and 49.2±9.10 for PA9 spacer capture DNA.
Figure 21B:
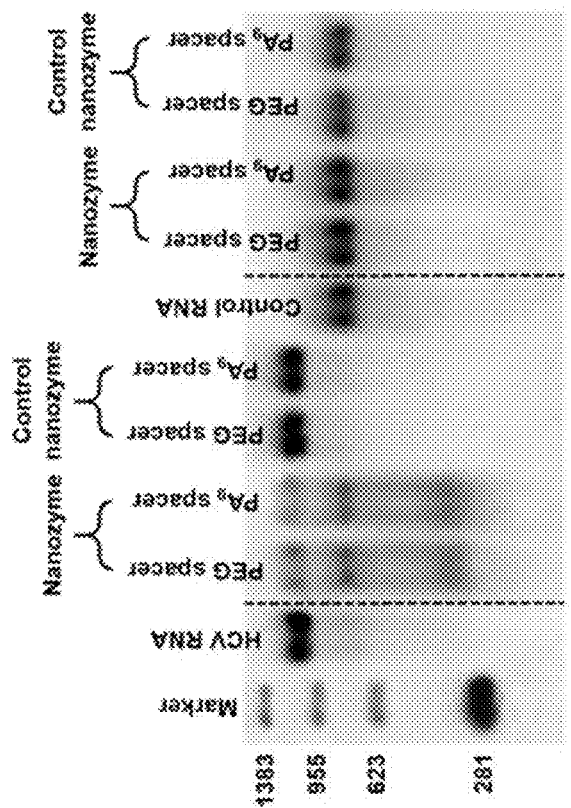
FIG. 21B shows ribonuclease activity tests for assessing the target selectivity of nanozyme IIa with PEG or PA9 spacer capture DNA.

Because of the strong electrostatic repulsion between adjacent oligonucleotides near Au surface, lower capture DNA density was found for nanozyme of $PA_9$ spacer capture DNA (49.2±9.10) when comparing with nanozyme of PEG spacer capture DNA (95.0±7.98) (FIG. 21A). This is in accordance with reported data (Hurst, S J, et al. Anal Chem. 2006 78:8313-8318). Electrophoresis analysis showed that both types of nanozyme presented strong degradation against target HCV RNA segment while almost no degradation was detected for control RNA segment, suggesting their excellent target selectivity (FIG. 21B). The nanozyme's target selectivity was further confirmed by the results that control nanozymes with control capture DNA, either PEG or $PA_9$ spacer, did not show catalytic activity toward neither target nor control RNA segments. Thus, these results demonstrate that nanozyme IIa with either PEG or $PA_9$ spacer capture DNA was capable of selectively degrade its target RNA.

Example 13. Demonstration of Nanozyme IIa with PEG-Spacer Capturer 1 DNA of Single/Double Thiol Anchor Nanozyme IIa was prepared using PEG-spacer capturer 1 DNA containing single or double thiol anchor at the 3' end. First of all, the oligonucleotide density on Au nanoparticle was analyzed in a similar way as in Example 5 (FIG. 22A). Nanozyme with double thiol anchor capture DNA presented slightly higher oligonucleotide density (104±5.23) than the one with single thiol capture DNA (95.0±7.98). This is probably due to the higher Au affinity from the double thiol anchor. Electrophoresis analysis showed that nanozyme with either single or double thiol anchor capture DNA could selectively degrade target HCV RNA segments without noticeable difference (FIG. 22B), implying their similar catalytic activity and target selectivity.

Example 14. Evaluation of Nanozyme IIa with Single Thiol Anchor PEG-Spacer Capturer DNA of Different Length (Capturer 1, 2, 3)

Nanozyme IIa was prepared using single thiol anchor PEG-spacer capturer DNA of different length (capturer 1: 18 bases complimentary binding, capturer 2: 15 bases complimentary binding, capturer 3: 12 bases complimentary binding with target HCV RNA). All three types of capturer DNA are capable of forming stable complimentary binding with target HCV RNA segment under physiological conditions.

Figures 23A, 23B:
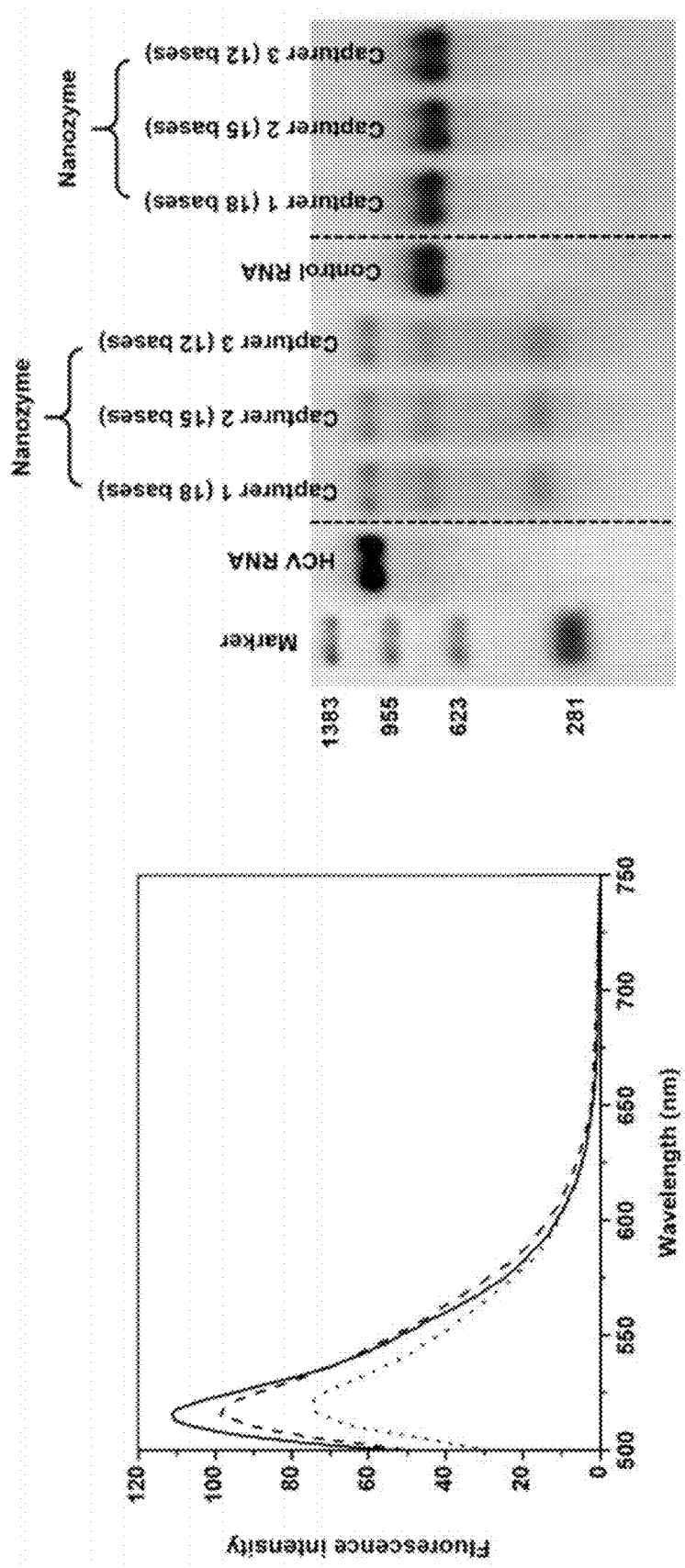
FIG. 23A shows fluorescence spectrum of OliGreen™ dye bound 18 bases capturer 1 (solid line), 15 bases capturer 2 (dashed line) and 12 bases capturer 3 (dotted line) DNA released from 1.00 nM respective nanozyme IIa. The average number of oligonucleotide per one Au nanoparticle was 95.0±7.98 for capturer 1, 99.2±4.01 for capturer 2 and 100±8.13 for capturer 3.
FIG. 23B shows ribonuclease activity tests for assessing the target selectivity of nanozyme IIa with PEG-spacer single thiol anchor capturer 1, 2 and 3 DNA.

With Quant-iT™ OliGreen™ ssDNA Assay Kit (ThermoFisher Scientific), similar oligonucleotide loading density were found for three types of nanozyme with capturer 1, 2 and 3 (FIG. 23A). The decreased fluorescence intensity with shortened capturer DNA was probably due to the less OliGreen dye bounding capacity for DNA with less nucleotides. Electrophoresis analysis showed that all three types of nanozymes with varied length of capturer DNA had good selectivity on degrading target HCV RNA segments while leaving control RNA segment almost untouched. This result proves that even with capturer DNA of only 12 bases, nanozyme still maintains excellent activity and target selectivity.

Figure 24B:
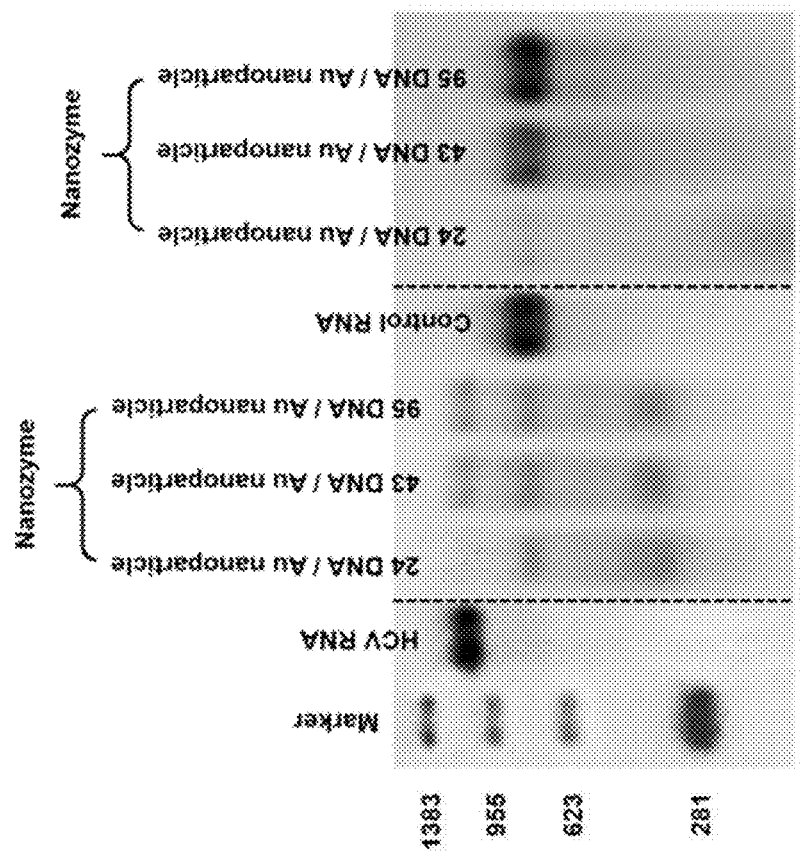
FIG. 24A shows fluorescence spectrum of OliGreen™ dye bound capture DNA from 1.0 nM nanozyme IIa of low (24±6.3 DNA/Au nanoparticle, dotted), medium (43±6.5 DNA/Au nanoparticle, dashed) and high (95±8.0 DNA/Au nanoparticle, solid) oligonucleotide density.
Figure 24A:
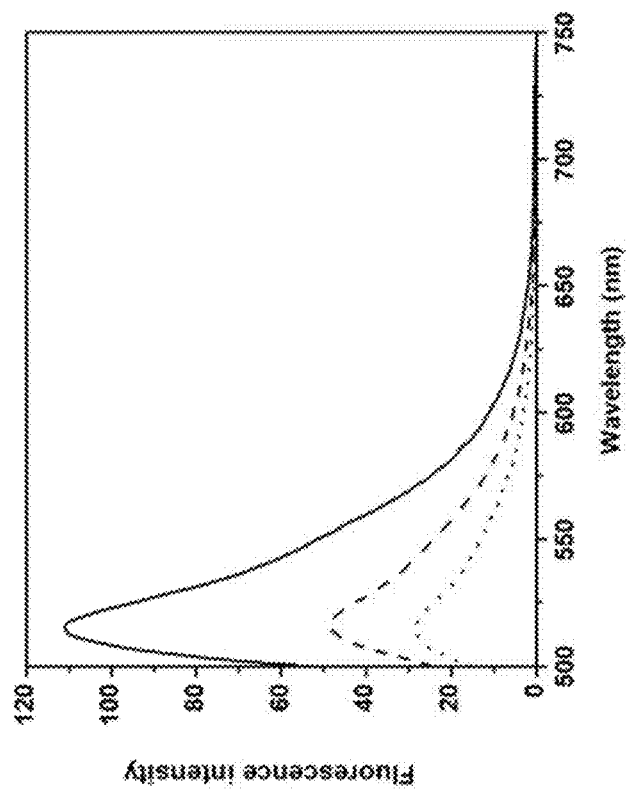

Example 15. Evaluation of Nanozyme IIa with Single Thiol Anchor PEG-Spacer Capturer 1 DNA of Different Loading Density Nanozyme IIa with low, medium, high oligonucleotide density were prepared with single thiol anchor PEG-spacer capturer 1 DNA. Using Quant-iT™ OliGreen™ ssDNA Assay Kit (ThermoFisher Scientific), the actual oligonucleotide density was found to be 24, 43, 95 DNA per one Au nanoparticle (FIG. 24A). Electrophoresis analysis showed with low oligonucleotide density (24 DNA per Au nanoparticle), the corresponding nanozyme had very strong activity toward both target and control RNA segment without any selectivity (FIG. 24B). As more capture DNA being loaded, nanozyme with medium oligonucleotide density (43 DNA per Au nanoparticle) showed slightly decreased activity but noticeably improved target selectivity. Only with high oligonucleotide density (95 DNA per Au nanoparticle) would the nanozyme have the optimized activity and selectivity on target RNA. These results proved that densely loaded capture DNA was essential for preparing nanozyme possessing selective target RNA degrading capability.

Example 16. Preparing an HCV NZ with Varied LA-A19C Loading Density

Figure 25B:
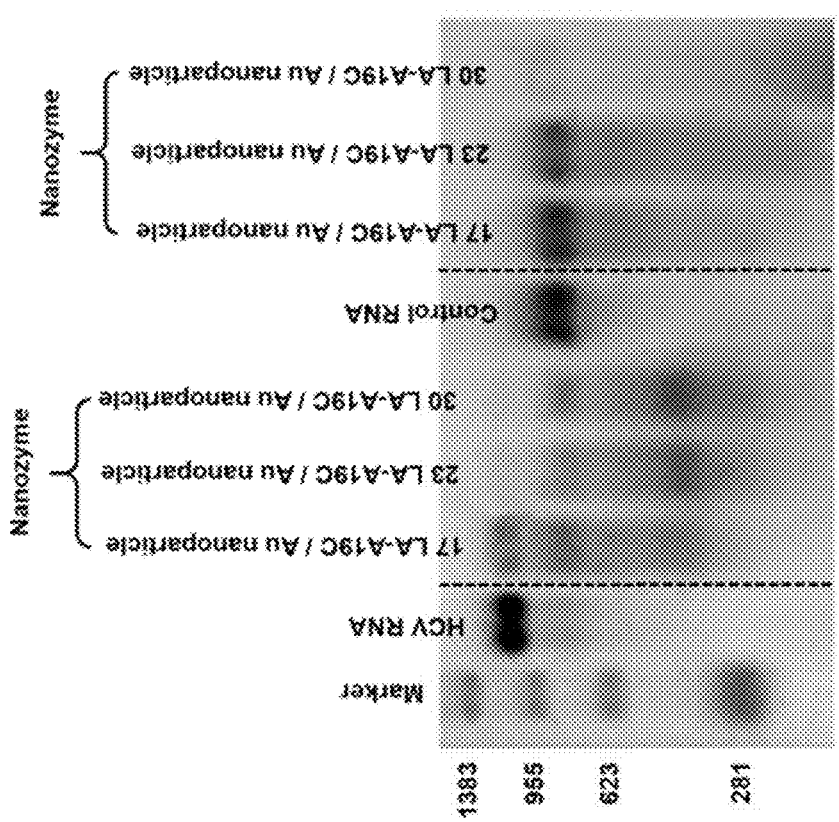
FIG. 25B shows ribonuclease activity tests for assessing the target selectivity of nanozyme IIa with varied LA-A19C loading density.
Figure 25A:
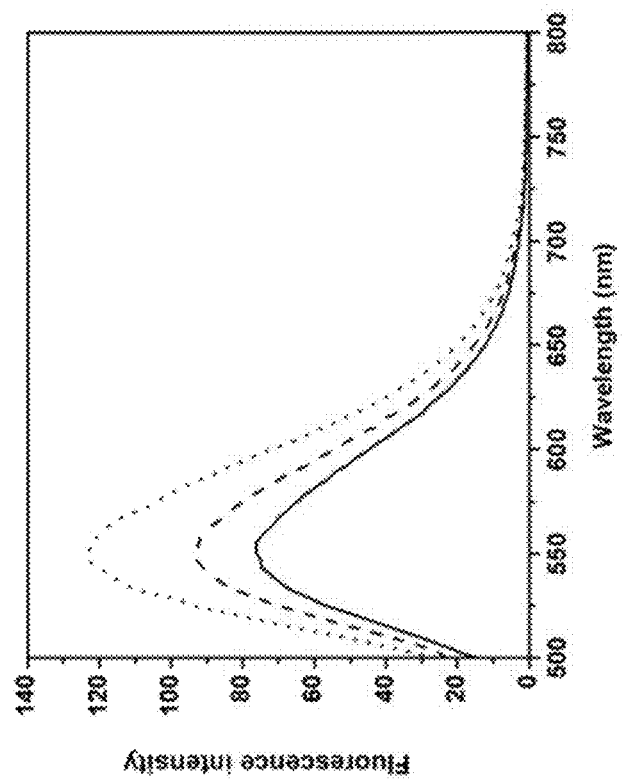
FIG. 25A shows fluorescence spectrum of tagged LA-A19C from nanozyme IIa of varied loading densities.

Nanozyme IIa of varied LA-A19C loading density were prepared. With the CBQCA Protein Quantitation Kit (ThermoFisher Scientific) mentioned in Example 11, the actual amount of RNase A in nanozyme were determined to be 17, 23 and 30 LA-A19C/Au nanoparticle (FIG. 25A). Electrophoresis analysis showed only the nanozyme with 17 LA-A19C per Au nanoparticle exhibited selective degrading of target HCV RNA segments. With more LA-A19C loaded on Au nanoparticle (23 RNase A per Au nanoparticle), the corresponding nanozyme showed stronger activity on both target and control RNA segment, indicating its loss of selectivity. When the number of LA-A19C per Au nanoparticle further increase to 30, the corresponding nanozyme showed no any selectivity as both target and control RNA segments were degraded into highly smeared bands. These results proved the importance of proper RNase A's loading amount for nanozyme's selectivity. More than 20 RNase A per Au nanoparticle would lead to insufficient coverage and protection of enzyme by capturer DNA, which would inevitably result in poor selectivity.

Example 17. Demonstration of Nanozyme IIb with Two Types of Capturer DNA

Figure 26B:
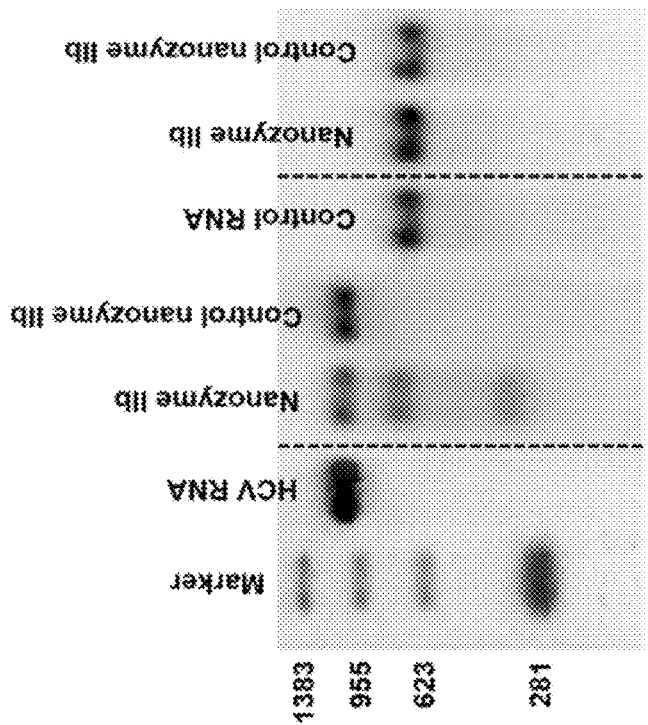
FIG. 26B shows ribonuclease activity tests for assessing the target selectivity of nanozyme IIb.
Figure 26A:
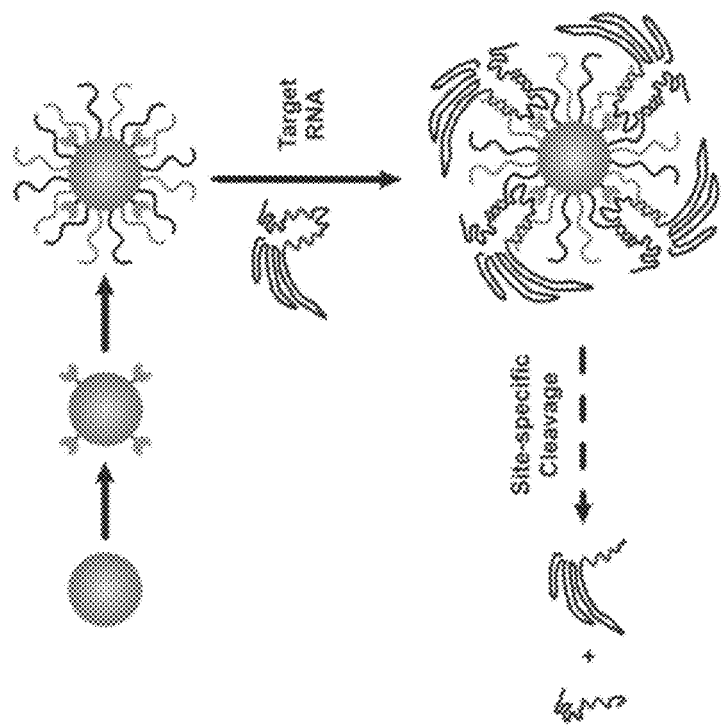
FIG. 26A is a schematic representation of nanozyme IIb with two types of capturer DNA.

Nanozyme IIb was prepared by co-loading two types of capturer DNA with 9 bases and 7 bases complimentary binding with target HCV RNA respectively (FIG. 26A). Electrophoresis analysis showed that nanozyme IIb selectively degraded target HCV RNA segments but not control RNA segments, suggesting its excellent target selectivity (FIG. 26B). When control capture DNA instead of capture DNA were used, the prepared control nanozyme exhibited no activity on neither target HCV nor control RNA. Thus, these results demonstrated that nanozyme IIb with two types of capturer DNA was capable of selectively degrade its target RNA.

Figure 27B:
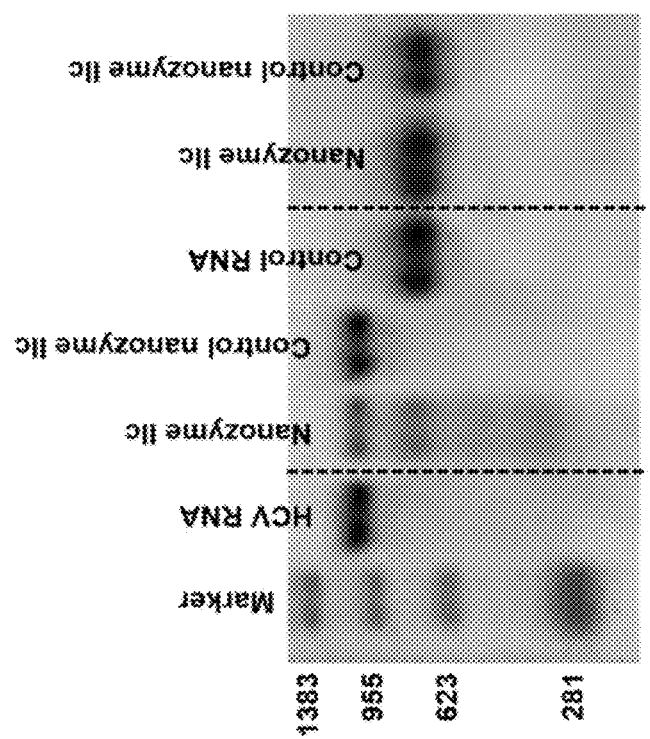
FIG. 27B shows ribonuclease activity tests for assessing the target selectivity of nanozyme IIc.
Figure 27A:
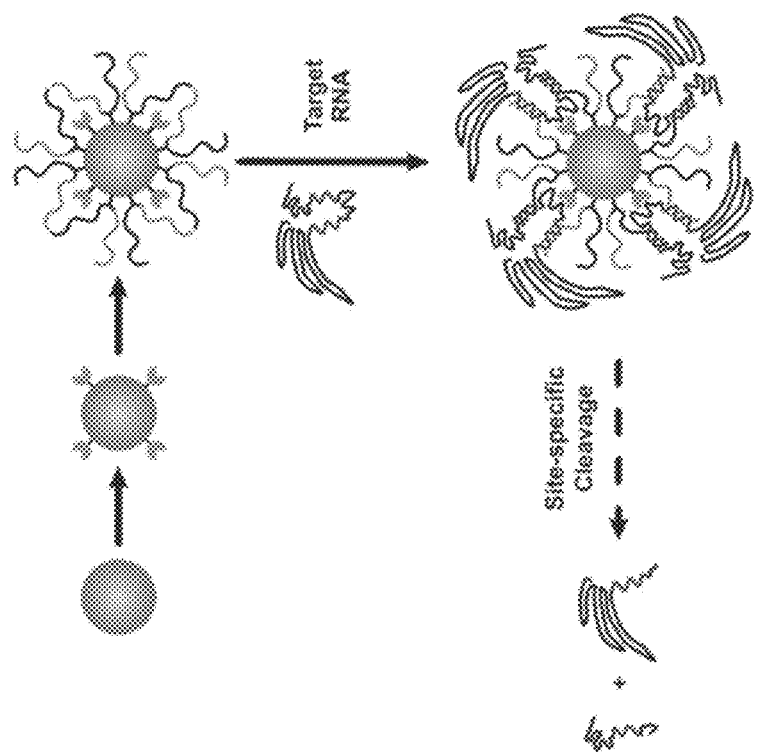
FIG. 27A is a schematic representation of nanozyme IIc with branched double-sequenced capturer DNA.

Example 18. Demonstration of Nanozyme IIc with Branched Double-Sequenced Capturer DNA Nanozyme IIc was prepared with branched double-sequenced capturer DNA (FIG. 27A). Electrophoresis analysis showed that nanozyme IIc selectively degrade target HCV RNA segments, indicating its excellent target selectivity (FIG. 27B). Moreover, with branched double-sequenced control capturer DNA not complimentary to neither target nor control RNA segments, the prepared control nanozyme exhibited no activity. Thus, these results demonstrated Nanozyme IIc's capability of target RNA selective degradation.

Example 19. Demonstration of Turning Off Nanozyme IIa's Activity with Blocker DNA A Blocker DNA experiment was designed and performed to further study the structure and RNA degradation of the prepared nanozyme (FIG. 28A). The densely packed oligonucleotides in nanozyme serve as both RNase coverage, shielding their activity from nonselective degradation, and target capture, forming sequence specific complementary binding with target RNA, thus enabling nanozyme's target selective RNA degradation. In order to confirm the importance of complementary binding between target RNA and capturer DNA, the nanozyme IIa was pre-incubated with blocker DNA which is in full complementary to capturer DNA. As all capturer DNA being occupied by blocker DNA, the resulted nanozyme could not bind with neither target nor control RNA segment, therefore would not present any degradation effect.

Figure 28B:
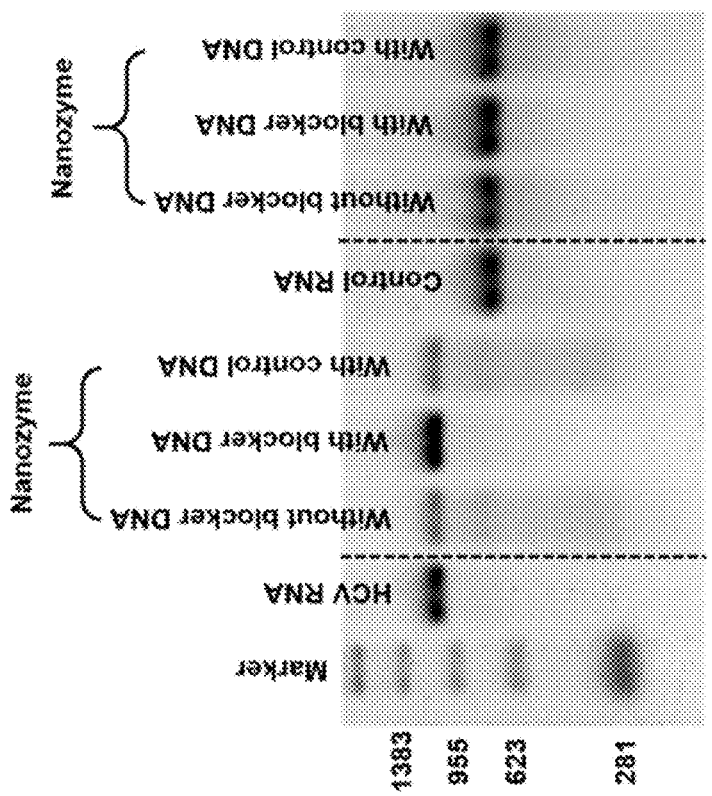
FIG. 28B shows ribonuclease activity tests for assessing the target selectivity of nanozyme IIa with or without blocker DNA.
Figure 28A:
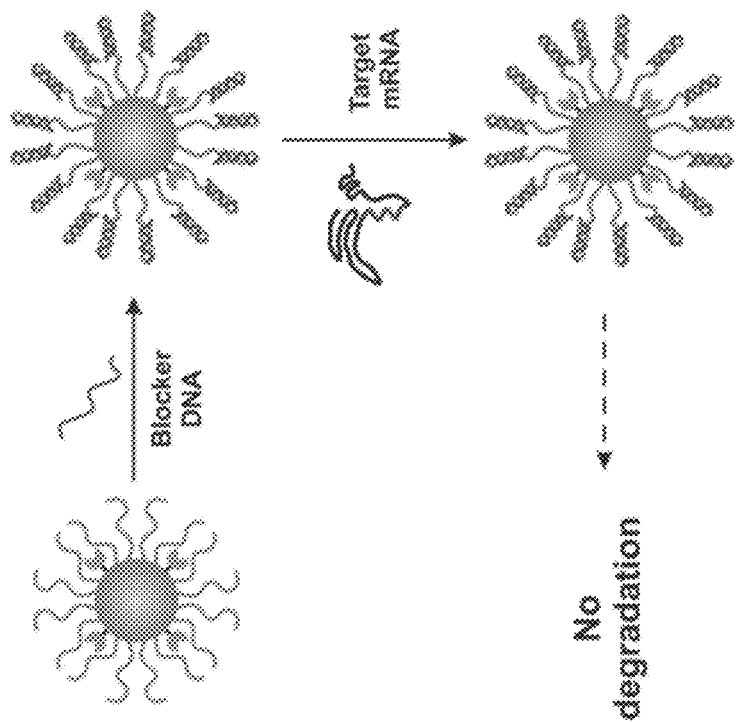
FIG. 28A is a schematic representation of nanozyme IIa's activity being turned off by blocker DNA.
Figure 29B:
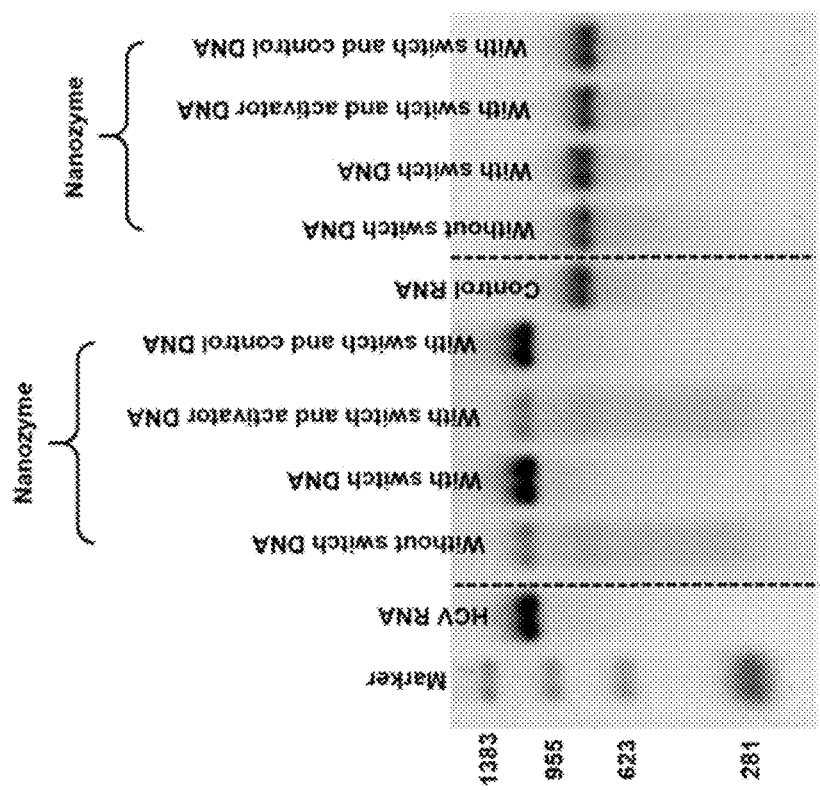
FIG. 29B shows ribonuclease activity tests for assessing on/off switchable nanozyme.
Figure 29A:
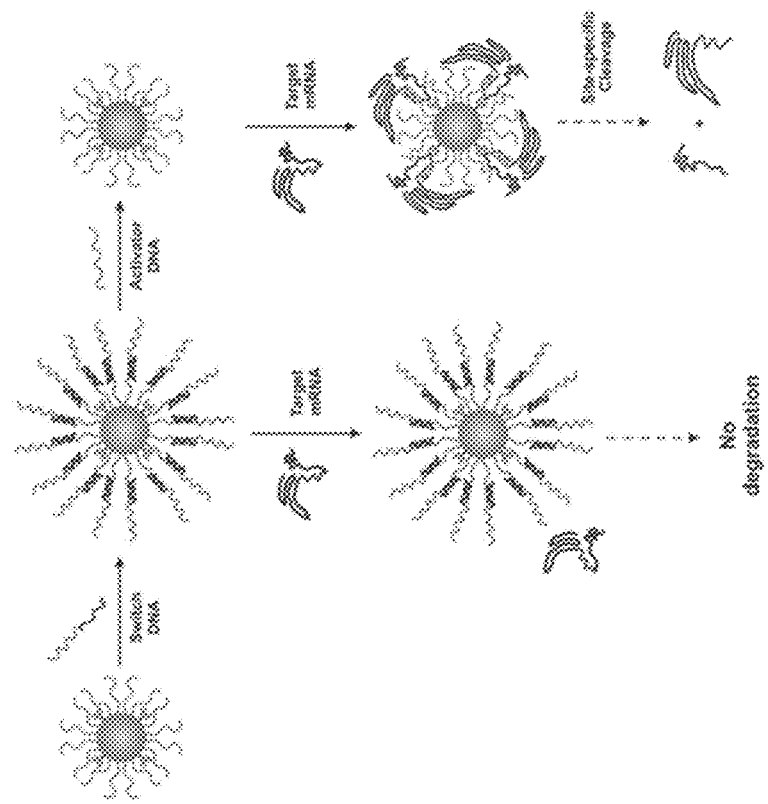
FIG. 29A is a schematic representation of on/off switchable nanozyme with switch and activator DNA.

Electrophoresis analysis showed that, indeed, nanozymes pre-incubated with blocker DNA presented almost no degradation activity toward neither target HCV nor control RNA segments (FIG. 28B). On the contrary, nanozymes without blocker DNA or pre-incubated with control DNA which has no stable complimentary binding with capturer DNA exhibited strong and selective degradation on target RNA segment. Accordingly, it was concluded that by forming complimentary binding with capturer DNA, blocker DNA could prevent the further complementary binding of target RNA strand, therefore shutting off NZ's activity.

Example 20. Demonstration of on/Off Switchable Nanozyme IIa with Switch and Activator DNA For enabling on/off switchable nanozyme, a switch DNA was designed (FIG. 12(A)). It is composed of two parts. The first part contains 11 bases in complimentary with capturer DNA of nanozyme, while the second part contains dangling 20 adenine bases. When incubated with nanozyme, switch DNA could stably bind with nanozyme's capturer DNA, thus switch off its activity. To switch on nanozyme's activity, an activator DNA fully complimentary to switch DNA was designed. When added into switched-off nanozyme, the activator DNA could peel off switch DNA bound on capturer DNA via competitive complimentary binding, therefore switching on nanozyme's activity.

Electrophoresis analysis showed that, after being incubated with switch DNA, the nanozyme presented almost no activity on neither target nor control RNA, indicating its activity being successfully switched off. When activator DNA was added, target HCV RNA was selectively degraded, suggesting its activity was switched on. When control instead of activator DNA was used, the nanozyme remains inactive on neither target nor control RNA. These results demonstrated that nanozyme's activity was on/off switchable with switch and activator DNA.

Example 21. Demonstration of Hollow Nanozyme IIa

Figure 30B:
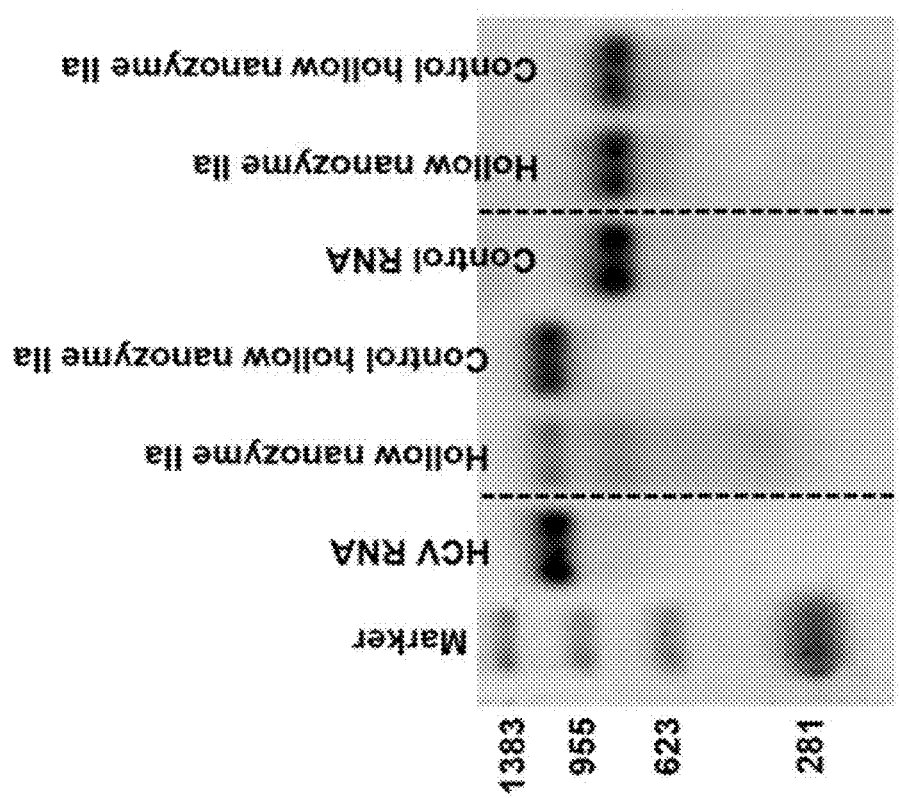
FIG. 30B shows ribonuclease activity tests for assessing the target selectivity of hollow nanozyme IIa.
Figure 30A:
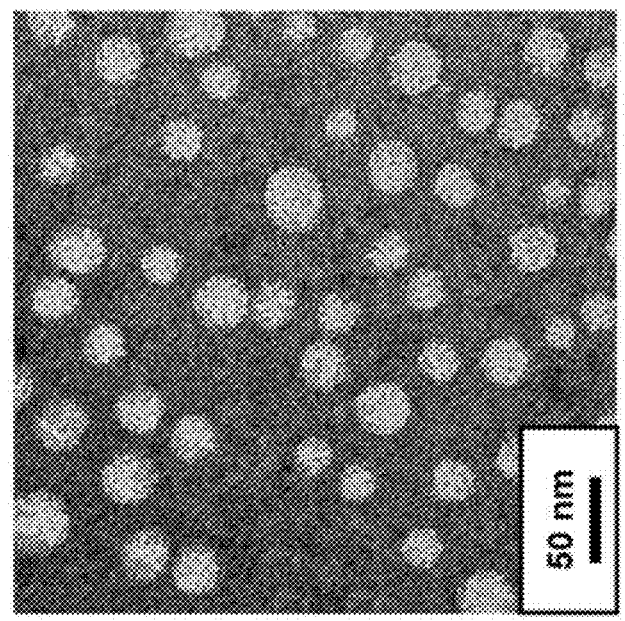
FIG. 30A is a transmission electron microscope image of hollow nanozyme IIa with uranium acetate negative staining.

Hollow nanozyme IIa was synthesized using RNase A and capture DNA modified with polymerizable oligos. After polymerization, the Au core was removed by KCN and purified by extensive dialysis. The structure of hollow nanozyme IIa was characterized by transmission electron microscope with uranium acetate negative staining (FIG. 30A). With polymerized oligo shell, hollow nanozyme IIa showed an average diameter of about 50 nm. This is slightly larger than its size before KCN dissolving, probably due to the structural swallowing without the inorganic core.

Electrophoresis analysis showed that hollow nanozyme IIa could selectively degrade target HCV RNA segment like nanozyme with Au nanoparticle core (FIG. 30B), indicating its target selective activity. On the contrary, control hollow nanozyme IIa with capturer DNA not complimentary to neither target nor control RNA segments showed no activity. Thus these results proved that target selective nanozyme could be made with its inorganic core removed.

Figure 31B:
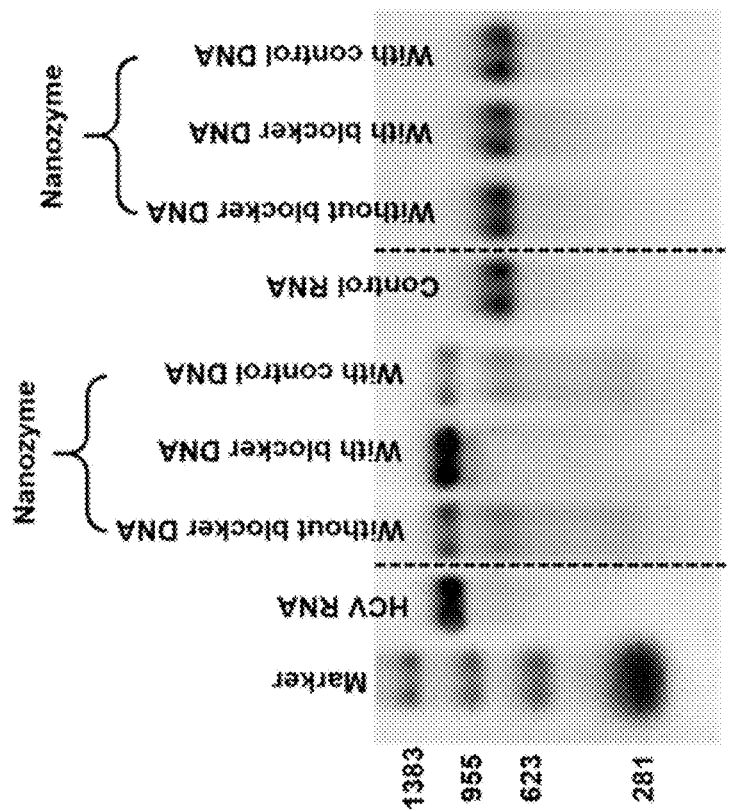
FIG. 31B shows ribonuclease activity tests for assessing the target selectivity of hollow nanozyme IIa with or without blocker DNA.
Figure 31A:
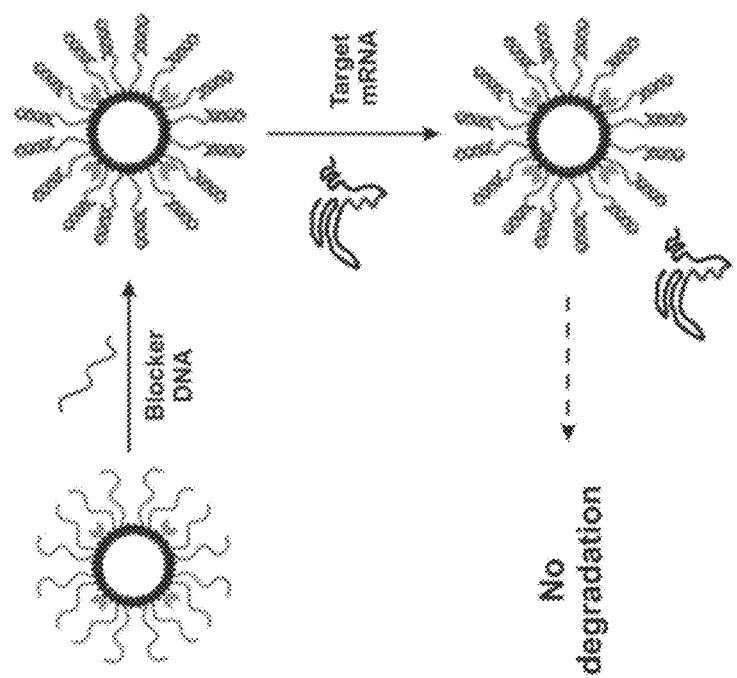
FIG. 31A is a schematic representation of hollow nanozyme IIa's activity being turned off by blocker DNA.

Example 22. Demonstration of Turning Off Hollow Nanozyme IIa's Activity with Blocker DNA Similar to nanozyme IIa with Au core, hollow nanozyme IIa's activity could also be turned off with blocker DNA (FIG. 31A). Electrophoresis analysis showed that, hollow nanozymes pre-incubated with blocker DNA presented almost no degradation activity toward neither target HCV nor control RNA segments (FIG. 31B). On the contrary, hollow nanozymes without blocker DNA or pre-incubated with control DNA which has no stable complimentary binding with capture DNA exhibited strong and selective degradation on target HCV RNA segment. Accordingly, it was concluded that, similar to nanozyme with Au nanoparticle core, hollow nanozyme's activity also could be effectively shut off by blocker DNA.

Example 23. Demonstration of on/Off Switchable Hollow Nanozyme Li with Switch and Activator DNA Similar to nanozyme IIa with Au core, hollow nanozyme IIa's activity was also proven to be on/off switchable with switch and activator DNA (FIG. 32A). Electrophoresis analysis (FIG. 32B) showed that, after being incubated with switch DNA, the hollow nanozyme presented almost no activity on neither target nor control RNA, indicating its activity being successfully switched off. When activator DNA was added, hollow nanozyme's became active again and target HCV RNA was selectively degraded. On the contrary, with control instead of activator DNA being added, the hollow nanozyme remains inactive on neither target nor control RNA. These results demonstrated that, similar to nanozyme with Au nanoparticle core, hollow nanozyme's activity was also on/off switchable with switch and activator DNA.

Figure 38:
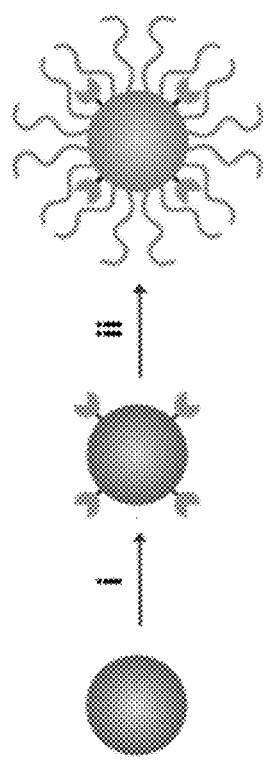
FIG. 38 is a schematic representation of nanozyme IIa preparation.

Example 24. Demonstration of Nanozyme and Hollow Nanozyme IIa with Capturer DNA Targeting GPC3 RNA Nanozyme IIa Preparation Nanozyme IIa was prepared in two steps (FIG. 38). First of all, 1 nmol mutant RNase A with double thiol anchor (LA-A19C) were treated with 50 mM DTT in 0.2 M phosphate buffer (pH 8.0) for 30 min to cleave the disulfide bond and purified by NAP-5 desalting column. Such LA-A19C were immediately added to 2 mL Au NPs solution (0.01 nmol) containing 0.5% Tween 20 and 150 mM citrate at pH 7.4. After overnight shaking, the Au-LA-A19C NPs was purified by centrifuge to remove excess unbound LA-A19C. Secondly, 6 nmol capturer DNA was treated by 0.1 M DTT in 0.2 M phosphate buffer (pH 8.0) to cleave the disulfide bond and purified by NAP-5 desalting column. Such DTT treated capturer DNA was added into Au-LA-A19C NPs and the NaCl concentration was gradually increased to 0.6 M during 8 h and then further shaken overnight. The resultant nanozyme IIa was purified by repetitive centrifuge using 1×PBS and redispersed in 10 mM PB for further use.

Hollow Nanozyme IIa Preparation

Figure 39:
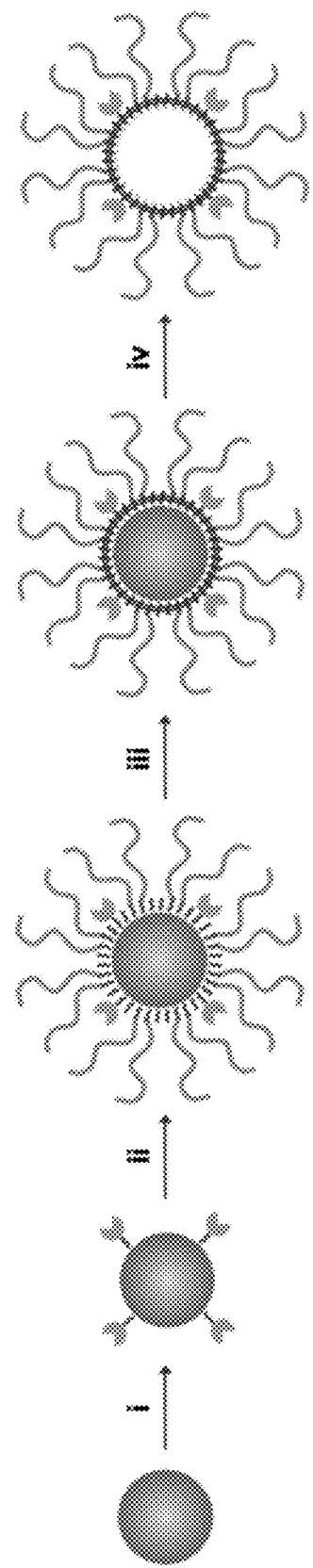
FIG. 39 is a schematic representation of hollow nanozyme IIa preparation.
Figure 42:
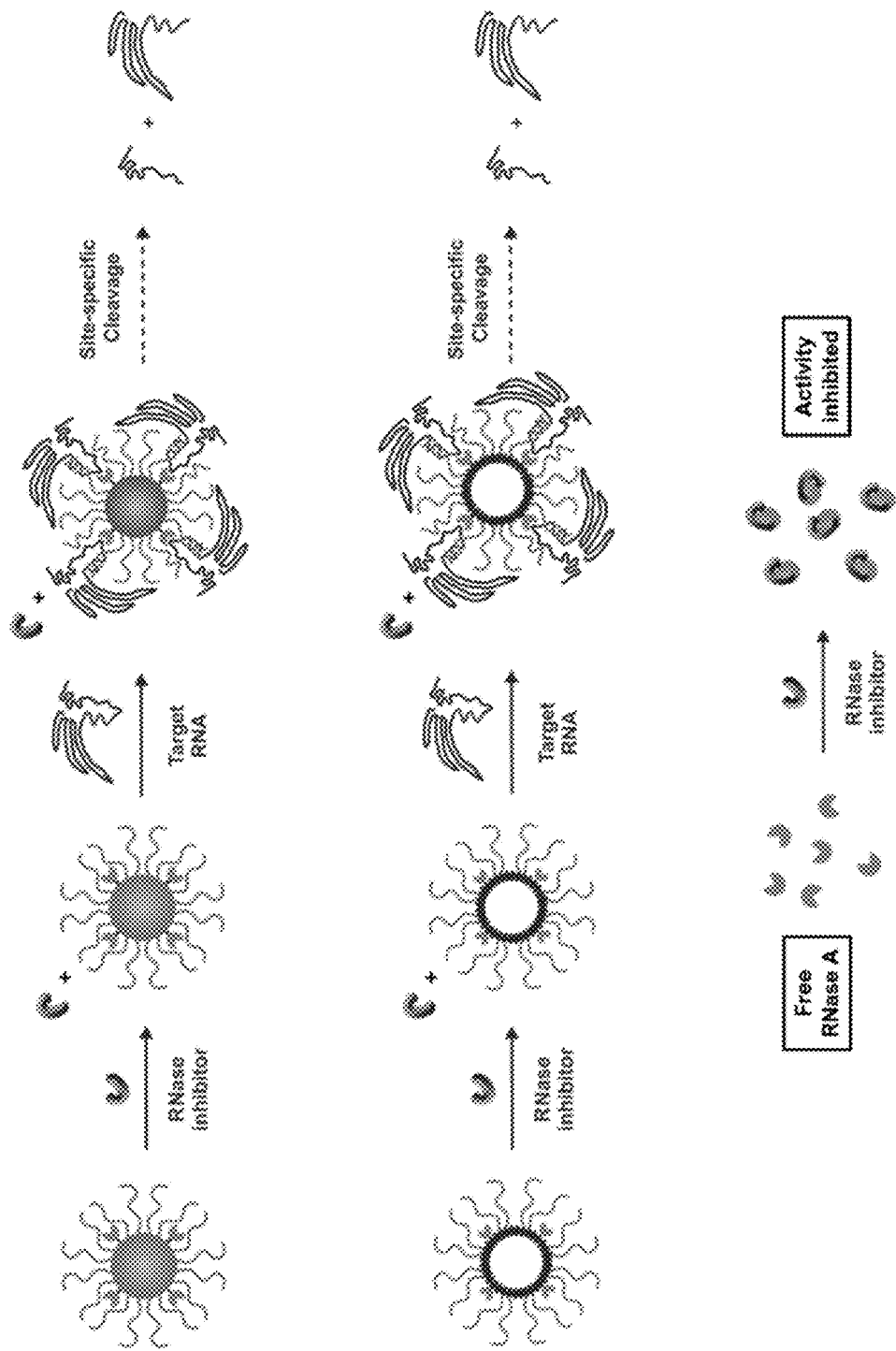
FIG. 42 is a schematic representation of nanozyme and hollow nanozyme's resistance to RNase inhibitor.

Hollow nanozyme IIa was prepared in four steps (FIG. 39). First of all, 1 nmol mutant RNase A with polymerizable spacer and double thiol anchor (P-LA-A19C) were treated with 50 mM DTT in 0.2 M phosphate buffer (pH 8.0) to cleave the disulfide bond and purified by NAP-5 desalting column. Such P-LA-A19C were immediately added to 2 mL Au NPs solution (0.01 nmol) containing 0.5% Tween 20 and 150 mM citrate at pH 7.4. After overnight shaking, the Au-P-LA-A19C NPs was purified by centrifuge to remove excess unbound P-LA-A19C. Secondly, 10 nmol capturer DNA with polymerizable spacer was treated by 0.1 M DTT in 0.2 M phosphate buffer (pH 8.0) to cleave the disulfide bond and purified by NAP-5 desalting column. Such DTT treated polymerizable capturer DNA was added into Au-P-LA-A19C NPs. The solution temperature was then elevated to 60° C. and NaCl concentration was gradually increased to 1 M during 8 h. The solution was shaken under 60C for 48 h to finish the polymerization. The resultant nanozyme was purified by repetitive centrifuge using 1×PBS to remove the excess polymerizable capturer DNA and then treated by 500 mM KCN to dissolve the Au nanoparticle core. The resultant hollow nanozyme IIa was purified by extensive dialysis against 10 mM phosphate buffer.

Ribonuclease Activity Tests for Assessing the Target Selectivity of Nanozyme and Hollow Nanozyme IIa The activity and target selectivity of nanozyme and hollow nanozyme IIa was evaluated by agarose electrophoresis. Briefly, target/control RNA substrate (0.25 µg) was incubated with nanozyme (0.1 nM, 5 µL) in PBS for 30 min at 37° C., then 5 µL formaldehyde loading buffer was added and the solution was heated at 65° C. for 10 min. The solution was immediately put on ice for 2 min and then loaded into 2% agarose gel (prepared with 1× 3-(N-Morpholino)propane sulfonic acid buffer containing 1% formaldehyde). Gel electrophoresis was performed under 65 V for 90 min (BIO-RAD Mini-Sub Cell GT Cell with Power-Pac HC High-Current Power Supply) and SYBR Green II was used to stain the gel.

TABLE 5

Sequence design of RNA molecular/control beacon and capturer/control strands on NZ.

| Name | Sequence |
|---|---|
| Molecular beacon | 5' Cy3-GGU-CUC-GUA-GAC-CGU-GCA-CCA-UGA-GCA-CAC-UUC-CAA-AAC-CCC-AAA-GAA-AAc-gag-acc-Dabcyl 3' (SEQ ID NO: 1 for underlined portion) |
| Control beacon | 5' Cy3-GGU-CUG-GUA-UAC-CGU-GCA-CCA-UGA-GCA-CAC-UUC-CAA-AAC-CCC-AAG-GAA-AAc-gag-acc-Dabcyl 3' (SEQ ID NO: 2 for underlined portion) |
| Nanozyme IIa capturer 1 | 3' HS-(CH$_2$)$_3$-spacer-CCA-GAG-CAT-CTG-GCA-CGT 5' (SEQ ID NO: 3 for underlined portion) |
| Nanozyme IIa control 1 | 3' HS-(CH$_2$)$_3$-spacer-CCA-GAC-CAT-ATG-GCA-CGT 5' (SEQ ID NO: 4 for underlined portion) |
| Nanozyme IIa capturer 2 | 3' HS-(CH$_2$)$_3$-spacer-CCA-GAG-CAT-CTG-GCA 5' (SEQ ID NO: 5 for underlined portion) |
| Nanozyme IIa capturer 3 | 3' HS-(CH$_2$)$_3$-spacer-CCA-GAG-CAT-CTG 5' (SEQ ID NO: 6 for underlined portion) |
| Nanozyme IIa capturer GPC3 | 3' HS-(CH$_2$)$_3$-spacer-CCA-CTA-CTA-CTT-CTA-CTT 5' (SEQ ID NO: 15 for underlined portion) |
| Nanozyme IIa capturer Ebola(-) | 3' HS-(CH$_2$)$_3$-spacer-GTC-TTT-ACG-TTG-CTG-TGG 5' (SEQ ID NO: 16 for underlined portion) |
| Nanozyme IIa capturer Ebola(+) | 3' HS-(CH$_2$)$_3$-spacer-TTT-CAG-CAA-GGA-GCC-ATC 5' (SEQ ID NO: 17 for underlined portion) |
| Nanozyme IIb capturer | C$_1$: 3' spacer-CCA-GAG-CAT-CTG 5' (SEQ ID NO: 7 for underlined portion)<br>C$_2$: 3' spacer-TTT-CTT-T 5' |
| Nanozyme IIb control | C$_1$: 3' spacer-CCA-GAC-CAT-ATG 5' (SEQ ID NO: 8 for underlined portion)<br>C$_2$: 3' spacer-TTC-CTT-T 5' |
| Blocker | 5' Cy3-GGU-CUC-GUA-GAC-CGU-GCA 3' (SEQ ID NO: 9 for underlined portion) |
| Switch | 5' Cy3-GUA-GAC-CGU-GCA-AAA-AAA-AAA-AAA-AAA-AAA-AA 3' (SEQ ID NO: 10 for underlined portion) |
| Activator | 5' TTT-TTT-TTT-TTT-TTT-TTT-TTT-GCA-CGG-TCT-AC 3' (SEQ ID NO: 11 for underlined portion) |

Results

Figure 43:
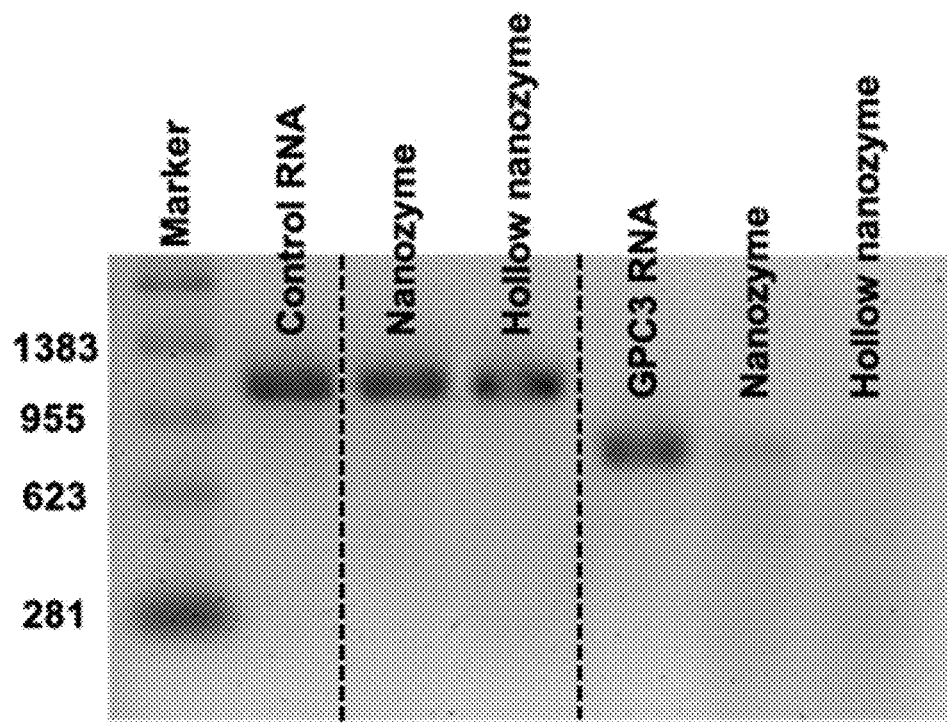
FIG. 43 shows ribonuclease activity tests for assessing the target selectivity of nanozyme and hollow nanozyme IIa with PEG-spacer capturer DNA targeting GPC3 RNA.

Nanozyme and hollow nanozyme IIa were prepared using PEG-spacer capturer DNA targeting GPC3 RNA with double thiol anchor at the 3-end. The activity and selectivity of prepared nanozymes were demonstrated using GPC3 RNA segments as target substrates and HCV RNA segments as control substrates. Electrophoresis analysis (FIG. 43) showed that both nanozyme and hollow nanozyme selectively degrade target GPC3 RNA segments, proving their excellent target RNA specificity.

Example 25. Demonstration of Nanozyme and Hollow Nanozyme IIa with Capturer DNA Targeting Ebola(-)/(+) RNA Establishment of Artificial Ebola Testing Model Based on HCV Because of its extreme fatalness and transmissibility, experiments related with Ebola virus strictly requires biosafety level 4 equivalent containment which is either cabinet laboratories or protective-suit laboratories in isolated areas. There are only a dozen of biosafety level 4 facilities in United States with limited access. In order to overcome this limitation, an artificial Ebola testing model was established based on the intracellular self-replicating HCV RNA replicon. Experiments using this model was allowed to be conducted in biosafety level 2 cabinet following proper rules and regulations.

Figure 40:
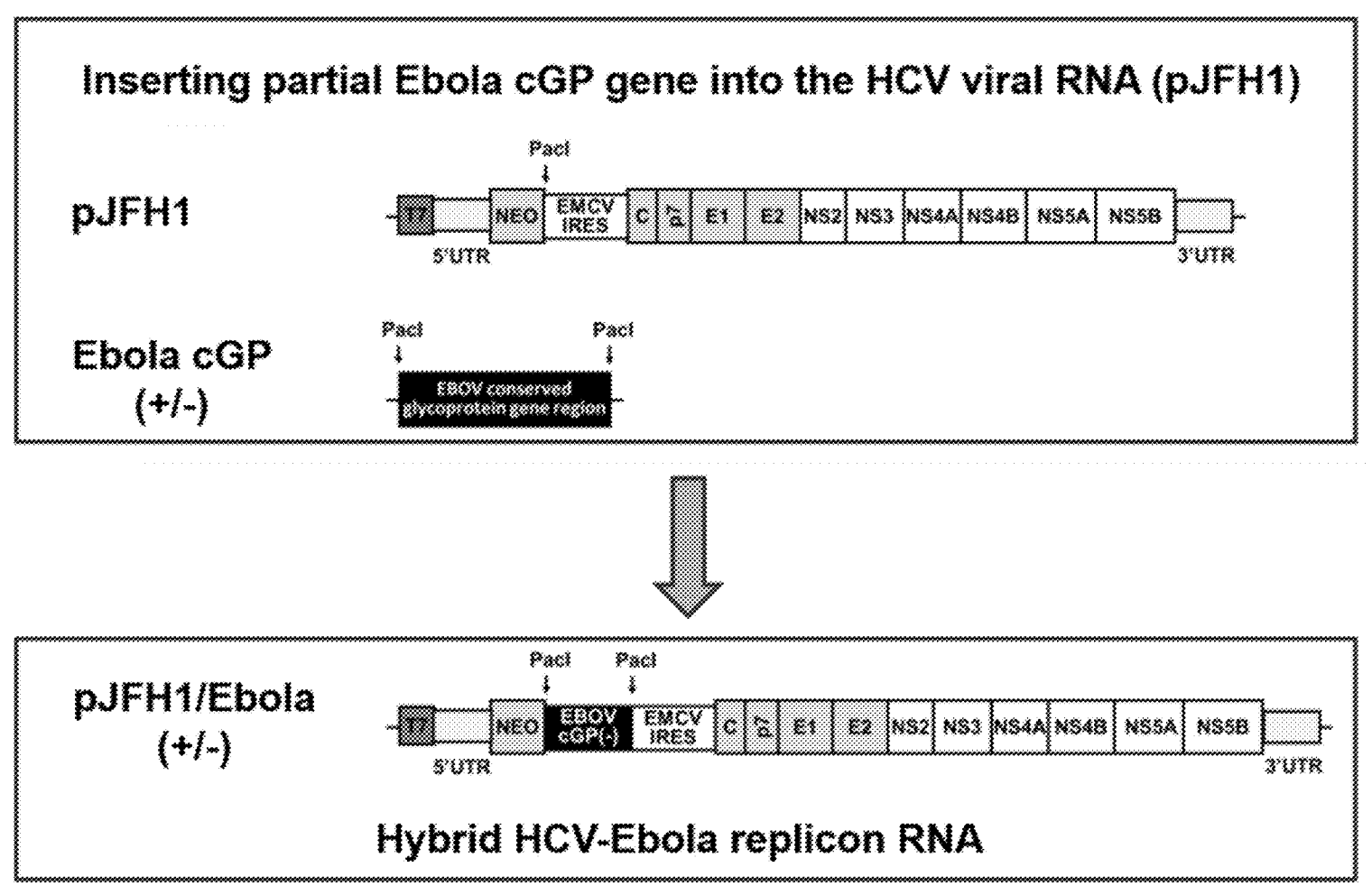

As shown in FIG. 40, by inserting a small piece of Ebola conserved glycoprotein (cGP) gene into HCV RNA replicon, a hybrid HCV-Ebola replicon RNA was obtained. By transfecting such hybrid HCV-Ebola replicon RNA into Huh7.5 cells, a Huh7.5-JFH1/Ebola cell line harboring self-replicating hybrid HCV-Ebola RNA replicon was constructed. Experiments involving this cell line only requires biosafety level 2 containment.

Figure 41:
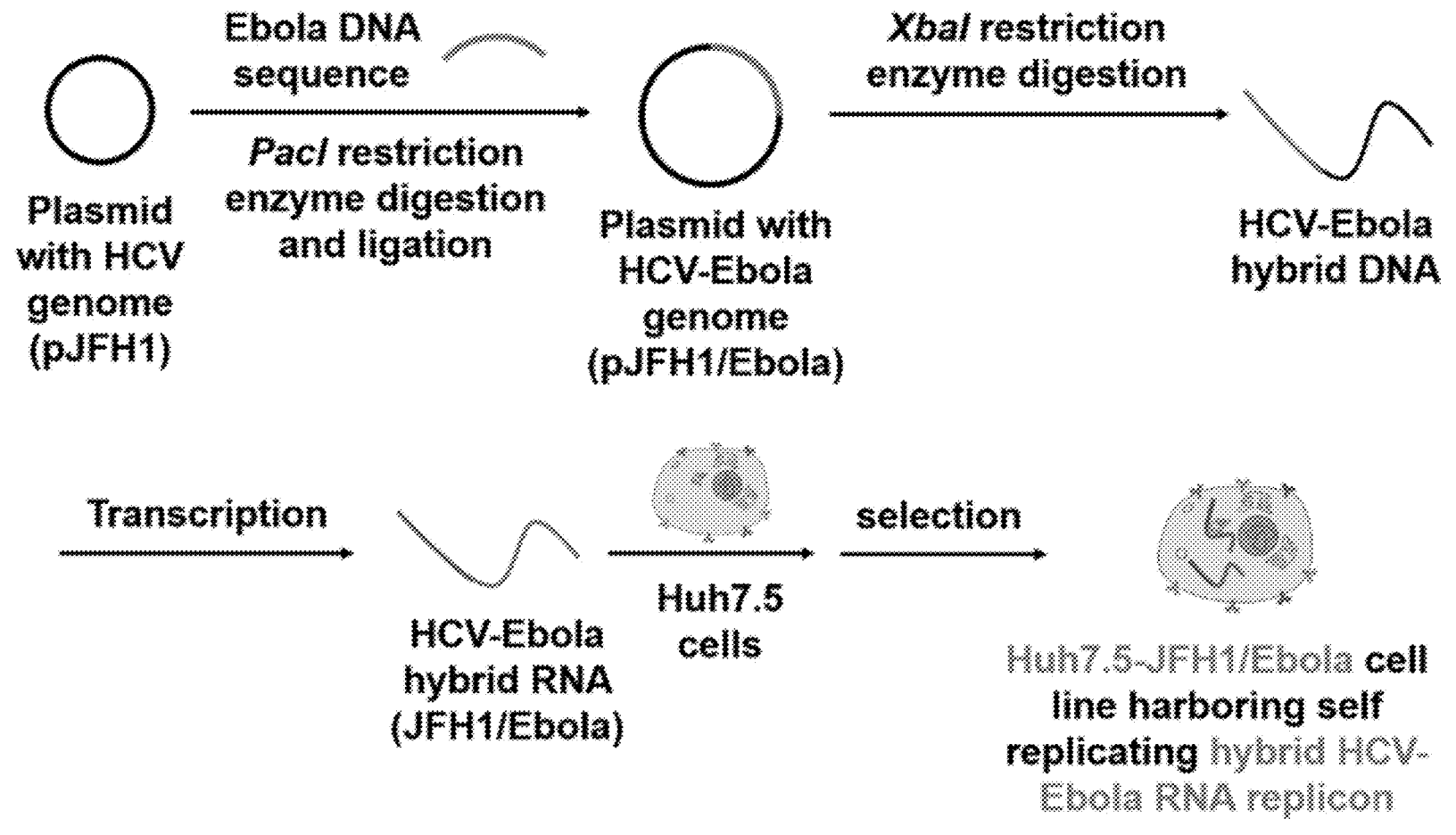

The detailed procedures of Ebola gene insertion and cell transfection were as follows, as shown in FIG. 41, a 201-base pair DNA fragment corresponding to the Ebola cGP was synthesized and inserted into pJFH1 plasmid and the plasmid was then transformed into E. coli. Because of their highly conserved nature cross all Ebola strains, Ebola cGP (−) and (+), negative strand and positive strand of Ebola virus cGP gene region locates in the 439-629 nt of glycoprotein gene were chosen as capturer DNA binding region. The Ebola cGP was synthesized and flanked by restriction enzyme PacI and then inserted into pJFH1 plasmid via PacI. The Ebola-pJFH1 plasmid extracted from *E. coli* culture was first screened by PCR to confirm the insertion of Ebola cGP gene fragment and then further evaluated by sequencing. The selected correct hybrid plasmids were linearized by restriction enzymes and then transcribed into corresponding Ebola-pJFH1 RNA. The Ebola-pJFH1 RNA was transfected into Huh7.5 cells via electroporation. The transfected cells were cultured in DMEM with 10% fetal bovine serum and 500 μg/mL G418 (Geneticin). The expression of Ebola-pJFH1 replicon was evaluated by immunofluorescence.

Figure 44:
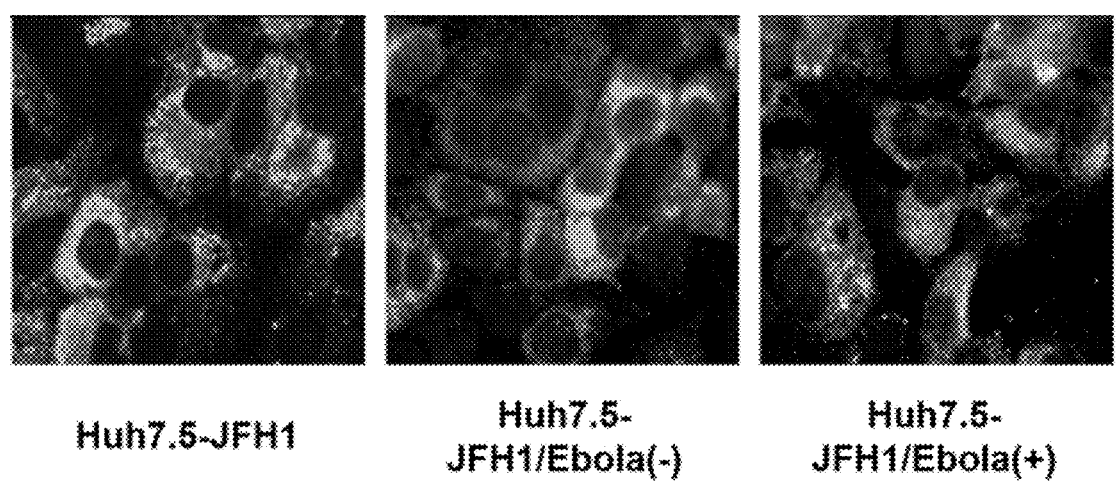
FIG. 44 shows immunofluorescence imaging of HCV viral protein expression within Huh7.5 cells with HCV RNA replicon or hybrid HCV-Ebola(−)/(+) RNA replicon.

The intracellular replication and expression of hybrid HCV-Ebola RNA was evaluated by immunofluorescence imaging. As shown in FIG. 44, both cells harboring HCV and hybrid HCV-Ebola RNA replicon presented similar fluorescence intensity, indicating that the insertion of Ebola gene did not influence the expression HCV viral proteins in Huh7.5 cells.

Figure 45:
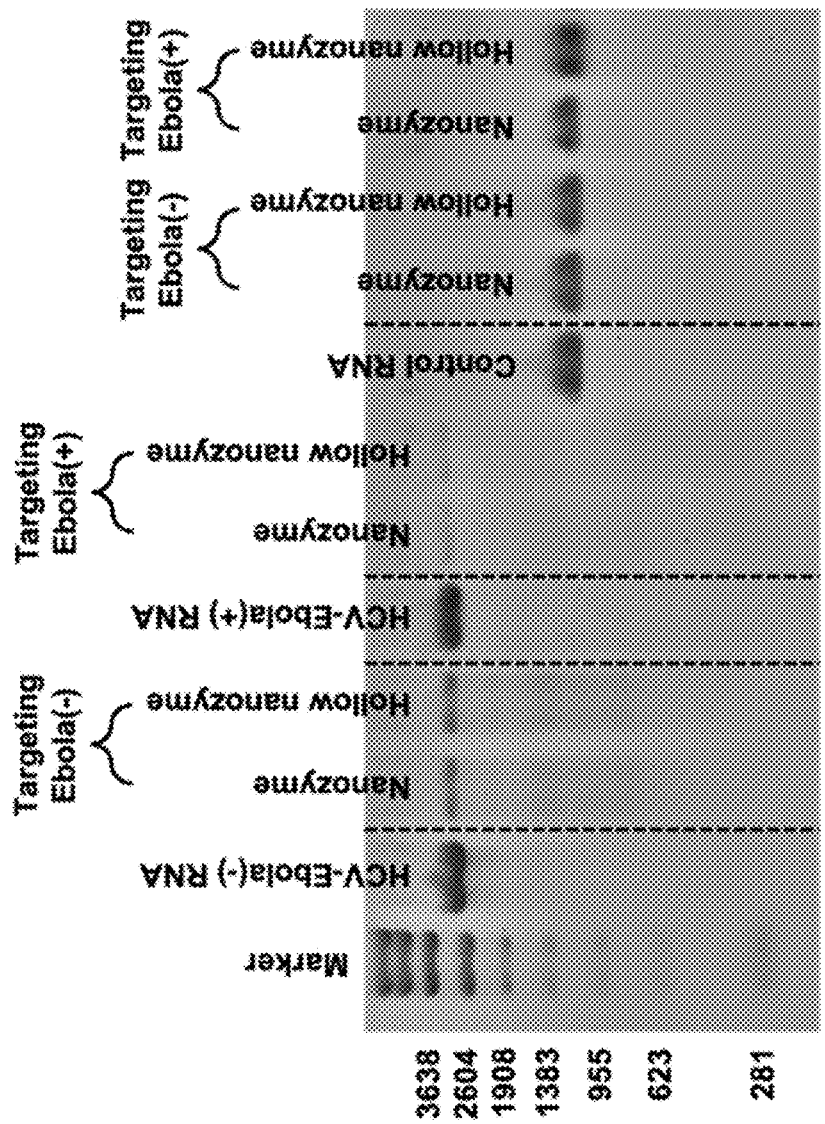
FIG. 45 shows ribonuclease activity tests for assessing the target selectivity of nanozyme and hollow nanozyme IIa with PEG-spacer capturer DNA targeting Ebola(−)/(+) RNA.

Demonstration of Nanozyme and Hollow Nanozyme IIa with Capturer DNA Targeting Ebola(−)/(+) RNA Nanozyme and hollow nanozyme IIa were prepared using PEG-spacer capturer DNA targeting Ebola(−)/(+) RNA with double thiol anchor at the 3'-end. The activity and selectivity of prepared nanozymes were demonstrated using the HCV-Ebola(−)/(+) hybrid RNA segments as target substrates and HCV RNA segments as control substrates. Electrophoresis analysis (FIG. 45) showed that both nanozyme and hollow nanozyme selectively degrade target HCV-Ebola(−)/(+) hybrid RNA segments, proving their excellent target RNA specificity.

Example 26. Demonstration of Nanozyme and Hollow Nanozyme IIa's RNase Inhibitor Resistance Because of the coverage from the densely packed oligonucleotides, the RNase A in nanozyme was protected from being accessible by RNA not complimentary to the capturer DNA. Such cooperativity leads to nanozymes' selective degradation toward target RNA.

Mammalian RNase inhibitor is a type of acidic protein specifically binds and inactivates pancreatic type RNase, including RNase A (Dickson K. A., et al. Prog Nucleic Acid Res Mol Biol. 2005, 80:349-374). Considering the steric hindrance and RNase inhibitor's poly anionic nature similar to non-complimentary control RNA segments, the nanozyme and hollow nanozyme were expected to be RNase inhibitor resistant (Scheme 42).

Figure 46B:
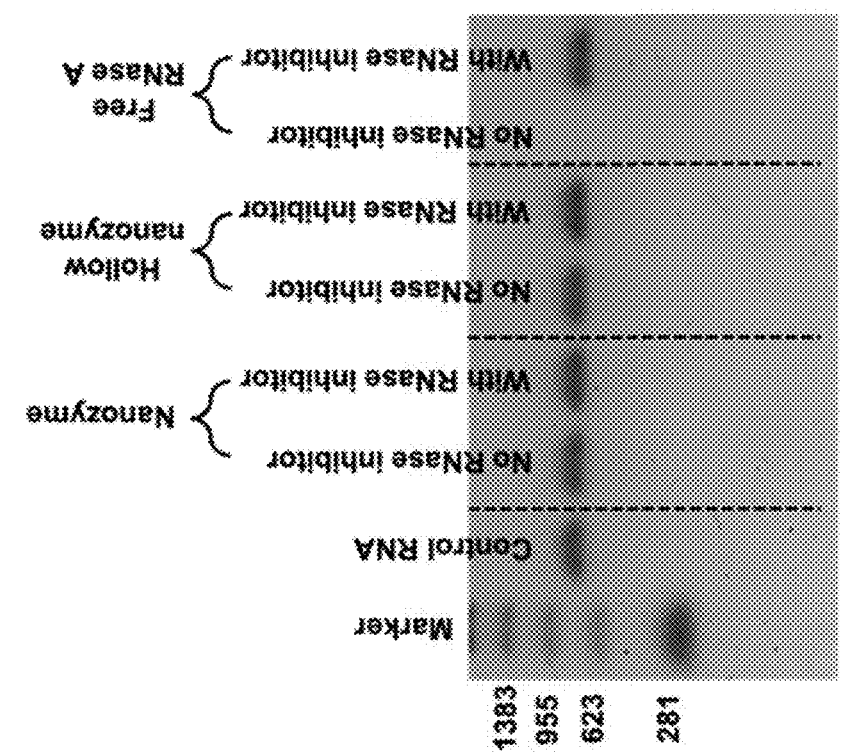
FIGS. 46A to 46B show ribonuclease activity tests for assessing the RNase inhibitor resistance of nanozyme and hollow nanozyme IIa with PEG-spacer capturer DNA targeting HCV RNA using target HCV RNA (FIG. 46A) or control RNA (FIG. 46B) as substrates.
Figure 46A:
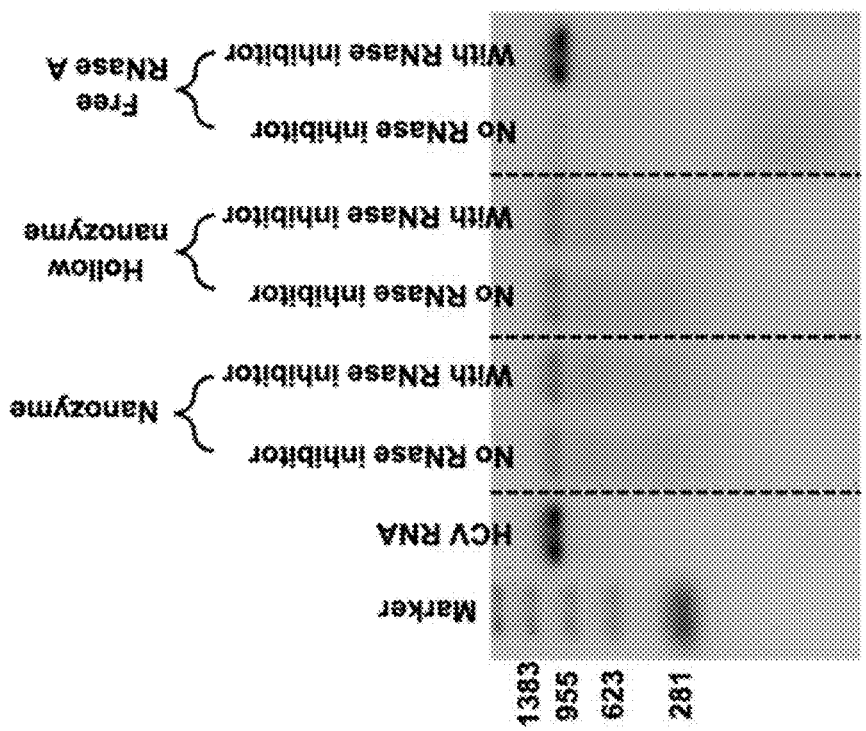
Figure 47B:
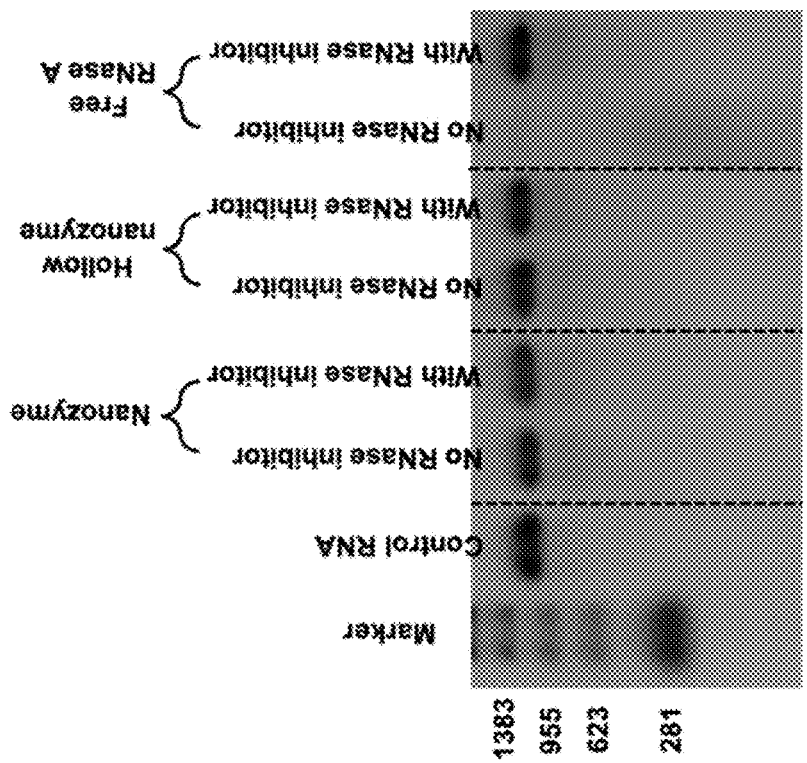
FIGS. 47A to 47B show ribonuclease activity tests for assessing the RNase inhibitor resistance of nanozyme and hollow nanozyme IIa with PEG-spacer capturer DNA targeting GPC3 RNA using target GPC3 RNA (FIG. 47A) or control RNA (FIG. 47B) as substrate.
Figure 47A:
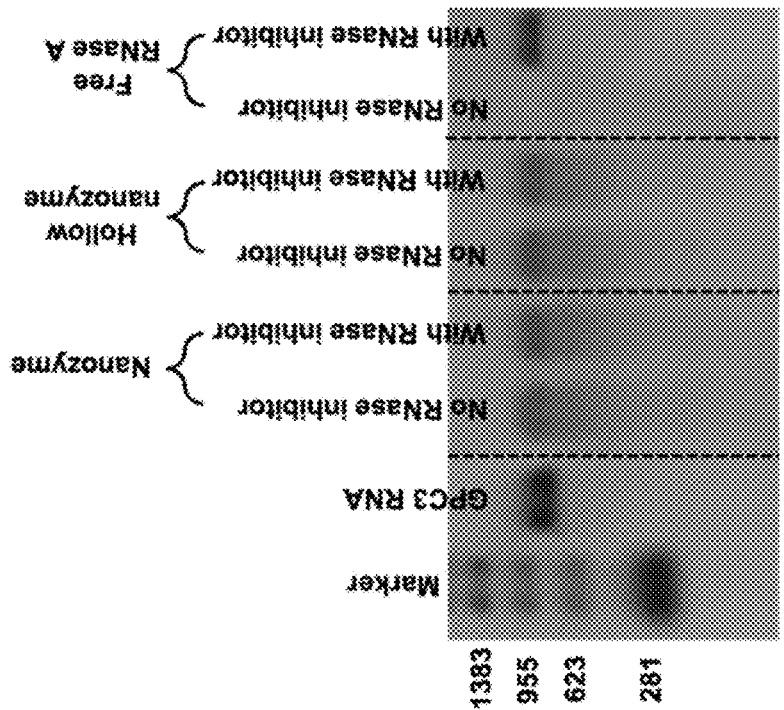
Figure 48A:
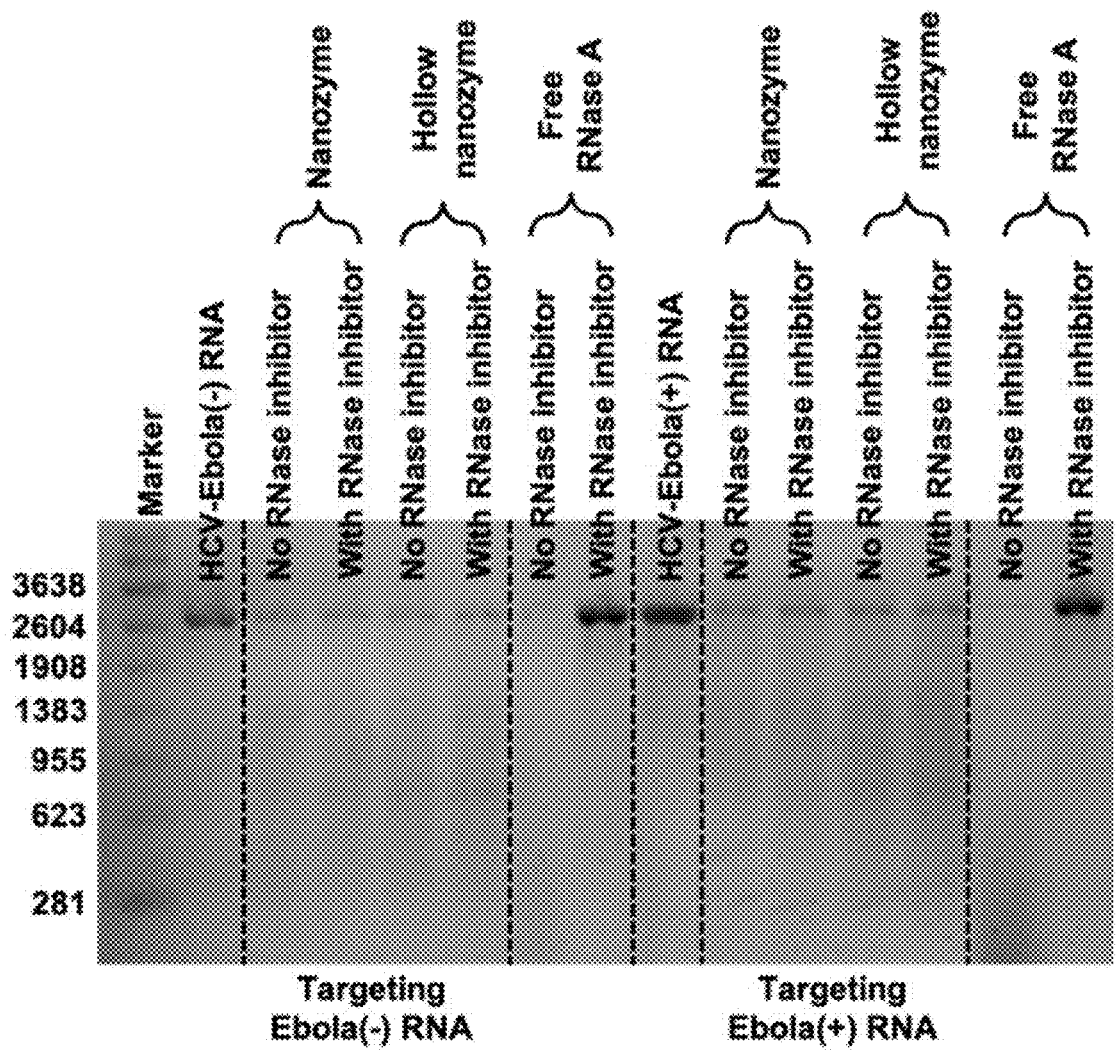
FIGS. 48A to 48B show ribonuclease activity tests for assessing the RNase inhibitor resistance of nanozyme and hollow nanozyme IIa with PEG-spacer capturer DNA targeting Ebola(−)/(+) RNA using target HCV-Ebola(−)/(+) RNA (FIG. 48A) or control RNA (FIG. 48B) as substrate.
Figure 48B:
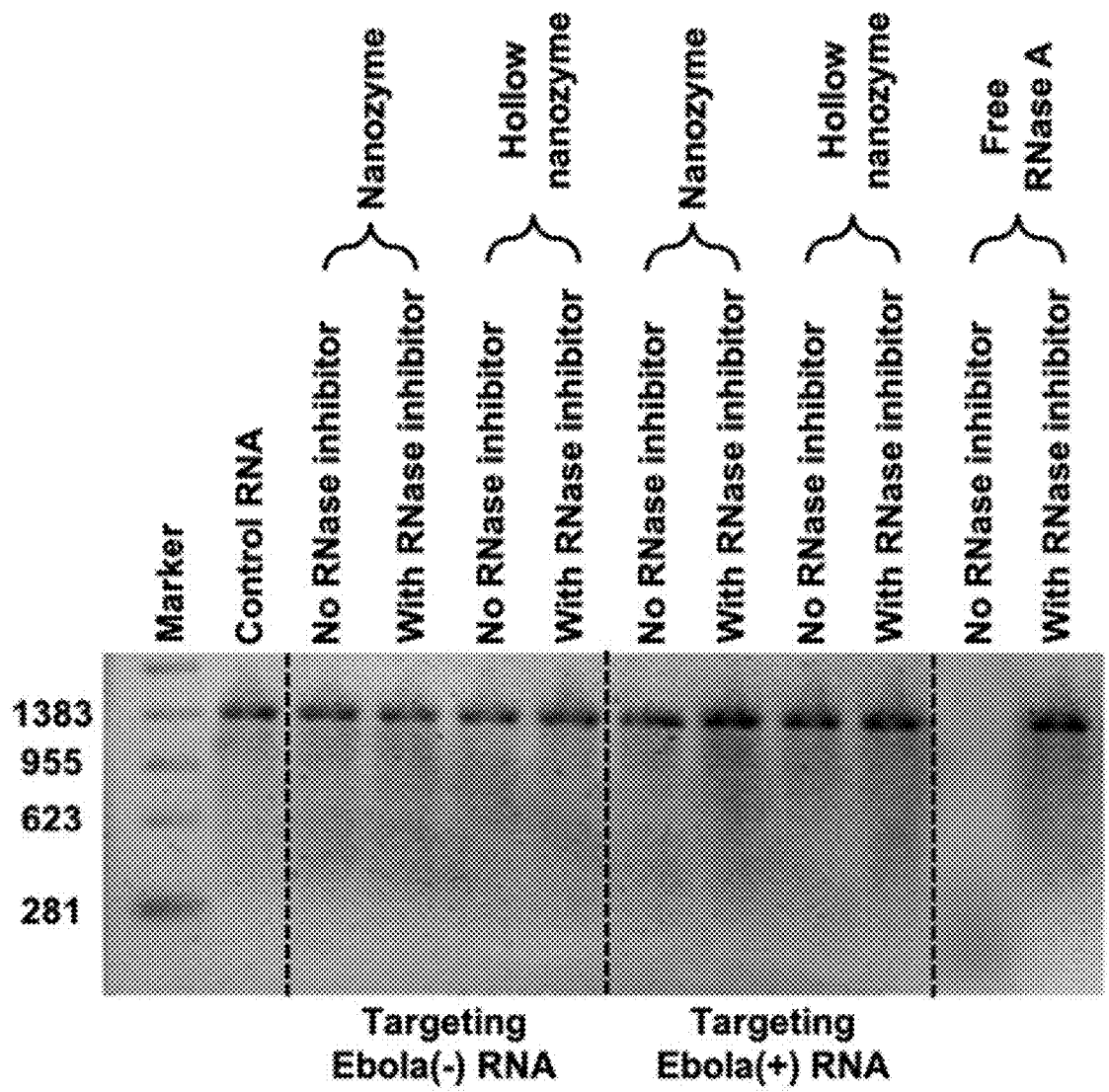

For verification, nanozyme and hollow nanozyme IIa with capturer DNA targeting HCV, GPC3 and Ebola RNA were evaluated. As shown in FIGS. 46-48, either with or without RNase inhibitor, all nanozymes and hollow nanozymes with different capturer DNA exhibited almost identical selective RNase activity toward target RNA segments, proving their excellent RNase inhibitor resistance. On the contrary, the RNase activity of free RNase A was easily inhibited by RNase inhibitor.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A nanozyme comprising a gold nanoparticle, an engineered ribonuclease-A enzyme and a DNA oligonucleotide,
   wherein the DNA oligonucleotide comprises a first RNA recognition moiety comprising a nucleic acid sequence complementary to a first region of an RNA target,
   wherein the engineered ribonuclease-A enzyme comprises a cysteine substitution, wherein the cysteine is functionalized by the method of reacting the cysteine with propargyl-maleimide to introduce an alkynyl group; synthesizing a PEG tether using 3'-dithiol serinol CPG, spacer phosphoramidite 18, and 5'-bromohexyl phosphoramidite, which introduces a 5'-bromide onto the PEG tether, converting the 5'-bromide into an azide using sodium azide, and using click chemistry to link the azide of the PEG tether to the alkynyl group on the cysteine,
   wherein the DNA oligonucleotide is attached to the gold nanoparticle directly or indirectly by gold-sulfur bonds, and
   wherein the RNA target is cleaved by the engineered ribonuclease-A enzyme when the first RNA recognition moiety binds to the RNA target.

2. The nanozyme of claim 1, further comprising a second RNA recognition moiety comprising a nucleic acid sequence complementary to a second region of the RNA target, wherein the second RNA recognition moiety is found on a separate DNA oligonucleotide independently attached to the gold nanoparticle or is attached to the first RNA recognition moiety by a brancher molecule.

3. The nanozyme of claim 1, wherein the DNA oligonucleotide is thiol-modified and is directly attached to the gold nanoparticle by a gold-sulfur bond.

4. The nanozyme of claim 2, wherein the second RNA recognition moiety is located on a second thiol-modified DNA oligonucleotide attached to the nanoparticle by a gold-sulfur bond.

5. The nanozyme of claim 2, wherein the brancher molecule comprises a 5-Me-dC brancher.

6. The nanozyme of claim 1, wherein the DNA oligonucleotide further comprises a blocker moiety comprising a nucleic acid sequence complementary to a blocker oligonucleotide, wherein binding of the blocker oligonucleotide to the blocker moiety sterically inhibits the RNA target from binding to the first RNA recognition site.

7. The nanozyme of claim 1, wherein in the nanozyme, a unibody molecule is attached to the gold nanoparticle by a gold-sulfur bond, wherein the unibody molecule comprises (i) the recombinant RNase-A enzyme, and (ii) the first RNA recognition moiety and/or a second RNA recognition moiety.

8. A method for silencing RNA in a cell, comprising contacting the cell with the nanozyme of claim 1.

\* \* \* \* \*

SEQUENCE LISTING

```
<160> NUMBER OF SEQ ID NOS: 21

<210> SEQ ID NO 1
<211> LENGTH: 57
<212> TYPE: RNA
<213> ORGANISM: Artificial Sequence
<220> FEATURE:
<223> OTHER INFORMATION: Synthetic Construct

<400> SEQUENCE: 1
ggucucguag accgugcacc augagcacac uuccaaaacc caaagaaaaa cgagacc         57

<210> SEQ ID NO 2
<211> LENGTH: 54
<212> TYPE: RNA
<213> ORGANISM: Artificial Sequence
<220> FEATURE:
<223> OTHER INFORMATION: Synthetic Construct

<400> SEQUENCE: 2
ggucugguau accgugcacc augagcacac uuccaaaacc caaggaaaa cgag             54

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct
```

```
<400> SEQUENCE: 3
ccagagcatc tggcacgt                                              18

<210> SEQ ID NO 4
<211> LENGTH: 18
<212> TYPE: DNA
<213> ORGANISM: Artificial Sequence
<220> FEATURE:
<223> OTHER INFORMATION: Synthetic Construct

<400> SEQUENCE: 4
ccagaccata tggcacgt                                              18

<210> SEQ ID NO 5
<211> LENGTH: 15
<212> TYPE: DNA
<213> ORGANISM: Artificial Sequence
<220> FEATURE:
<223> OTHER INFORMATION: Synthetic Construct

<400> SEQUENCE: 5
ccagagcatc tggca                                                 15

<210> SEQ ID NO 6
<211> LENGTH: 12
<212> TYPE: DNA
<213> ORGANISM: Artificial Sequence
<220> FEATURE:
<223> OTHER INFORMATION: Synthetic Construct

<400> SEQUENCE: 6
ccagagcatc tg                                                    12

<210> SEQ ID NO 7
<211> LENGTH: 12
<212> TYPE: DNA
<213> ORGANISM: Artificial Sequence
<220> FEATURE:
<223> OTHER INFORMATION: Synthetic Construct

<400> SEQUENCE: 7
ccagagcatc tg                                                    12

<210> SEQ ID NO 8
<211> LENGTH: 12
<212> TYPE: DNA
<213> ORGANISM: Artificial Sequence
<220> FEATURE:
<223> OTHER INFORMATION: Synthetic Construct

<400> SEQUENCE: 8
ccagaccata tg                                                    12

<210> SEQ ID NO 9
<211> LENGTH: 18
<212> TYPE: RNA
<213> ORGANISM: Artificial Sequence
<220> FEATURE:
<223> OTHER INFORMATION: Synthetic Construct

<400> SEQUENCE: 9
ggucucguag accgugca                                              18

<210> SEQ ID NO 10
<211> LENGTH: 32
```

```
<212> TYPE: RNA
<213> ORGANISM: Artificial Sequence
<220> FEATURE:
<223> OTHER INFORMATION: Synthetic Construct

<400> SEQUENCE: 10
guagaccgug caaaaaaaaa aaaaaaaaaa aa                              32

<210> SEQ ID NO 11
<211> LENGTH: 32
<212> TYPE: DNA
<213> ORGANISM: Artificial Sequence
<220> FEATURE:
<223> OTHER INFORMATION: Synthetic Construct

<400> SEQUENCE: 11 ttttttttttt tttttttttt tgcacggtct ac                             32

<210> SEQ ID NO 12
<211> LENGTH: 18
<212> TYPE: RNA
<213> ORGANISM: Artificial Sequence
<220> FEATURE:
<223> OTHER INFORMATION: Synthetic Construct

<400> SEQUENCE: 12
ggucucguag accgugca                                              18

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
tgcacggtct acgagacc                                              18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
agtaggctag tccagaat                                              18

<210> SEQ ID NO 15
<211> LENGTH: 36
<212> TYPE: DNA
<213> ORGANISM: Artificial Sequence
<220> FEATURE:
<223> OTHER INFORMATION: Synthetic Construct

<400> SEQUENCE: 15
cagaatctag tccagaattg cacggtctac gagacc                          36

<210> SEQ ID NO 16
<211> LENGTH: 55
<212> TYPE: DNA
<213> ORGANISM: Artificial Sequence
<220> FEATURE:
<223> OTHER INFORMATION: Synthetic Construct

<400> SEQUENCE: 16
```
agtaggtagt tctcaattct ggactagatt ctggcgagag atatagcatg ctcgc    55

<210> SEQ ID NO 17
<211> LENGTH: 18
<212> TYPE: DNA
<213> ORGANISM: Artificial Sequence
<220> FEATURE:
<223> OTHER INFORMATION: Synthetic Construct

<400> SEQUENCE: 17
attctggact agattctg    18

<210> SEQ ID NO 18
<211> LENGTH: 43
<212> TYPE: DNA
<213> ORGANISM: Artificial Sequence
<220> FEATURE:
<223> OTHER INFORMATION: Synthetic Construct

<400> SEQUENCE: 18
gcgagcatga gtctatatct ctcgccagaa tctagtccag aat    43

<210> SEQ ID NO 19
<211> LENGTH: 61
<212> TYPE: DNA
<213> ORGANISM: Artificial Sequence
<220> FEATURE:
<223> OTHER INFORMATION: Synthetic Construct

<400> SEQUENCE: 19
agtaggtagt agatctcaat tctggactag attctggcga gagatataga ctcatgctcg    60
c    61

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20
tgcacggtct acgagacc    18

<210> SEQ ID NO 21
<211> LENGTH: 12
<212> TYPE: DNA
<213> ORGANISM: Artificial Sequence
<220> FEATURE:
<223> OTHER INFORMATION: Synthetic Construct

<400> SEQUENCE: 21
gtctacgaga cc    12